(12) United States Patent
Croteau et al.

(10) Patent No.: US 7,416,872 B2
(45) Date of Patent: *Aug. 26, 2008

(54) TAXOID OXYGENASES AND THEIR USES

(75) Inventors: Rodney B. Croteau, Pullman, WA (US); Anne Schoendorf, Bossey (FR); Stefan Jennewein, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/242,662

(22) Filed: Oct. 3, 2005

(65) Prior Publication Data
US 2007/0067864 A1    Mar. 22, 2007

Related U.S. Application Data

(60) Division of application No. 10/884,115, filed on Jul. 1, 2004, now Pat. No. 7,005,283, which is a division of application No. 10/142,231, filed on May 8, 2002, now Pat. No. 6,787,343, which is a continuation of application No. PCT/US00/31254, filed on Nov. 13, 2000.

(60) Provisional application No. 60/165,250, filed on Nov. 12, 1999.

(51) Int. Cl.
*C12N 9/02* (2006.01)
*C12N 15/00* (2006.01)
*C12N 1/20* (2006.01)
*C12N 5/00* (2006.01)
*C12P 21/04* (2006.01)
*C12Q 1/26* (2006.01)
*C07H 21/04* (2006.01)
*C12Q 1/00* (2006.01)
*C12Q 1/68* (2006.01)

(52) U.S. Cl. .............................. 435/189; 435/4; 435/6; 435/25; 435/69.1; 435/71.1; 435/252.3; 435/320.1; 435/440; 435/410; 536/23.2

(58) Field of Classification Search ...................... None
See application file for complete search history.

(56) References Cited

U.S. PATENT DOCUMENTS

| | | |
|---|---|---|
| 6,787,343 B2 | 9/2004 | Croteau et al. |
| 7,005,283 B2 * | 2/2006 | Croteau et al. ............. 435/189 |
| 2003/0166176 A1 | 9/2003 | Croteau et al. |
| 2004/0236089 A1 | 11/2004 | Croteau et al. |

OTHER PUBLICATIONS

Cabello et al., "Cloning, Expression in Yeast, and Functional Characterization of CYP81B1, a Plant Cytochrome P450 That Catalyzes In-Chain Hydroxylation of Fatty Acids," *J. Biol. Chem.*, 273(13):7260-7267, 1998.

(Continued)

*Primary Examiner*—Yong D Pak
(74) *Attorney, Agent, or Firm*—Paula A. DeGrandis; Klarquist Sparkman, LLP

(57) ABSTRACT

Oxygenase enzymes and the use of such enzymes to produce paclitaxel (Taxol™), related taxoids, as well as intermediates in the Taxol biosynthetic pathway are disclosed. Also disclosed are nucleic acid sequences encoding the oxygenase enzymes.

8 Claims, 15 Drawing Sheets

OTHER PUBLICATIONS

Chau et al., "Taxol Biosynthesis: Molecular Cloning and Characterization of a Cytochrome P450 Taxoid 7β-Hydroxylase," Chem. Biol., 11:663-672, 2004.

Chau et al., *Molecular Cloning and Characterization of Three Enzymes Involved in Taxol/Taxoid Biosynthesis: Taxoid 2α-Hydroxylase, Taxoid 7β-Hydroxylase, and Taxoid 5α-O-Acetyltransferase*, Ph.D. Dissertation, Pullman, WA:Washington State University, May 2004.

Eisenreich et al., "Multiple Oxygenase Reactions in the Biosynthesis of Taxoids," *J. Am. Chem. Soc.*, 120(37):9694-9695, 1998.

Hefner et al., "Cytochrome P450-Catalyzed Hydroxylation of Taxa-4(5), 11(12)-diene to Taxa-4(20), 11(12)-dien-5α-ol: The First Oxygenation Step in Taxol Biosynthesis," *Chem. Biol.*, 3:479-489, 1996.

Jennewein et al., "Taxol biosynthesis: Taxane 13α-hydroxylase is a cytochrome P450-dependent monooxygenase," *Proc. Natl. Acad. Sci. USA*, 98(24):13595-13600, 2001.

Jennewein et al., "Random sequencing of an induced Taxus cell cDNA library for identification of clones involved in Taxol biosynthesis," *Proc. Natl. Acad. Sci. USA*, 101(24):9149-9154, 2004.

Pauli et al., "Molecular Cloning and Functional Heterologous Expression of Two Alleles Encoding (S)-N-Methylcoclaurine 3'-hydroxylase (CYP80B1), a New Methyl Jasmonate-Inducible Cytochrome P-450-Dependent Mono-Oxygenase of Benzylisoquinoline Alkaloid Biosynthesis," *Plant J.*, 13(6):793-801, 1998.

Schoendorf et al., "Molecular Cloning of a Cytochrome P450 Taxane 10β-Hydroxylase cDNA from *Taxus* and Functional Expression in Yeast," *Proc. Natl. Acad. Sci. USA*, 98(4):1501-1506, 2001.

Tsumura et al., "Sequence-Tagged-Sites (STSs) of cDNA clones in *Cryptomeria japonica* and their Evaluation as Molecular Markers in Conifers," Theor. Appl. Genet., 94:764-772, 1997.

Wildung et al., "A cDNA Clone for Taxadiene Synthase, the Diterpene Cyclase that Catalyzes the Committed Step of Taxol Biosynthesis," J. Biol. Chem., 271(16):9201-9204, 1996.

* cited by examiner

| Conserved motif in the heme binding domain NH2 | | P | F | G | | SEQ ID NO: |
|---|---|---|---|---|---|---|
| | | cca | ttc | gg | 3' | |
| | | t | t | | | |
| | | c | | | | |
| | | g | | | | |
| | | | | | | |
| 5' | attaaccctcactaaa | cct | ttt | gg | 3' | 73 |
| 5' | attaaccctcactaaa | cct | ttc | gg | 3' | 74 |
| 5' | attaaccctcactaaa | cca | ttt | gg | 3' | 75 |
| 5' | attaaccctcactaaa | cca | ttc | gg | 3' | 76 |
| 5' | attaaccctcactaaa | ccg | ttt | gg | 3' | 77 |
| 5' | attaaccctcactaaa | ccg | ttc | gg | 3' | 78 |
| 5' | attaaccctcactaaa | ccc | ttt | gg | 3' | 79 |
| 5' | attaaccctcactaaa | ccc | ttc | gg | 3' | 80 |

Fig. 4

% of identity

| | F12 | F21 | F42 | F51 | F72 | F9 | F31 | F14 | F19 | F56 | F55 | F10 | F34 |
|---|---|---|---|---|---|---|---|---|---|---|---|---|---|
| F12 | ■ | 83 | 61 | 57 | 57 | 67 | 53 | 69 | 62 | 75 | 66 | 21 | 20 |
| F21 | 85 | ■ | 62 | 58 | 55 | 67 | 52 | 67 | 60 | 74 | 66 | 20 | 20 |
| F42 | 67 | 68 | ■ | 59 | 57 | 66 | 52 | 64 | 57 | 61 | 63 | 13 | 20 |
| F51 | 65 | 65 | 66 | ■ | 53 | 62 | 53 | 61 | 55 | 59 | 60 | 0 | 16 |
| F72 | 67 | 65 | 64 | 61 | ■ | 59 | 57 | 60 | 59 | 58 | 58 | 16 | 19 |
| F9 | 74 | 75 | 69 | 67 | 67 | ■ | 53 | 69 | 61 | 67 | 70 | 20 | 20 |
| F31 | 63 | 63 | 60 | 61 | 66 | 62 | ■ | 56 | 55 | 53 | 55 | 20 | 18 |
| F14 | 79 | 77 | 72 | 68 | 69 | 76 | 65 | ■ | 64 | 66 | 71 | 23 | 22 |
| F19 | 71 | 68 | 65 | 63 | 67 | 68 | 64 | 72 | ■ | 61 | 63 | 14 | 23 |
| F56 | 80 | 80 | 66 | 65 | 67 | 74 | 62 | 76 | 69 | ■ | 66 | 21 | 20 |
| F55 | 71 | 72 | 69 | 68 | 67 | 76 | 64 | 79 | 70 | 72 | ■ | 13 | 20 |
| F10 | 32 | 31 | 26 | 14 | 26 | 26 | 30 | 31 | 28 | 31 | 26 | ■ | 37 |
| F34 | 31 | 31 | 26 | 16 | 28 | 31 | 29 | 34 | 31 | 30 | 31 | 51 | ■ |

% of similarity

Fig. 5B

Percent Sequence Identity

| Clone/SEQ ID NO: | F10/68 | F12/56 | F14/64 | F15/91 | F16/88 | F19/63 | F21/57 | F23/90 | F31/59 | F34/66 | F38/92 | F42/58 | F51/60 | F55/65 | F56/62 | F71/89 | F72/67 | F82/87 | F9/61 |
|---|---|---|---|---|---|---|---|---|---|---|---|---|---|---|---|---|---|---|---|
| F10 |  | 15 | 16 | 14 | 16 | 15 | 16 | 14 | 15 | 32 | 15 | 14 | 14 | 14 | 14 | 14 | 14 | 15 | 14 |
| F12 | 28 |  | 68 | 56 | 60 | 60 | 82 | 29 | 51 | 15 | 22 | 59 | 55 | 65 | 74 | 64 | 56 | 62 | 65 |
| F14 | 27 | 79 |  | 58 | 63 | 62 | 66 | 28 | 55 | 17 | 26 | 62 | 60 | 70 | 66 | 69 | 60 | 65 | 68 |
| F15 | 25 | 66 | 67 |  | 57 | 55 | 54 | 27 | 59 | 13 | 23 | 55 | 53 | 57 | 55 | 60 | 66 | 60 | 55 |
| F16 | 27 | 71 | 72 | 67 |  | 58 | 60 | 30 | 56 | 17 | 25 | 57 | 55 | 60 | 61 | 61 | 60 | 62 | 60 |
| F19 | 25 | 70 | 71 | 65 | 68 |  | 58 | 27 | 54 | 15 | 24 | 55 | 53 | 60 | 60 | 63 | 57 | 75 | 60 |
| F21 | 28 | 85 | 77 | 65 | 71 | 68 |  | 29 | 51 | 13 | 23 | 59 | 54 | 65 | 74 | 66 | 55 | 62 | 65 |
| F23 | 25 | 41 | 42 | 41 | 42 | 40 | 42 |  | 25 | 14 | 24 | 28 | 25 | 28 | 28 | 28 | 29 | 30 | 29 |
| F31 | 26 | 63 | 64 | 70 | 65 | 63 | 63 | 42 |  | 29 | 15 | 51 | 52 | 53 | 53 | 55 | 56 | 55 | 52 |
| F34 | 51 | 29 | 30 | 25 | 29 | 27 | 28 | 26 | 27 |  | 25 | 15 | 16 | 15 | 16 | 16 | 15 | 14 | 15 |
| F38 | 28 | 37 | 40 | 38 | 38 | 37 | 38 | 38 | 40 | 29 |  | 25 | 22 | 25 | 23 | 25 | 25 | 25 | 25 |
| F42 | 27 | 66 | 70 | 64 | 67 | 64 | 67 | 42 | 60 | 29 | 38 |  | 58 | 61 | 60 | 62 | 56 | 58 | 65 |
| F51 | 25 | 64 | 68 | 62 | 65 | 63 | 64 | 39 | 62 | 26 | 35 | 66 |  | 59 | 57 | 58 | 51 | 56 | 61 |
| F55 | 28 | 72 | 79 | 66 | 71 | 69 | 73 | 42 | 63 | 29 | 40 | 67 | 68 |  | 65 | 75 | 57 | 63 | 67 |
| F56 | 26 | 80 | 77 | 66 | 71 | 68 | 81 | 42 | 63 | 29 | 38 | 66 | 65 | 73 |  | 66 | 65 | 63 | 66 |
| F7 | 26 | 72 | 76 | 68 | 70 | 69 | 73 | 43 | 65 | 27 | 39 | 69 | 66 | 83 | 74 |  | 60 | 66 | 67 |
| F72 | 27 | 67 | 69 | 75 | 68 | 66 | 66 | 40 | 66 | 26 | 38 | 63 | 61 | 67 | 66 | 67 |  | 59 | 57 |
| F82 | 26 | 72 | 72 | 67 | 71 | 83 | 71 | 43 | 66 | 28 | 39 | 66 | 65 | 71 | 72 | 72 | 66 |  | 64 |
| F9 | 27 | 73 | 74 | 62 | 67 | 67 | 73 | 42 | 60 | 28 | 39 | 66 | 64 | 75 | 72 | 73 | 65 | 71 |  |

Fig. 5D

TAXOID OXYGENASES AND THEIR USES

REFERENCE TO RELATED APPLICATIONS

This is a divisional of U.S. application Ser. No. 10/884,115, now U.S. Pat. No. 7,005,283, filed Jul. 1, 2004, which is a divisional of U.S. application Ser. No. 10/142,231, now U.S. Pat. No. 6,787,343, filed May 8, 2002, which is a continuation of International Application No. PCT/US00/31254, filed Nov. 13, 2000, which claims the benefit of U.S. Provisional Application No. 60/165,250, filed Nov. 12, 1999, each of which applications is incorporated herein in its entirety.

ACKNOWLEDGMENT OF GOVERNMENT SUPPORT

This invention was made with government support under National Cancer Institute Grant No. CA-55254. The government has certain rights in this invention.

FIELD OF THE INVENTION

The invention relates to oxygenase enzymes and methods of using such enzymes to produce Taxol (paclitaxel) and related taxoids.

INTRODUCTION

Cytochrome P450

Cytochrome P450 proteins are enzymes that have a unique sulfur atom ligated to the heme iron and that, when reduced, form carbon monoxide complexes. When complexed to carbon monoxide they display a major absorption peak (Soret band) near 450 nm. There are numerous members of the cytochrome P450 group including enzymes from both plants and animals. Members of the cytochrome P450 group can catalyse reactions such as unspecific monooxygenation, camphor 5-monooxygenation, steroid 11β-monooxygenation, and cholesterol monooxygenation (Smith et al. (eds.), Oxford Dictionary of Biochemistry and Molecular Biology, Oxford University Press, New York, 1997).

Paclitaxel

The complex diterpenoid Taxol (® Bristol-Myers Squibb; common name paclitaxel) (Wani et al., *J. Am. Chem. Soc.* 93:2325-2327, 1971) is a potent antimitotic agent with excellent activity against a wide range of cancers, including ovarian and breast cancer (Arbuck and Blaylock, *Taxol: Science and Applications*, CRC Press, Boca Raton, 397-415, 1995; Holmes et al., *ACS Symposium Series* 583:31-57, 1995). Taxol was isolated originally from the bark of the Pacific yew (*Taxus brevifolia*). For a number of years, Taxol was obtained exclusively from yew bark, but low yields of this compound from the natural source coupled to the destructive nature of the harvest, prompted new methods of Taxol production to be developed. Taxol currently is produced primarily by semisynthesis from advanced taxane metabolites (Holton et al., *Taxol: Science and Applications*, CRC Press, Boca Raton, 97-121, 1995) that are present in the needles (a renewable resource) of various *Taxus* species. However, because of the increasing demand for this drug both for use earlier in the course of cancer intervention and for new therapeutic applications (Goldspiel, *Pharmacotherapy* 17:110S-125S, 1997), availability and cost remain important issues. Total chemical synthesis of Taxol currently is not economically feasible. Hence, biological production of the drug and its immediate precursors will remain the method of choice for the foreseeable future. Such biological production may rely upon either intact *Taxus* plants, Taxus cell cultures (Ketchum et al., *Biotechnol. Bioeng.* 62:97-105, 1999), or, potentially, microbial systems (Stierle et al., *J. Nat. Prod.* 58:1315-1324, 1995). In all cases, improving the biological production yields of Taxol depends upon a detailed understanding of the biosynthetic pathway, the enzymes catalyzing the sequence of reactions, especially the rate-limiting steps, and the genes encoding these proteins. Isolation of genes encoding enzymes involved in the pathway is a particularly important goal, since overexpression of these genes in a producing organism can be expected to markedly improve yields of the drug.

The Taxol biosynthetic pathway is considered to involve more than 12 distinct steps (Floss and Mocek, *Taxol: Science and Applications*, CRC Press, Boca Raton, 191-208, 1995; and Croteau et al., *Curr. Top. Plant Physiol.* 15:94-104, 1996). However, very few of the enzymatic reactions and intermediates of this complex pathway have been defined. The first committed enzyme of the Taxol pathway is taxadiene synthase (Koepp et al., *J. Biol. Chem.* 270:8686-8690, 1995) that cyclizes the common precursor geranylgeranyl diphosphate (Hefner et al., *Arch. Biochem. Biophys.* 360:62-74, 1998) to taxadiene (FIG. 1). The cyclized intermediate subsequently undergoes modification involving at least eight oxygenation steps, a formal dehydrogenation, an epoxide rearrangement to an oxetane, and several acylations (Floss and Mocek, *Taxol: Science and Applications*, CRC Press, Boca Raton, 191-208, 1995; and Croteau et al., *Curr. Top. Plant Physiol.* 15:94-104, 1996). Taxadiene synthase has been isolated from *T. brevifolia* and characterized (Hezari et al., *Arch. Biochem. Biophys.* 322:437-444, 1995), the mechanism of action defined (Lin et al., *Biochemistry* 35:2968-2977, 1996), and the corresponding cDNA clone isolated and expressed (Wildung and Croteau, *J. Biol. Chem.* 271:9201-9204, 1996).

The second specific step of Taxol biosynthesis is an oxygenation (hydroxylation) reaction catalyzed by taxadiene-5α-hydroxylase. The enzyme has been demonstrated in *Taxus* microsome preparations (Hefner et al., *Methods Enzymol.* 272:243-250, 1996), shown to catalyze the stereospecific hydroxylation of taxa-4(5),11(12)-diene to taxa-4(20),11(12)-dien-5α-ol (i.e., with double-bond rearrangement), and characterized as a cytochrome P450 oxygenase (Hefner et al., i Chemistry and Biology 3:479-489, 1996).

Since the first specific oxygenation step of the Taxol pathway was catalyzed by a cytochrome P450 oxygenase, it was logical to assume that subsequent oxygenation (hydroxylation and epoxidation) reactions of the pathway would be carried out by similar cytochrome P450 enzymes. Microsomal preparations (Hefner et al., *Methods Enzymol.* 272:243-250, 1996) were optimized for this purpose, and shown to catalyze the hydroxylation of taxadiene or taxadien-5α-ol to the level of a pentaol (see FIG. 2 for tentative biosynthetic sequence and structures based on the evaluation of taxane metabolite abundances (Croteau et al., *Curr. Topics Plant Physiol.* 15:94-104, 1995)), providing evidence for the involvement of at least five distinct cytochrome P450 taxane (taxoid) hydroxylases in this early part of the pathway (Hezari et al., *Planta Med.* 63:291-295, 1997).

Also, the remaining three oxygenation steps (C1 and C7 hydroxylations and an epoxidation at C4-C20; see FIGS. 1 and 3) likely are catalyzed by cytochrome P450 enzymes, but these reactions reside too far down the pathway to observe in microsomes by current experimental methods (Croteau et al., *Curr. Topics Plant Physiol.* 15:94-104, 1995; and Hezari et al., *Planta Med.* 63:291-295, 1997). Since *Taxus* (yew) plants and cells do not appear to accumulate taxoid metabolites bearing fewer than six oxygen atoms (i.e., hexaol or epoxy-pentaol) (Kingston et al., *Prog. Chem. Org. Nat. Prod.* 61:1-206, 1993), such intermediates must be rapidly transformed down the pathway, indicating that the oxygenations (hydroxylations) are relatively slow pathway steps and, thus, important targets for gene cloning.

Isolation of the genes encoding the oxygenases that catalyze the oxygenase steps of Taxol biosynthesis would represent an important advance in efforts to increase Taxol and taxoid yields by genetic engineering and in vitro synthesis.

SUMMARY OF THE INVENTION

The invention stems from the discovery of twenty-one amplicons (regions of DNA amplified by a pair of primers using the polymerase chain reaction (PCR)). These amplicons can be used to identify oxygenases, for example, the oxygenases shown in SEQ ID NOS: 56-68 and 87-92 that are encoded by the nucleic acid sequences shown in SEQ ID NOS: 43-55 and 81-86. These sequences are isolated from the *Taxus* genus, and the respective oxygenases are useful for the synthetic production of Taxol and related taxoids, as well as intermediates within the Taxol biosynthetic pathway, and other taxoid derivatives. The sequences also can be used for the creation of transgenic organisms that either produce the oxygenases for subsequent in vitro use, or produce the oxygenases in vivo so as to alter the level of Taxol and taxoid production within the transgenic organism.

Another aspect of the invention provides the nucleic acid sequences shown in SEQ ID NOS: 1-21 and the corresponding amino acid sequences shown in SEQ ID NOS: 22-42, respectively, as well as fragments of these nucleic acid sequences and amino acid sequences. These sequences are useful for isolating the nucleic acid and amino acid sequences corresponding to full-length oxygenases. These amino acid sequences and nucleic acid sequences are also useful for creating specific binding agents that recognize the corresponding oxygenases.

Accordingly, another aspect of the invention provides for the identification of oxygenases and fragments of oxygenases that have amino acid and nucleic acid sequences that vary from the disclosed sequences. For example, the invention provides oxygenase amino acid sequences that vary by one or more conservative amino acid substitutions, or that share at least 50% sequence identity with the amino acid sequences provided while maintaining oxygenase activity.

The nucleic acid sequences encoding the oxygenases and fragments of the oxygenases that maintain taxoid oxygenase and/or CO binding activity can be cloned, using standard molecular biology techniques, into vectors. These vectors then can be used to transform host cells. Thus, a host cell can be modified to express either increased levels of oxygenase or decreased levels of oxygenase.

Another aspect of the invention provides methods for isolating nucleic acid sequences encoding full-length oxygenases. The methods involve hybridizing at least ten contiguous nucleotides of any of the nucleic acid sequences shown in SEQ ID NOS: 1-21, 43-55, and 81-86 to a second nucleic acid sequence, wherein the second nucleic acid sequence encodes a taxoid oxygenase and/or maintains CO binding activity. This method can be practiced in the context of, for example, Northern blots, Southern blots, and the polymerase chain reaction (PCR). Hence, the invention also provides the oxygenases identified by this method.

Yet another aspect of the invention involves methods of adding at least one oxygen atom to at least one taxoid. These methods can be practiced in vivo or in vitro, and can be used to add oxygen atoms to various intermediates in the Taxol biosynthetic pathway, as well as to add oxygen atoms to related taxoids that are not necessarily on a Taxol biosynthetic pathway. These methods include for example, adding oxygen atoms to acylation or glycosylation variants of paclitaxel, baccatin III, or 10-deacetyl-baccatin III. Such variants include, cephalomannine, xylosyl paclitaxel, 10-deactyl paclitaxel, paclitaxel C, 7-xylosyl baccatin III, 2-debenzoyl baccatin III, 7-xylosyl 10-baccatin III and 2-debenzoyl 10-baccatin III.

Yet another aspect of the invention involves methods of contacting the reduced form of any one of the disclosed oxygenases with carbon monoxide and detecting the carbon monoxide/oxygenase complex.

SEQUENCE LISTINGS

The nucleic acid and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NOS: 1-21 are the nucleic acid sequences of the 21 different respective amplicons generated from the mRNA-reverse transcription-PCR.

SEQ ID NOS: 22-42 are the deduced amino acid sequences of the nucleic acid sequences shown in SEQ ID NOS: 1-21, respectively.

SEQ ID NOS: 43-55 are the full-length nucleic acid sequences of 13 respective oxygenases.

SEQ ID NOS: 56-68 are the deduced amino acid sequences of the nucleic acid sequences shown in SEQ ID NOS: 43-55, respectively.

SEQ ID NOS: 69-72 are the PCR primers used in the RACE protocol.

SEQ ID NOS: 73-80 are PCR primers used to amplify the 21 different amplicons.

SEQ ID NOS: 81-86 are the full-length nucleic acid sequences of 6 respective oxygenases.

SEQ ID NOS: 87-92 are the full-length amino acid sequences of 6 respective oxygenases corresponding to the nucleic acid sequences show in SEQ ID NOS: 81-90, respectively.

SEQ ID NOS: 93 and 94 are PCR primers that were used to clone oxygenases into FastBac-1 vector (Life Technologies).

FIGURES

FIG. 1 shows an outline of early steps of the Taxol biosynthetic pathway illustrating cyclization of geranylgeranyl diphosphate to taxadiene by taxadiene synthase (A), hydroxylation and rearrangement of the parent olefin to taxadien-5α-ol by taxadiene 5α-hydroxylase (B), acetylation by taxadienol-O-acetyl transferase (C), and hydroxylation to taxadien-5α-acetoxy-10β-ol by the taxane 10β-hydroxylase (D). The broken arrow indicates several as yet undefined steps.

FIG. 4 shows P450-specific forward primers that were used for differential display of mRNA-reverse transcription-polymerase chain reaction (DD-RT-PCR). Eight nondegenerate primers were necessary to cover all possible nucleotide sequences coding for the proline, phenylalanine, glycine (PFG) motif. Anchors were designed by Clontech as components of the kit.

Figure 5A:
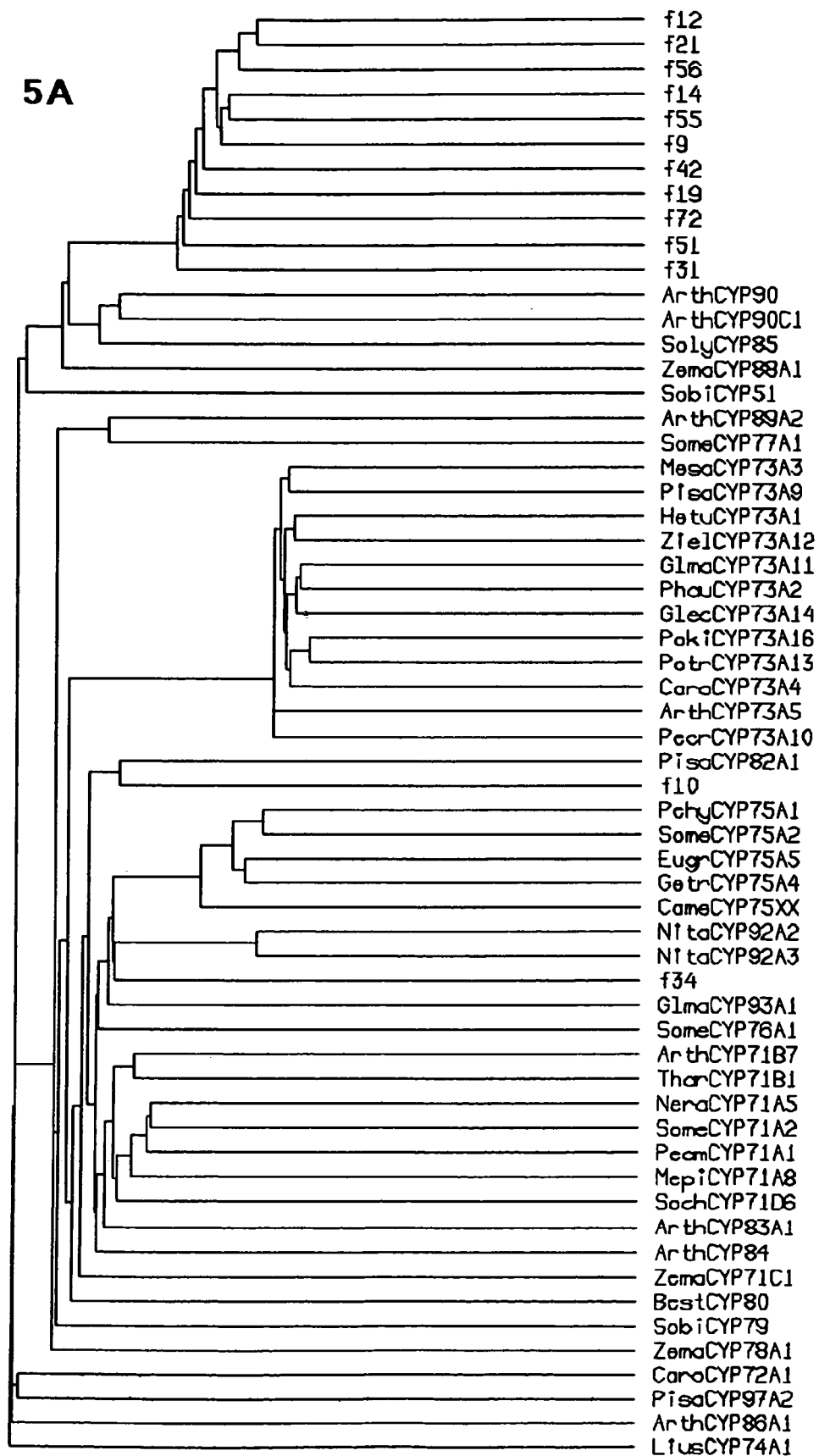
Figure 5C:
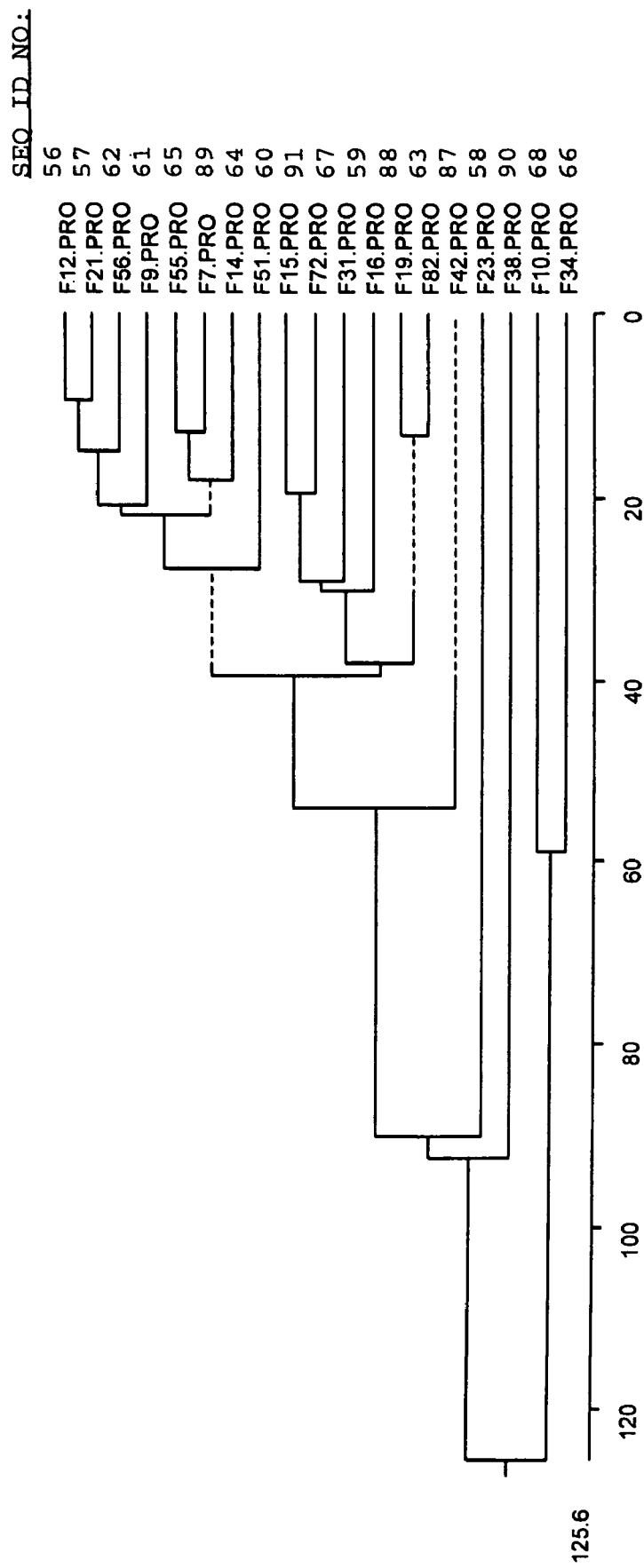

FIGS. 5A and 5D show the relationship between the full-length amino acid sequences of the isolated oxygenases. FIG. 5A is a dendrogram showing peptide sequence relationships between some published, related plant cytochrome P450s and those cloned from *T. cuspidata*. For the published sequences, the first four letters of each name are genus and species abbreviations, CYP is the abbreviation for cytochrome P450, the following two numbers indicate the P450 family, and any additional letters and numbers refer to the subfamily. Cloned sequences from *T. cuspidata* are denoted by "f" followed by a number. The genus and species abbreviations are as follows: Lius—*Linum usitatissimum*; Paar—*Parthenium argentatum*; Caro—*Catharanthus roseus*; Some—*Solanum melongena*; Arth—*Arabidopsis thaliana*; Hetu—*Helianthus tuberosus*; Ziel—*Zinnia elegans*; Poki—*Populus kitamkensis*; Glma—*Glycine max*; Phau—*Phaseolus aureus*; Glec—*Glycyrrhiza echinata*; Mesa—*Medicago sativa*; Pisa—*Pisum sativum*; Pecr—*Petroselinum crispum*; Zema—*Zea mays*; Nita—*Nicotiana tabacum*; Eugr—*Eustoma grandiflorum*; Getr—*Gentiana triflora*; Peam—*Persea americana*; Mepi—*Mentha piperita*; Thar—*Thlaspi arvense*; Best—*Berberis stolonifera*; Soly—*Solanum lycopersicum*; Sobi—*Sorghum bicolor*; Potr—*Populus tremuloides*; Soch—*Solanum chacoense*; Nera—*Nepeta racemosa*; Came—*Campanula medium*; Pehy—*Petunia hybrida*. FIG. 5B shows a pairwise comparison of certain *Taxus* cytochrome P450 clones. FIG. 5C is a dendrogram showing the relationships between the full-length peptide sequences of the disclosed proteins. The dendrogram was created using the Clustral Method. The sequence identity data used as the basis of the dendrogram was created using the Sequence Distance function of the Megalign program of the lasergene (Version 99) package from DNAStar™. FIG. 5D is a similarity/identity table. The sequence identity data was generated using the same program as that used for generating the dendrogram shown in FIG. 5C and the similarity data was generated using the Olddistance function of GCG™ (version GCG10).

Figures 6A, 6B, 6C:
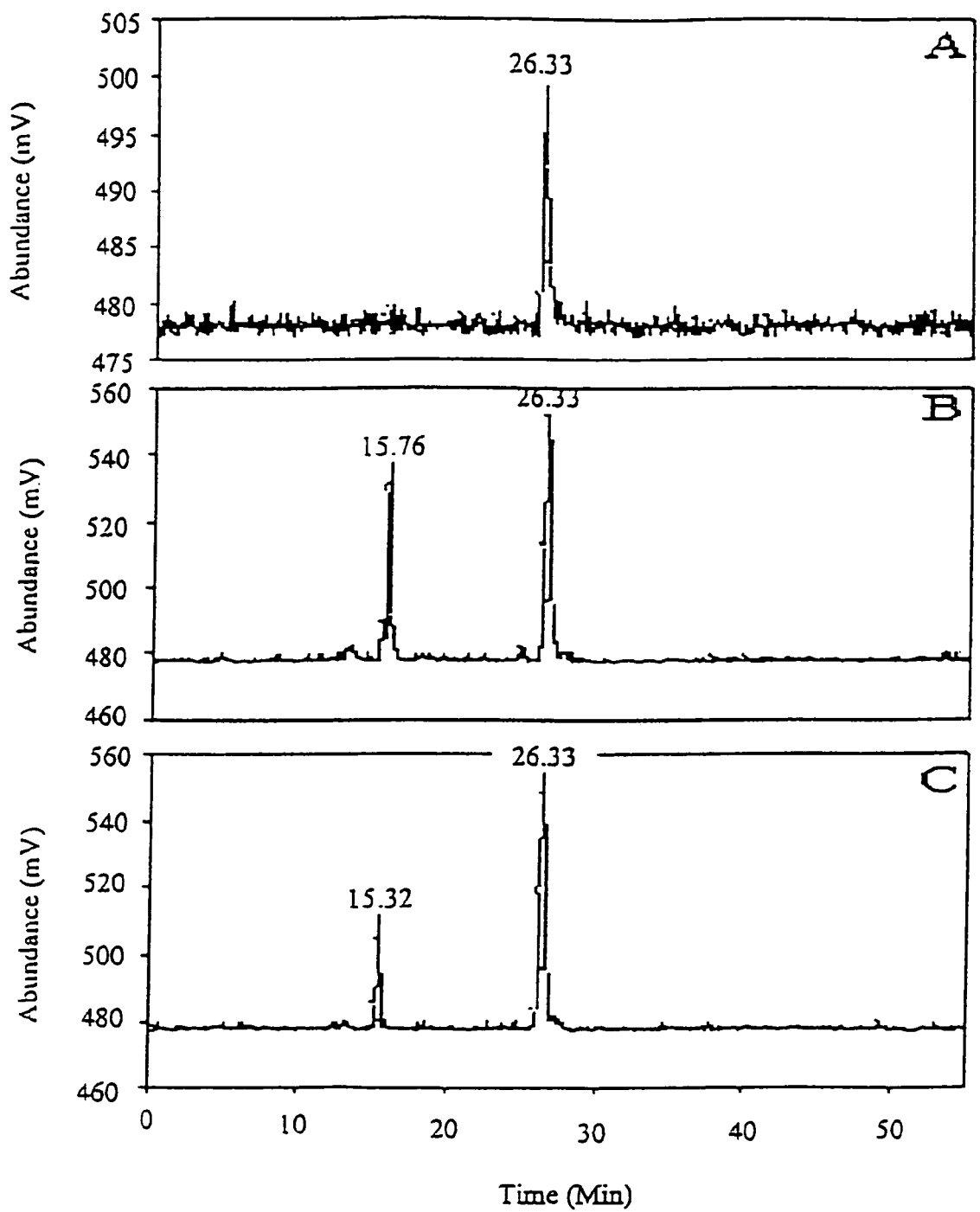
Figures 6D, 6E:
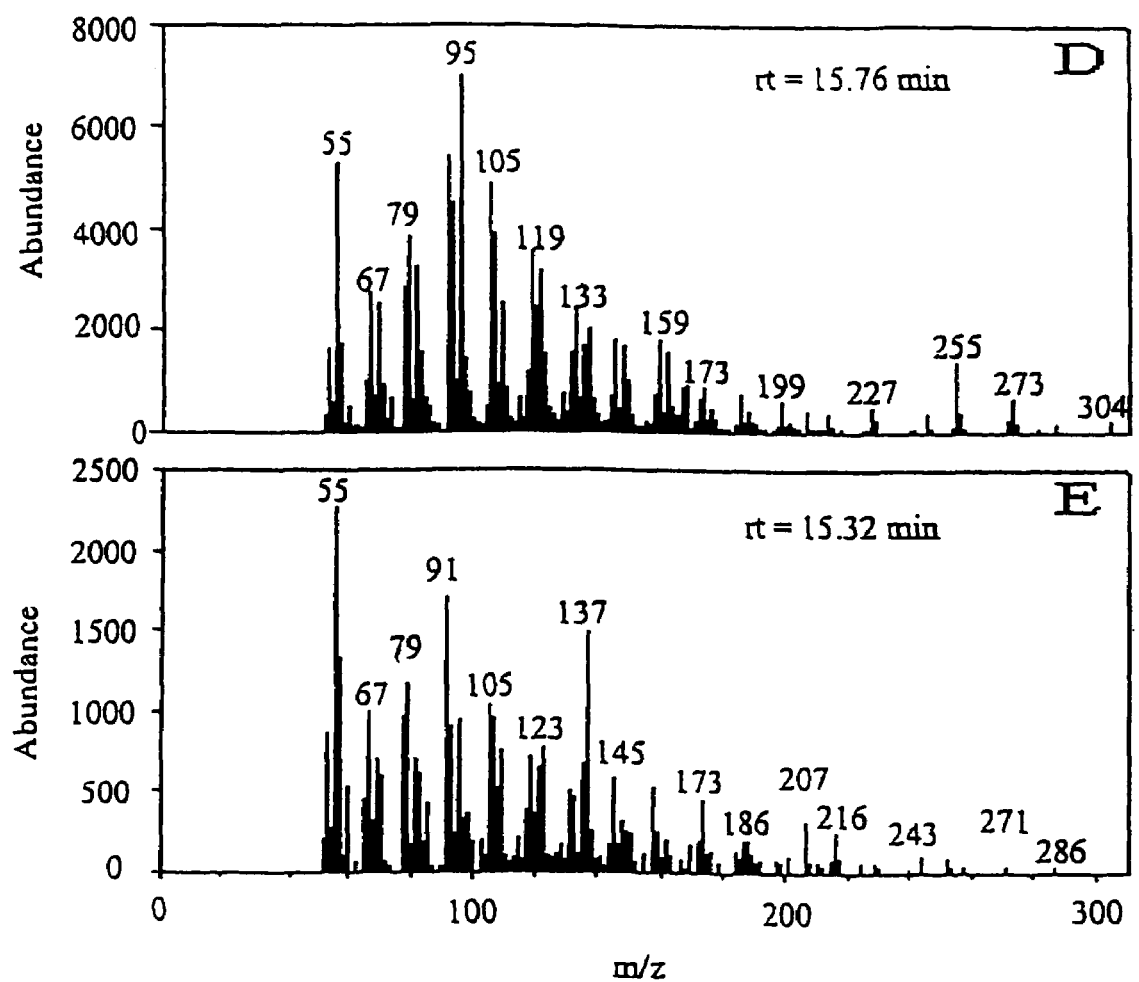

FIGS. 6A-6E show a reversed-phase HPLC radio-trace illustrating the conversion of [20-$^3$H$_2$]taxa-4(20),11(12)-dien-5α-ol to more polar products by yeast transformants expressing *Taxus cuspidata* P450 genes and mass spectrum results. FIG. 6A shows the HPLC radio-trace of the authentic substrate [20-$^3$H$_2$]taxa-4(20),11(12)-dien-5α-ol. FIGS. 6B and 6C show the HPLC radio-trace of the substrate [20-$^3$H$_2$] taxa-4(20),11(12)-dien-5α-ol (26.33 min) and more polar products (retention ~15 min) obtained after incubation with yeast transformed with clones F12 (SEQ ID NO: 43) and F9 (SEQ ID NO: 48), respectively. FIGS. 6D and 6E show the mass spectrum of the products (at 15.76 minutes and at 15.32 minutes, respectively) formed during the incubation of taxadien-5α-ol with yeast transformants expressing clones F12 and F9, respectively. Cytochrome P450 clones F14 (SEQ ID NO: 51) and F51 (SEQ. ID NO: 47) behaved similarly in yielding diol products.

Figure 7:
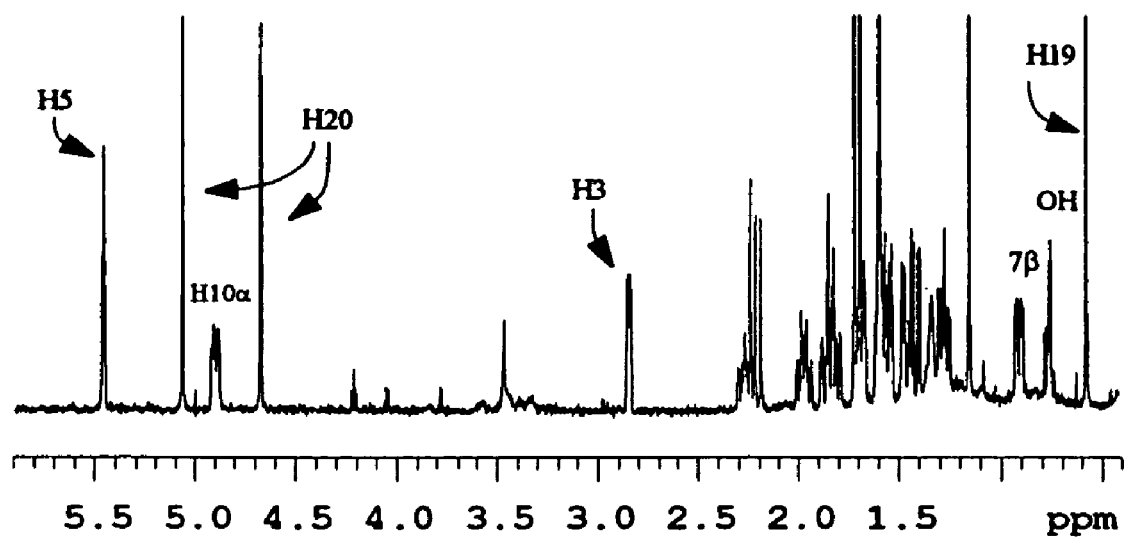

FIG. 7 shows a 500 MHz proton NMR spectrum of the taxadien-diol monoacetate in benzene-d$_6$.

Figure 8:
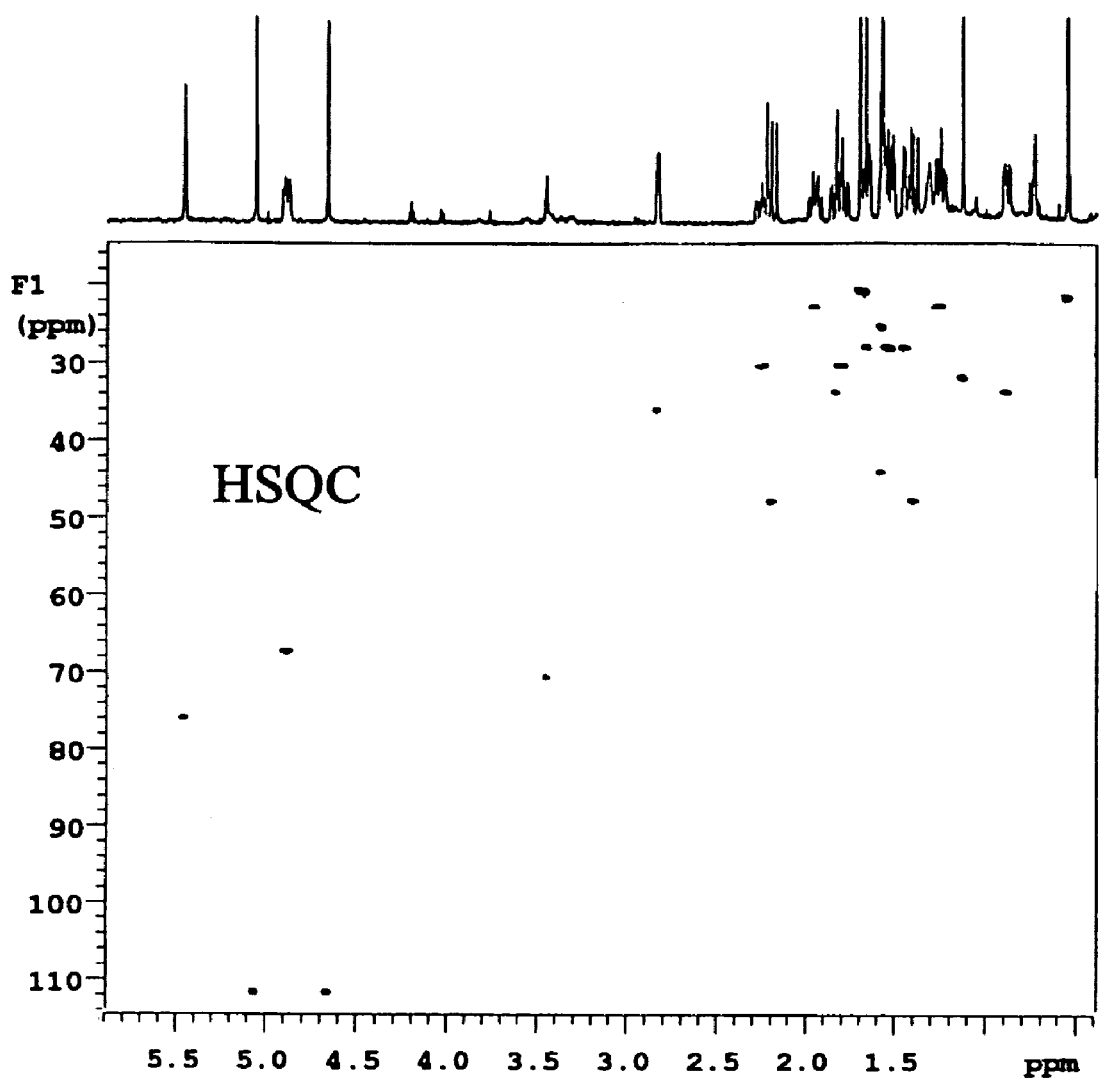

FIG. 8 shows a $^1$H detected two-dimensional heteronuclear single quantum coherence (HSQC) NMR spectrum of the unknown taxadien-diol monoacetate.

Figures 9A, 9B:
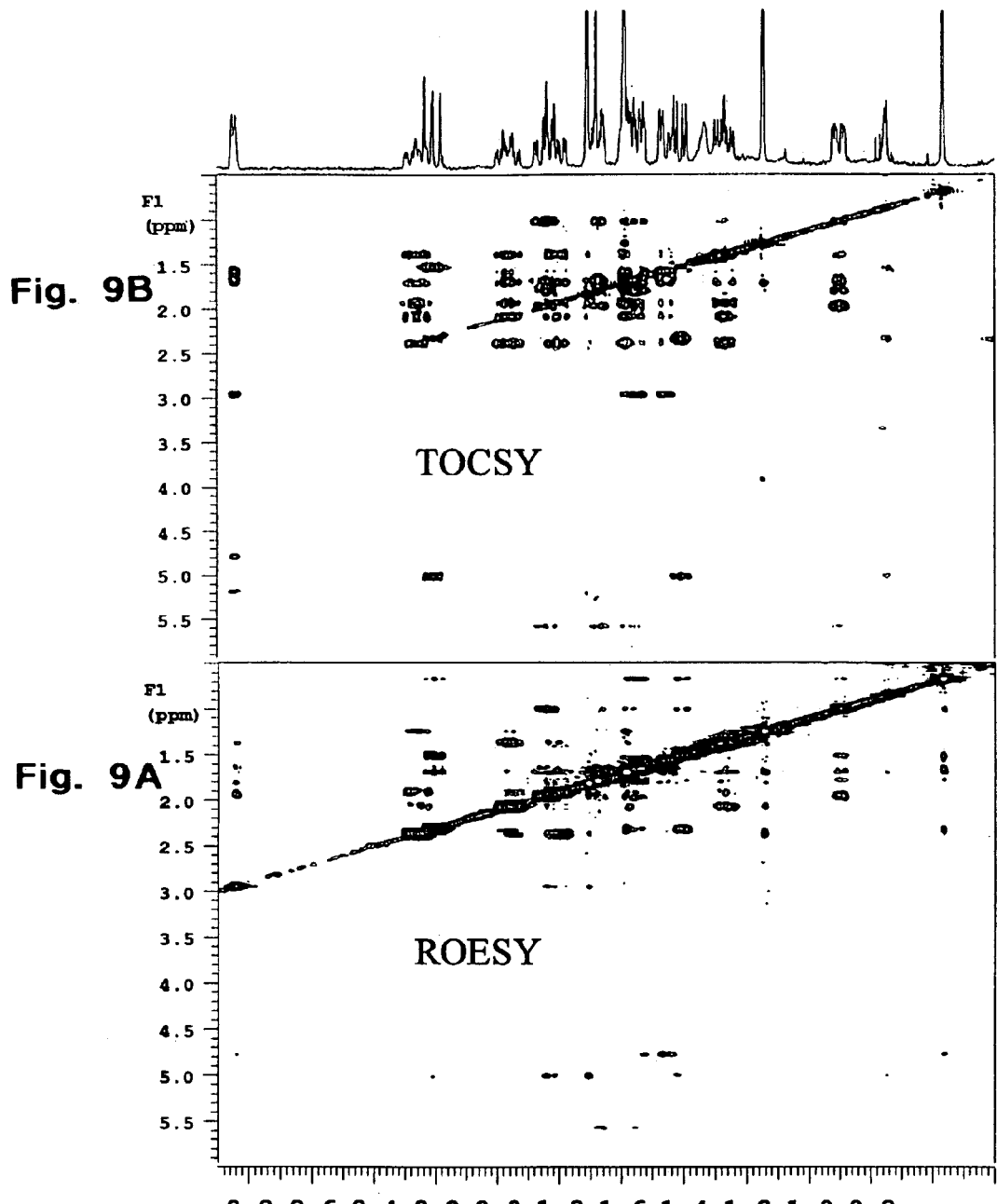
Figures 10A, 10B, 10C, 10D, 10E:
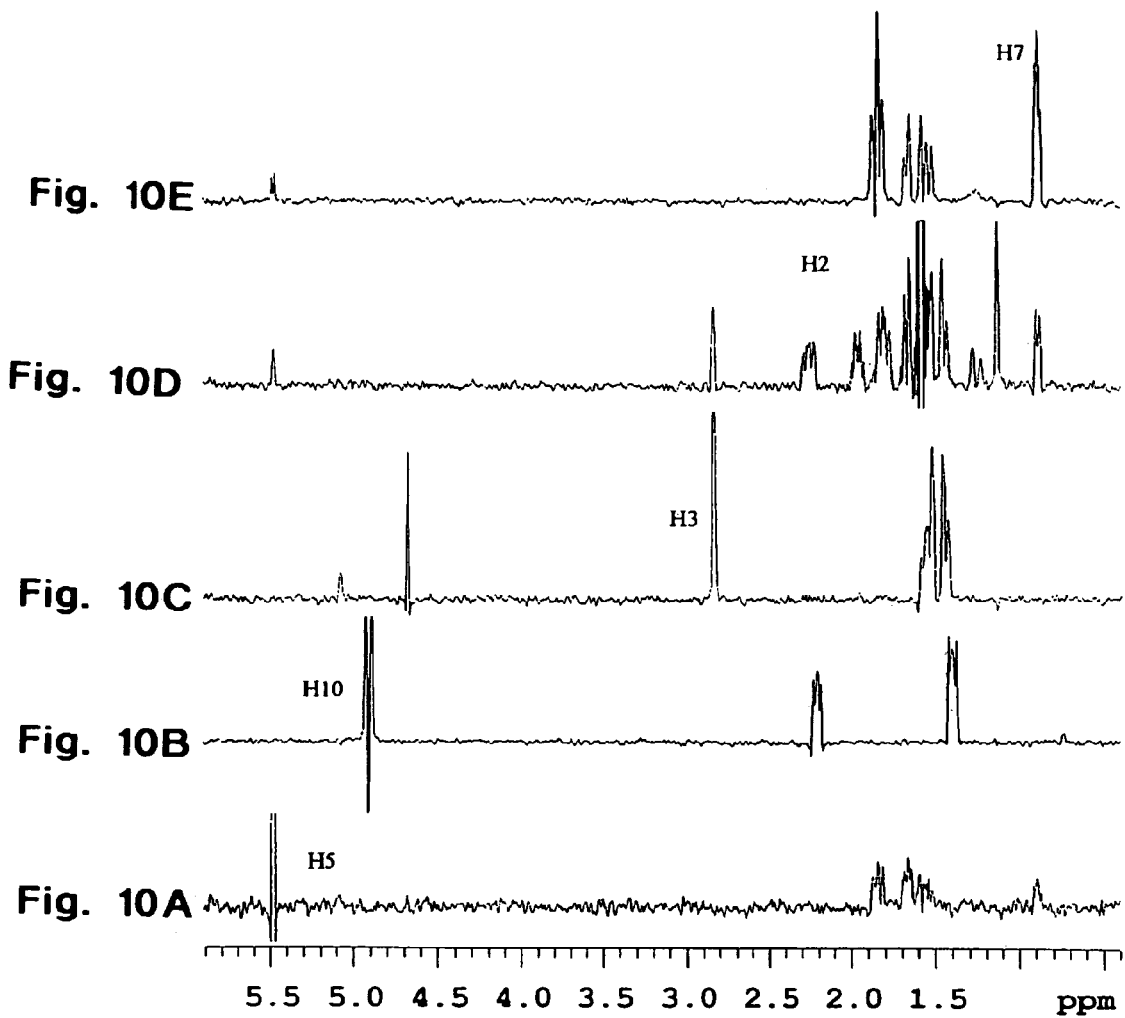

FIGS. 9A and 9B show a $^1$H-$^1$H two-dimensional homonuclear rotating frame NMR of the diol monoacetate. FIG. 9A is a total correlation spectrum (TOSCY) and FIG. 9B is a rotating frame n.O.e. (ROESY).

FIGS. 10A-10E show slices from the TOCSY spectrum taken along the F2, directly detected, axis.

FIGS. 11A-11E show slices from the ROESY spectrum taken along the F2, directly detected, axis.

DETAILED DESCRIPTION

Explanations

Host cell: A "host cell" is any cell that is capable of being transformed with a recombinant nucleic acid sequence. For example, bacterial cells, fungal cells, plant cells, insect cells, avian cells, mammalian cells, and amphibian cells.

Taxoid: A "taxoid" is a chemical based on the Taxane ring structure as described in Kingston et al., *Progress in the Chemistry of Organic Natural Products*, Springer-Verlag, 1993.

Isolated: An "isolated" biological component (such as a nucleic acid or protein or organelle) is a component that has been substantially separated or purified away from other biological components in the cell of the organism in which the component naturally occurs, i.e., other chromosomal and extra-chromosomal DNA, RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Orthologs: An "ortholog" is a gene encoding a protein that displays a function similar to a gene derived from a different species.

Homologs: "Homologs" are multiple nucleotide sequences that share a common ancestral sequence and that diverged when a species carrying that ancestral sequence split into at least two species.

Purified: The term "purified" does not require absolute purity; rather, it is intended as a relative term. Thus, for example, a purified enzyme or nucleic acid preparation is one in which the subject protein or nucleotide, respectively, is at a higher concentration than the protein or nucleotide would be in its natural environment within an organism. For example, a preparation of an enzyme can be considered as purified if the enzyme content in the preparation represents at least 50% of the total protein content of the preparation.

Vector: A "vector" is a nucleic acid molecule as introduced into a host cell, thereby producing a transformed host cell. A vector may include nucleic acid sequences, such as an origin of replication, that permit the vector to replicate in a host cell. A vector may also include one or more screenable markers, selectable markers, or reporter genes and other genetic elements known in the art.

Transformed: A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, and particle-gun acceleration.

DNA construct: The term "DNA construct" is intended to indicate any nucleic acid molecule of cDNA, genomic DNA, synthetic DNA, or RNA origin. The term "construct" is intended to indicate a nucleic acid segment that may be single- or double-stranded, and that may be based on a complete or partial naturally occurring nucleotide sequence encoding one or more of the oxygenase genes of the present invention. It is understood that such nucleotide sequences include intentionally manipulated nucleotide sequences, e.g., subjected to site-directed mutagenesis, and sequences that are degenerate as a result of the genetic code. All degenerate nucleotide sequences are included within the scope of the invention so long as the oxygenase encoded by the nucleotide sequence maintains oxygenase activity as described below.

Recombinant: A "recombinant" nucleic acid is one having a sequence that is not naturally occurring in the organism in which it is expressed, or has a sequence made by an artificial combination of two otherwise-separated, shorter sequences. This artificial combination is accomplished often by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Specific binding agent: A "specific binding agent" is an agent that is capable of specifically binding to the oxygenases of the present invention, and may include polyclonal antibodies, monoclonal antibodies (including humanized monoclonal antibodies) and fragments of monoclonal antibodies such as Fab, F(ab')$_2$, and Fv fragments, as well as any other agent capable of specifically binding to the epitopes on the proteins.

cDNA (complementary DNA): A "cDNA" is a piece of DNA lacking internal, non-coding segments (introns) and regulatory sequences that determine transcription. cDNA is synthesized in the laboratory by reverse transcription from messenger RNA extracted from cells.

ORF (open reading frame): An "ORF" is a series of nucleotide triplets (codons) coding for amino acids without any termination codons. These sequences are usually translatable into respective polypeptides.

Operably linked: A first nucleic acid sequence is "operably linked" with a second nucleic acid sequence whenever the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Probes and primers: Nucleic acid probes and primers may readily be prepared based on the amino acid sequences and nucleic acid sequences provided by this invention. A "probe" comprises an isolated nucleic acid attached to a detectable label or reporter molecule. Typical labels include radioactive isotopes, ligands, chemiluminescent agents, and enzymes. Probes are typically shorter in length than the sequences from which they are derived (i.e., cDNA or gene sequences). For example, the amplicons shown in SEQ ID NOS: 1-21 and fragments thereof can be used as probes. One of ordinary skill in the art will appreciate that probe specificity increases with the length of the probe. For example, a probe can contain less than 800 bp, 700 bp, 600 bp, 500 bp, 400 bp, 300 bp, 200 bp, 100 bp, or 50 bp of constitutive bases of any of the oxygenase encoding sequences disclosed herein. Methods for labeling and guidance in the choice of labels appropriate for various purposes are discussed, e.g., in Sambrook et al. (eds.), *Molecular Cloning: A Laboratory Manual* 2nd ed., vols. 1-3, Cold Spring Harbor Laboratory Press, Cold Spring Harbor, N.Y., 1989, and Ausubel et al. (eds.) *Current Protocols in Molecular Biology*, Greene Publishing and Wiley-Interscience, New York (with periodic updates), 1987.

"Primers" are short nucleic acids, preferably DNA oligonucleotides 10 nucleotides or more in length. A primer may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR), or other nucleic-acid amplification methods known in the art.

Methods for preparing and using probes and primers are described, for example, in references such as Sambrook et al. (eds.), *Molecular Cloning: A Laboratory Manual*, 2nd ed., vols. 1-3, Cold Spring Harbor Laboratory Press, Cold Spring Harbor, N.Y., 1989; Ausubel et al. (eds.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with the length of the probe or primer. Thus, for example, a primer comprising 20 consecutive nucleotides will anneal to a target with higher specificity than a corresponding primer of only 15 nucleotides in length. Thus, in order to obtain greater specificity, probes and primers may be selected that comprise, for example, 10, 20, 25, 30, 35, 40, 50 or more consecutive nucleotides.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237-244, 1988; Higgins & Sharp, *CABIOS* 5:151-153, 1989; Corpet et al., *Nucleic Acids Research* 16:10881-10890, 1988; Huang, et al., *Computer Applications in the Biosciences* 8:155-165, 1992; and Pearson et al., *Methods in Molecular Biology* 24:307-331, 1994. Altschul et al., *J. Mol. Biol.* 215:403-410, 1990, presents a detailed consideration of sequence-alignment methods and homology calculations.

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ program is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 45%, at least 50%, at least 60%, at least 80%, at least 85%, at least 90%, or at least 95% sequence identity.

As mentioned above, 'Sequence identity' can be determined by using an alignment algorithm such as Blast™ (available at the National Center for Biotechnology Information [NCBI]). A first nucleic acid is "substantially similar" to a second nucleic acid if, when optimally aligned (using the default parameters provided at the NCBI wesite) with the other nucleic acid (or its complementary strand), there is nucleotide sequence identity in at least about, for example, 50%, 75%, 80%, 85%, 90% or 95% of the nucleotide bases. Sequence similarity can be determined by comparing the nucleotide sequences of two nucleic acids using the BLAST™ sequence analysis software (blastn) available from NCBI. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if they show sequence identity of at least about 75%-90% or greater when optimally aligned and compared using BLAST software (blastp) using default settings.

Oxygenase activity: Enzymes exhibiting oxygenase activity are capable of directly incorporating oxygen into a substrate molecule. Oxygenases can be either dioxygenases, in which case the oxygenase incorporates two oxygen atoms into the substrate; or, monooxygenases, in which only one oxygen atom is incorporated into the primary substrate to form a hydroxyl or epoxide group. Thus, monooxygenases are referred to sometimes as "hydroxylases." Taxoid oxygenases are a subset of oxygenases that specifically utilize taxoids as substrates.

Oxygenases: Oxygenases are enzymes that display oxygenase activity as described supra. However, all oxygenases do not recognize the same substrates. Therefore, oxygenase enzyme-activity assays may utilize different substrates depending on the specificity of the particular oxygenase enzyme. One of ordinary skill in the art will appreciate that the spectrophotometry-based assay described below is a representative example of a general oxygenase activity assay, and that direct assays can be used to test oxygenase catalysis directed towards different substrates.

II. Characterization of Oxygenases

A. Overview of Experimental Procedures

Biochemical studies have indicated that at least the first five oxygenation steps of the Taxol pathway are catalyzed by cytochrome P450 hydroxylases (the remaining three oxygenations are also likely catalyzed by cytochrome P450 enzymes), and that these are slow steps of the reaction pathway and, thus, important candidates for cDNA isolation for the purpose of over-expression in relevant producing organisms to increase Taxol yields (Croteau et al., *Curr. Topics Plant Physiol*. 15:94-104, 1995; and Hezari et al., *Planta Med*. 63:291-295, 1997). Protein purification of cytochrome P450 enzymes from *Taxus* microsomes (Hefner et al., *Methods Enzymol*. 272:243-250, 1996), as a basis for cDNA cloning, was not performed because the number of P450 species present, and their known similarity in physical properties (Mihaliak et al., *Methods Plant Biochem*. 9:261-279, 1993), would almost certainly have prevented bringing the individual proteins to homogeneity for amino acid microsequencing.

Therefore, a strategy based on the differential display of mRNA-reverse transcription-PCR (DD-RT-PCR) was used for isolating transcriptionally active cytochrome P450s in *Taxus* cells, which previous biochemical studies had shown to undergo substantial up-regulation of the Taxol pathway 16 hours after induction with methyl jasmonate (Hefner et al., *Arch. Biochem. Biophys*. 360:62-74, 1998). Differential display experimental schemes allow for the identification of mRNA species that are up-regulated in response to certain stimulus. Generally, one set of samples is not treated with the stimulant, and a second set of samples is treated with the stimulant. Subsequently, the mRNA from both groups is isolated and amplified. The mRNA of interest is identified by comparing the mRNA from the stimulated and unstimulated samples. The mRNA that is present only in the stimulated sample appears to represent genes that are activated upon stimulation.

In the experiments described below, mRNA from an untreated cell culture was compared to the mRNA from a culture that had been induced with methyl jasmonate for 16 hours. In order to obtain predominantly induced cytochrome P450 sequences, forward primers were designed based on a conserved proline, phenylalanine, glycine (PFG) motif in plant cytochrome P450 genes. The use of primers directed towards the (PFG) motif in conjunction with the DD-RT-PCR-based strategy revealed roughly 100 differentially expressed species, and the sequences of 100 of these were obtained and analyzed. Of these, 39 represented PCR products containing a cytochrome P450-type sequence. Analysis of these sequences revealed that the C-terminus from 21 different and unique cytochrome P450 genes had been isolated. The 21 nucleic acid sequences amplified (amplicons) and identified as regions encoding oxygenases are shown in SEQ ID NOS: 1-21, respectively.

Twelve amplicons were labeled and used as hybridization probes to screen the methyl jasmonate-induced *T. cuspidata* cell cDNA library. Screening the *T. cuspidata* library allowed identification of nine full-length clones. Four additional clones, which were truncated at the 5'-terminus, were obtained in full-length form using a 5'-RACE (Rapid analysis of cDNA ends) method to acquire the missing 5'-sequences. Thus, the initial use of the amplicons, described above, has allowed for the identification of thirteen full-length oxygenases (SEQ ID NOS: 43-55, respectively). Subsequently, various molecular techniques were used to identify an additional 10 full-length cDNAs (SEQ ID NOS: 81-86, respectively) and their corresponding amino acid sequences (SEQ ID NOS: 87-92, respectively).

The full-length oxygenase clones identified through the use of the amplicon-based probes can then be cloned into prokaryotic-based and eukaryotic-based expression systems. Once expressed, the functional competence of the resulting oxygenases can be assessed using the spectrophotometric assay described below.

The clones that are found to be active using the spectrophotometric assay are at a minimum useful for detecting carbon monoxide. Additionally, in the examples provided below, several of the full-length oxygenase-encoding sequences are shown to have in situ oxygenase activity towards taxoids when expressed in *Saccharomyces cerevisiae* and baculovirus-*Spodoptera* cells.

Oxygenases produced by cloned full-length oxygenase-encoding sequences also can be tested for the ability to oxygenate taxoid substrates in vivo. This can be done by feeding taxoid intermediates to transgenic cells expressing the cloned oxygenase-encoding sequences.

B. Cloning of Oxygenases

As described supra, a DD-RT-PCR scheme was used for the isolation of transcriptionally active cytochrome P450s in *Taxus* cells, which previously had been shown to undergo substantial up-regulation of the Taxol pathway 16 hours after induction with methyl jasmonate (Hefner et al., *Arch. Biochem. Biophys*. 360:62-74, 1998). Because an increase in the relevant enzyme activities resulted from induction (indicating de novo protein synthesis), mRNA from an untreated cell culture was compared to mRNA from a culture that had been so induced for 16 hours. In order to obtain predominantly induced cytochrome P450 sequences, forward primers were designed based on a conserved motif in plant cytochrome P450 genes. Related strategies have been used with other plants (Schopfer and Ebel, *Mol. Gen. Genet*. 258:315-322, 1998). The proline, phenylalanine, glycine (PFG) motif is a well-conserved region of the heme-binding domain (Durst and Nelson, "Diversity and evolution of plant P450 and P450 reductase," in Durst and O'Keefe (eds.), *Drug Metabolism and Drug Interactions*, Freund, UK, 1995, pp. 189-206). The corresponding codons of this region contain only two degenerate positions; thus, a set of only eight non-degenerate primers was necessary to encompass all sequence possibilities (FIG. 4). This PFG motif is located 200-250 bp upstream of the stop codon, and the length of the 3'-untranslated region should range between 100 and 300 bp. Thus, the length of the expected PCR fragments would be in the 300-550 bp range. This DD-RT-PCR-based strategy revealed roughly 100 differentially expressed species, and the sequences of 100 of these were obtained and analyzed. Of these, 39 represented PCR products containing a cytochrome P450-type sequence. Analysis of these sequences revealed that the C-terminus from 21 different and unique cytochrome P450 genes had been isolated. These DNA fragments (12 thus far) are being used as labeled hybridization probes to screen the methyl jasmonate-induced *T. cuspidata* cell cDNA library. By this means, nine clones have been obtained in full-length form by screening. Four additional clones, which were truncated at the 5'-terminus, were obtained in full-length form using a 5'-RACE (Rapid analysis of cDNA ends) method to acquire the missing 5'-sequences.

C. Sequence Analysis

The full-length oxygenase sequences initially obtained (using 12 partial sequence probes) were compared pairwise. It was shown that a total of 13 unique sequences (showing less than 85% similarity), designated clones F12, F21, F42, F31, F51, F9, F56, F19, F14, F55, F34, F72, and F10, respectively (SEQ ID NOS: 43-55, respectively) were present. Two of the isolated clones, clone F51 (SEQ ID NO: 47) and clone F9 (SEQ ID NO: 48) were not identical to any of the 21 C-terminal fragments originally found by the DD-RT-PCR cloning strategy, bringing the total number of initially identified unique oxygenase genes, and gene fragments, to 23.

The clones obtained also were compared pairwise to all known plant cytochrome P450 oxygenase sequences in the databases (provided at the NCBI website) (FIGS. 5A and 5B) provide a dendrogram of these relationships and a table of pairwise similarity and identity comparisons).

This analysis revealed that 11 of the *Taxus* clones sorted into one cytochrome P450 family. This large group of related clones seems to resemble most closely the CYP90, CYP85, and CYP88 cytochrome P450 families. Some members of these families are known to be involved in terpenoid metabolism [e.g., gibberellin (diterpene, C20) and brassinosteroid (triterpene C30) biosynthesis], suggesting that the cytochrome P450 clones obtained from *Taxus* could be involved in the biosynthesis of the diterpenoid Taxol. Table 1 lists accession numbers of relevant sequences and related information. Outlying clones F10 (SEQ ID NO: 55) and F34 (SEQ ID NO: 53) are related more closely to CYP family 82 (phenylpropanoid metabolism) and CYP family 92 (unknown function), respectively.

After the initial 13 full-length clones were identified, six more were isolated. Thus, the total number of full-length oxygenase clones identified is nineteen. A dendrogram showing the relationship of all of the identified oxygenase clones is provided in FIG. 5C. A table providing both the sequence identity and similarity of the clones is provided in FIG. 5D.

TABLE 1

Closest Relatives to Taxus Cytochrome P450 Sequences

| Family | Description | Clones That Are Similar |
|---|---|---|
| CYP90A1 | *Arabidopsis thaliana* GenEMBL X87367 mRNA (1608 bp); GenEMBL X87368 gene (4937 bp). Szekeres et al., "Brassinosteroids rescue the deficiency of CYP90, a cytochrome P450, controlling cell elongation and de-etiolation in *Arabidopsis*," Cell 85: 171-182 (1996). | F9, F12, F14, F19, F21, F31, F42, F51, F55, F56, and F72 (SEQ ID NOS: 48, 43, 51, 50, 44, 46, 45, 47, 52, 49, and 54, respectively) |
| CYP85 | *Solanum lycopersicum* (tomato) (also *Lycopersicon esculentum*) GenEMBL U54770 (1395 bp). Bishop et al., "The tomato dwarf gene isolated by heterologous transposon tagging encodes the first member of a new family of cytochrome P450," Plant Cell 8: 959-969 (1996). | F9, F12, F14, F19, F21, F31, F42, F51, F55, F56, and F72 (SEQ ID NOS: 48, 43, 51, 50, 44, 46, 45, 47, 52, 49, and 54, respectively) |
| CYP88A1 | *Zea mays* GenEMBL U32579 (1724 bp). Winkler and Helentjaris, "The maize dwarf3 gene encodes a cytochrome P450-mediated early step in gibberellin biosynthesis," Plant Cell 7: 1307-1317 (1995). | F9, F12, F14, F19, F21, F31, F42, F51, F55, F56, and F72 (SEQ ID NOS: 48, 43, 51, 50, 44, 46, 45, 47, 52, 49, and 54, respectively) |
| CYP82A1 | *Pisum sativum* (pea) GenEMBL U29333 (1763 bp). Frank et al., "Cloning of phenylpropanoid pathway P450 monooxygenases expressed in *Pisum sativum*," unpublished. | Outlying Clone F10 (SEQ ID NO: 55) |

TABLE 1-continued

Closest Relatives to Taxus Cytochrome P450 Sequences

| Family | Description | Clones That Are Similar |
|---|---|---|
| CYP82A2 | *Glycine max* (soybean) GenEMBL Y10491 (1757 bp). Schopfer and Ebel, "Identification of elicitor-induced cytochrome P450s of soybean (*Glycine max* L.) using differential display of mRNA," Mol. Gen. Genet. 258: 315-322 (1998). | Outlying Clone F34 (SEQ ID NO: 53) |
| CYP92A2 | *Nicotiana tabacum* (tobacco) GenEMBL X95342 (1628 bp). Czernic et al., "Characterization of hsr201 and hsr215, two tobacco genes preferentially expressed during the hypersensitive reaction provoked by phytopathogenic bacteria," unpublished. | Outlying Clone F34 (SEQ ID NO: 53) |

D. Functional Expression

Functional cytochrome P450 expression can be obtained by using the pYeDP60 plasmid in yeast (*Saccharomyces cerevisiae*) engineered to co-express one or the other of a cytochrome P450 reductase from *Arabidopsis thaliana*; the plant-derived reductase is important for efficient electron transfer to the cytochrome (Pompon et al., *Methods Enzymol.* 272:51-64, 1999).

Since a functional P450 cytochrome, in the appropriately reduced form, will bind competently to carbon monoxide and give a characteristic CO-difference spectrum (Omura and Sato, *J. Biol. Chem.* 239:2370-2378, 1964), a spectrophotometric means for assessing, and quantitatively estimating, the presence of functional recombinant cytochrome P450 in transformed yeast cells by in situ (in vivo) measurement was developed. CO-sensor of the 19 full-length cytochrome P450 clones from *Taxus*, thus far obtained, ten have yielded detectable CO-difference spectra (Table 2). It is expected that cytochrome P450 clones that do not yield reliable expression in *S. cerevisiae* can be transferred to, expressed in, and confirmed by CO-difference spectrum utilizing alternative prokaryotic and eukaryotic systems. These alternative expression systems for cytochrome P450 genes include the yeast *Pichia pastoris*, for which expression vectors and hosts are commercially available (Invitrogen, Carlsbad, Calif.), as well as established *E. coli* and baculovirus-insect cell systems for which general expression procedures have been described (Barnes, *Methods Enzymol.* 272:1-14, 1996; Gonzalez et al., *Methods Enzymol.* 206:93-99, 1991; Lee et al., *Methods Enzymol.* 272:86-98, 1996; and Lupien et al., *Arch. Biochem. Biophys.* 368:181-192, 1999).

Clones that prove to be capable of binding to CO are useful at least for detecting CO in various samples. Further testing of the recombinantly expressed clones may prove that they are additionally useful for adding one or more oxygen atoms to taxoid substrates.

E. In vivo Assays of Yeast Cells Expressing Recombinant Oxygenases

1. Use of substrates [20-$^3$H$_3$]taxa-4(5),11(12)-diene or [20-$^3$H$_2$taxa-4(20,11(12)-dien-5α-ol Transformed yeast cells that functionally express a recombinant cytochrome P450 gene from *Taxus* (by CO-difference spectrum) can be tested in vivo for their ability to oxygenate (hydroxylate or epoxidize) taxoid substrates fed exogenously to the cells, thereby eliminating the need for microsome isolation for preliminary in vitro assays.

Accordingly, several clones of the available full-length clones were expressed in induced yeast host cells. These cells were fed [20-$^3$H$_3$]taxa-4(5),11(12)-diene or [20-$^3$H$_2$]taxa-4(20,11(12)-dien-5α-ol in separate incubations and compared to untransformed controls similarly fed (and that were shown to be inactive with taxoid substrates). The extracts resulting from these incubations were analyzed by radio-HPLC, and the clones that yielded a product are shown below in Table 2.

Representative HPLC traces are shown in FIGS. 6A-6C. Representative GC-MS (gas chromatography-mass spectrometry) analyses of the products from an incubation are shown in FIGS. 6D and 6E. The results shown in FIGS. 6A-6E confirm that two distinctly different taxadien-diols derived from taxadien-5α-ol were formed, one yielding the expected parent ion at $P^+$=m/z 304, and the other less stable to the conditions of the analysis in losing water readily to yield the highest mass ion at m/z 286 ($P^+$—$H_2O$).

2. Use of substrate [20-$^3$H$_2$]taxa-4(20), 11(12)-dien-5α-yl acetate

Transformed yeast cells that functionally express a recombinant cytochrome P450 gene from *Taxus* (by CO-difference spectrum) were tested in vivo for their ability to oxygenate (hydroxylate or epoxidize) taxoid substrates fed exogenously, thereby eliminating the need for microsome isolation for such a preliminary in vitro assay. The clones indicated in Table 2, below, were induced in yeast host cells that were fed [20-$^3$H$_2$] taxa-4(20),11(12)-dien-5α-yl acetate in separate incubations and compared to untransformed controls similarly fed (and that were shown to be inactive with taxoid substrates). The ether extracts resulting from these incubations were analyzed by radio-HPLC. Several clones converted the taxadienyl-5α-yl acetate substrate to a more polar product.

TABLE 2

| Full-length name (SEQ ID NO: nt/aa) | Probe name (SEQ ID NO: nt/aa) | CO diff. spec. | assayed with | product identified HPLC peak |
|---|---|---|---|---|
| F12 | aa1 | + | Taxadiene | No |
| * 43/56 | 11/32 | | Taxadien5αol | ++ |
| | | | Taxadienyl Ac | ++ |
| F21 | cb1 | + | Taxadiene | No |
| * 44/57 | 10/31 | | Taxadien5αol | + |
| | | | Taxadienyl Ac | No |
| F31 | ab2 | + | Taxadiene | No |
| * 46/59 | 1/22 | | Taxadien5αol | No |
| | | | Taxadienyl Ac | No |
| F42 | ai2 | − | Taxadiene | No |
| * 45/58 | 5/26 | | Taxadien5αol | No |
| F51 | Lib. Screen | + | Taxadiene | No |
| * 47/60 | | | Taxadien5αol | ++ |
| | | | Taxadienyl Ac | ++ |

TABLE 2-continued

| Full-length name (SEQ ID NO: nt/aa) | Probe name (SEQ ID NO: nt/aa) | CO diff. spec. | assayed with | product identified HPLC peak |
|---|---|---|---|---|
| F72 | cm2 | + | Taxadiene | No |
| * 54/67 | 19/40 | | Taxadien5α ol | + |
| | | | Taxadienyl Ac | + |
| F82 81/87 | dl1 20/41 | − | Taxadiene | No |
| | | | Taxadien5α ol | + |
| | | | Taxadienyl Ac | ++ |
| F9 * 48/61 | Lib. Screen | + | Taxadiene | No |
| | | | Taxadien5α ol | + |
| | | | Taxadienyl Ac | +/− |
| F56 * 49/62 | el2 8/29 | − | Taxadiene | No |
| | | | Taxadien5α ol | No |
| F14 * 51/64 | ea1 13/34 | +++ | Taxadiene | No |
| | | | Taxadien5α ol | ++ |
| | | | Taxadienyl Ac | ++ |
| F19 * 50/63 | ds1 14/35 | − | Taxadiene | No |
| | | | Taxadien5α ol | No |
| F55 * 52/65 | cf2 6/27 | − | Taxadiene | No |
| | | | Taxadien5α ol | No |
| F16 82/88 | ae1 2/23 | +++ | Taxadiene | No |
| | | | Taxadien5α ol | ++ |
| | | | Taxadienyl Ac | ++ |
| F7 83/89 | cj1 7/28 | − | Taxadiene | No |
| | | | Taxadien5α ol | ++ |
| | | | Taxadienyl Ac | ++ |
| F23 84/90 | di1 15/36 | − | Taxadiene | No |
| | | | Taxadien5α ol | No |
| F10 * 55/68 | ba1 17/38 | + | Taxadiene | No |
| | | | Taxadien5α ol | No |
| F34 * 53/66 | du1 | ++ | Taxadiene | No |
| | | | Taxadien5α ol | No |
| F15 85/91 | df 12/33 | | | |
| F38 86/92 | ad6 16/37 | | | |

Additional testing of the clone F14 (SEQ ID NO: 64) metabolite was conducted. The metabolite isolated by HPLC was subjected to GC-MS analysis and shown to possess a retention time (compared to the starting material) and mass spectrum that were consistent with respective data obtained from a taxadien-diol monoacetate [the parent ion (P$^+$) was observed at m/z 346 (taxadienyl acetate (MW=330) plus O) with diagnostic ions at m/z 328 (P$^+$—H$_2$O), 313 (P$^+$—H$_2$O—CH$_3$), 286 (P$^+$—CH$_3$COOH), 271 (P$^+$—CH$_3$COOH—CH$_3$), 268 (P$^+$—CH$_3$COOH—H$_2$O) and 253 (P$^+$—CH$_3$COOH—CH$_3$—H$_2$O)].

Preparative-scale incubations of the transformed yeast harboring clone F14 (SEQ ID NO: 51), with the taxadien-5α-yl acetate substrate, yielded the HPLC-based isolation of about 100 μg of the unknown diol monoacetate (>97% purity by GC) for NMR analysis. Since all of the $^1$H resonances of taxadien-4(20),11(12)-dien-5α-ol (and of the acetate ester) had been assigned previously (Hefner et al., *Chem. and Biol.* 3:479-489, 1996), elucidation of the structure of the unknown diol monoacetate was accomplished by $^1$H detection experiments (sample-size-limited direct $^{13}$C measurements).

The $^1$H-NMR spectrum is illustrated in FIG. 7, and Table 3, below, lists the complete $^1$H assignments along with their respective one-carbon correlated $^{13}$C assignments as determined indirectly from heteronuclear single quantum coherence (HSQC; FIG. 8). The assignments are consistent with those of other known taxadien monool and diol derivatives. For example, chemical shifts for C5 (δ 75.9, C5; δ 5.47, H5) and C10 (δ 67.2, C10; δ 4.9 H10) are assigned as oxy-methines. The shifts for C20 (δ 111.6, C20; δ 5.07, H20, exo; δ 4.67, H20, endo) are consistent with the exocyclic methylene observed in other taxa-4(20),11(12)-dienes. Other characteristic shifts are observed for H7α (δ 1.84), H19 methyl (δ 0.56), H3 (δ 2.84), and the gem-dimethyls H16 (δ 1.14, exo) and H17 (δ 1.59, endo).

TABLE 3

Figure 1:
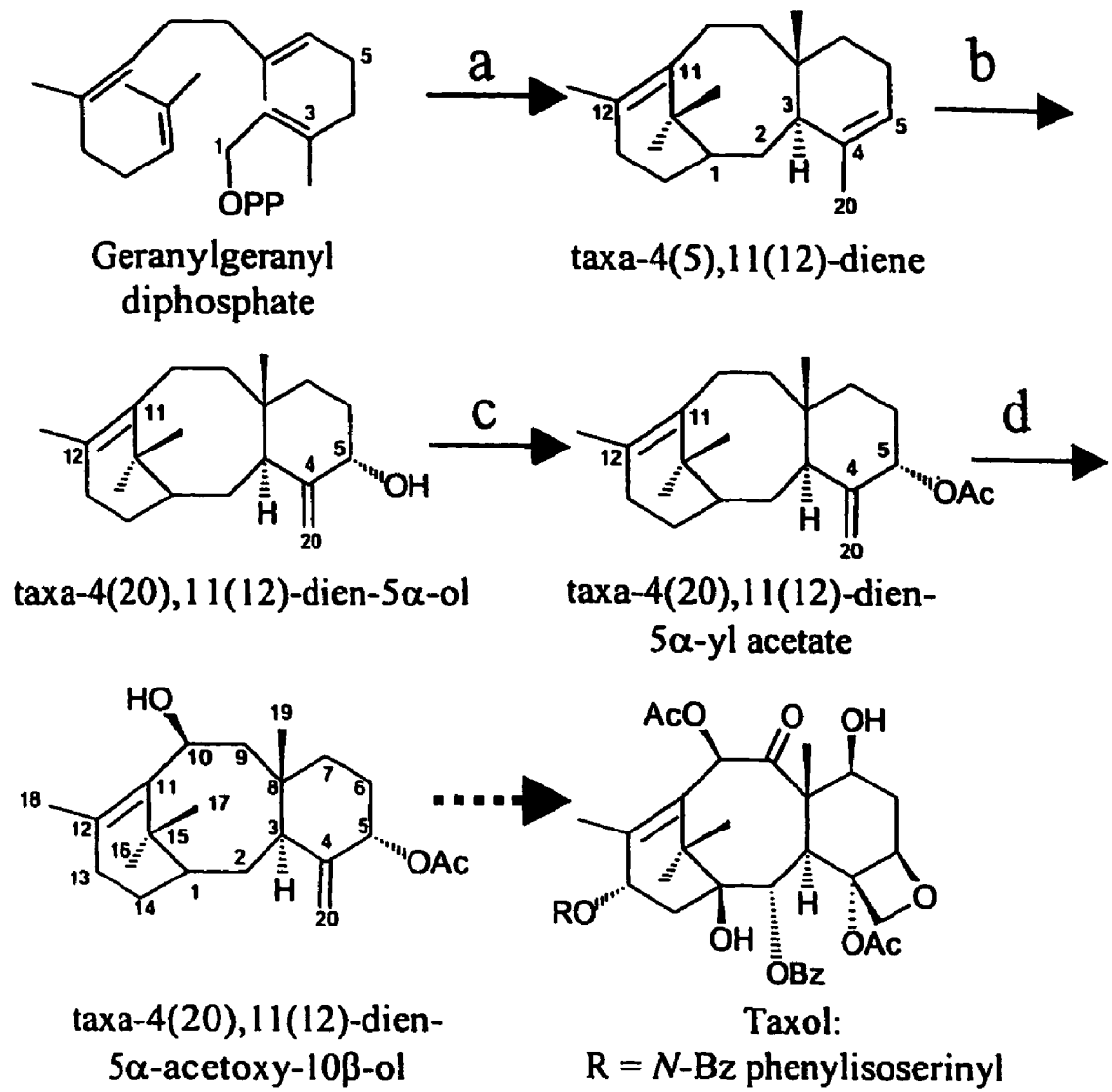
Figure 2:
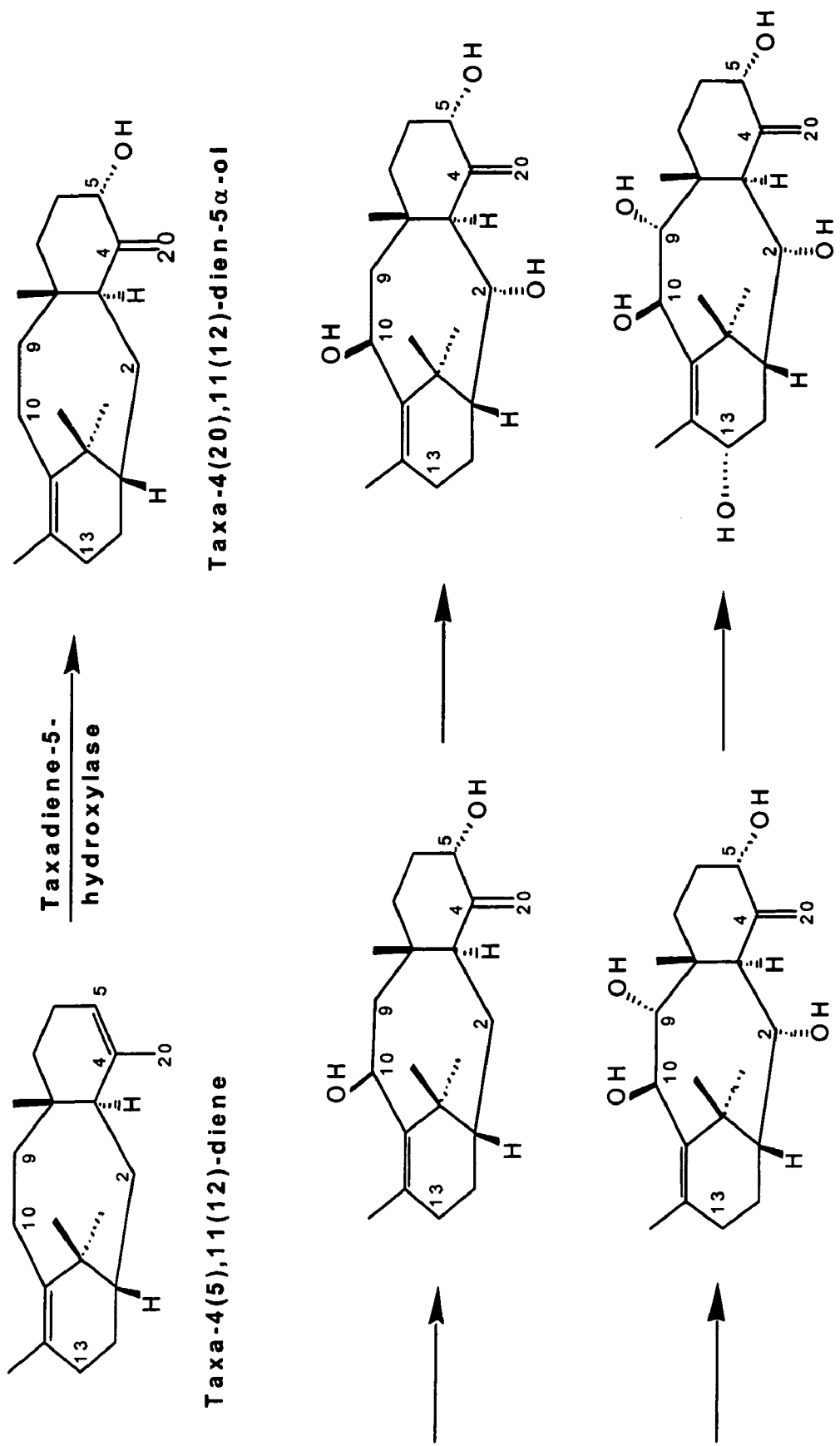
FIG. 2 shows the proposed sequence for the hydroxylation of taxa-4(5),11(12)-diene to the level of a pentaol based on the relative abundances of naturally occurring taxoids. The reactions are catalyzed by cytochrome P450 oxygenases.
Figure 3:
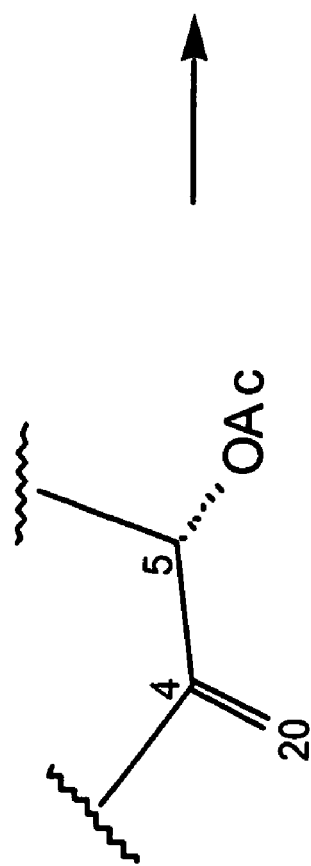
FIG. 3 shows a possible mechanism for the construction of the oxetane ring of Taxol from the 4(20)-ene-5α-acetoxy functional grouping. Cytochrome P450-catalyzed epoxidation of the 4(20)-double bond, followed by intramolecular acetate migration and oxirane ring opening, could furnish the oxetane moiety.
Figure 3:
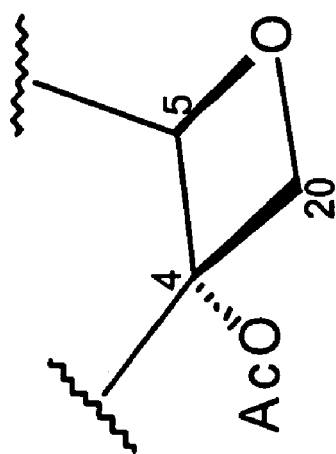
Figure 3:
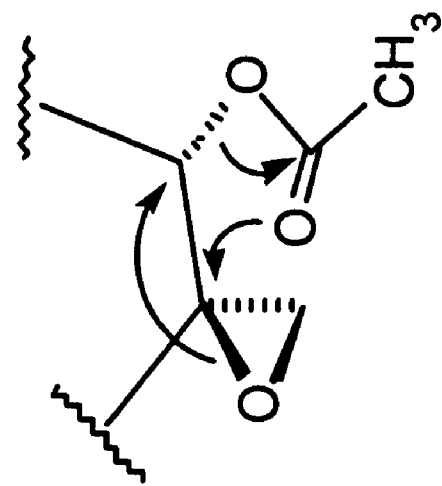

Complete $^1$H-NMR assignments and one-bond correlated $^{13}$C assignments (as measured indirectly from HSQC) for the biosynthetic product derived from taxadien-5α-yl acetate by the cytochrome P450 expressed from clone F14. For position numbering, see FIG. 1.

| Position number | Carbon (δ) | α-proton (δ) | β-proton (δ) |
|---|---|---|---|
| 1 | 43.9 | | 1.59 |
| 2 | 28 | 1.47 | 1.53 |
| 3 | 35.9 | 2.84 | |
| 4 | | | |
| 5 | 75.9 | | 5.47 |
| 6 | 27.9 | 1.66 | 1.55 |
| 7 | 33.6 | 1.94 | 0.9 |
| 8 | | | |
| 9 | 47.6 | 1.42 | 2.21 |
| 10 | 67.2 | 4.9 | |
| 11 | | | |
| 12 | | | |
| 13 | 30.3 | 1.8 | 2.26 |
| 14 | 22.7 | 1.26 | 1.96 |
| 15 | | | |
| 16 | 31.8 | 1.14 (exo) | |
| 17 | 25.3 | 1.59 (endo) | |
| 18 | 20.7 | 1.71 | |
| 19 | 21.4 | | 0.66 |
| 20 | 111.6 | 5.07 (exo) 4.67 (endo) | |
| 21 (acetate) | 21 | 1.66 | |

The 2D-TOCSY spectra (FIGS. 9A and 10) complemented the HSQC data and permitted additional regiochemical assignments. The H5 proton (δ 5.47) (FIGS. 10A and 10E) was correlated strongly with H6 (δ 1.66, δ 1.55) and H7 (δ 1.94, δ 0.9) protons but had no appreciable coupling to either of the H20 signals (δ 5.07, δ 4.67) or to H3 (δ 2.84), which is a common feature observed with taxadiene derivatives. The spin system defined in part by H3 (δ 2.84), H2 (δ 1.47 and δ 1.53), H1 (δ 1.59), H13 (δ 1.80, δ 2.26), and H14 (δ 1.26, δ 1.96) was apparent in FIGS. 10C and 10E. The H18 allylic methyl (δ 1.71) also displayed a weak correlation with H13. In contrast to the extended spin correlations noted in FIG. 10D, the H9 (δ 1.42, δ 2.21) and H10 (δ 4.9) signals formed an isolated spin system (see FIG. 10B), which included the H10 hydroxyl (δ 0.85). A correlation also was observed between the two gem-dimethyl signals (δ 1.14 and δ 1.59), which was consistent with the spectra of other taxadiene derivatives.

Figures 11A, 11B, 11C, 11D, 11E:
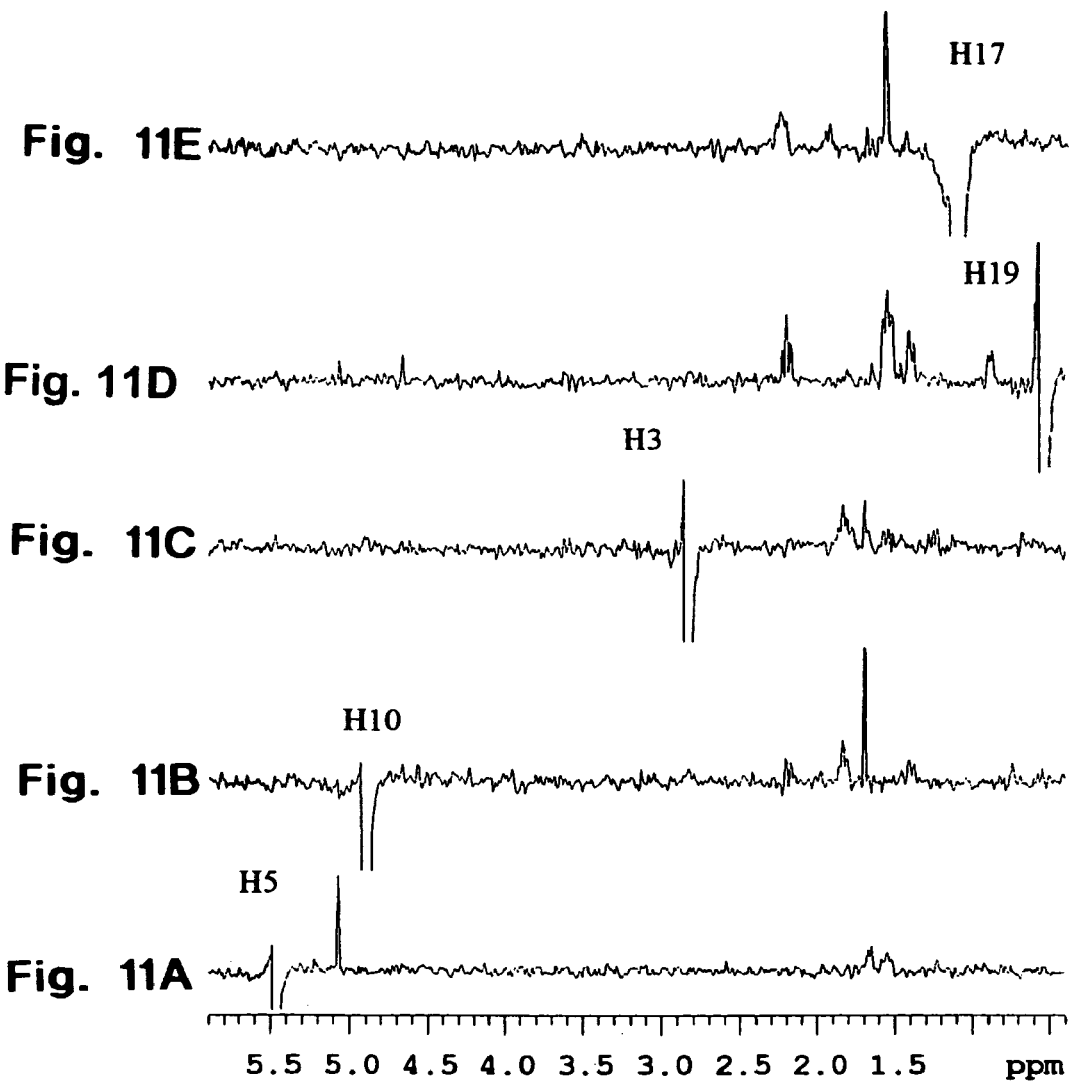

$^1$H—$^1$H ROESY (Rotational nuclear Overhauser Effect SpectroscopY) is useful for determining which signals arise from protons which are close in space but not closely connected by chemical bonds. Therefore, 2D-ROESY spectra (FIGS. 9B and 11) were used to confirm the regiochemical assignments and to assess relative stereochemistry (Several of these n.O.e correlations are listed in Table 4). $^1$H—$^1$H TOCSY (TOtal Correlated SpectroscopY) is useful for determining which signals arise from protons within a spin system, especially when the multiplets overlap or there is extensive second order coupling. The 2D-TOCSY (total correlation spectrum) described herein, showed that a second heteroatom was introduced into the C9-C10 fragment, but the regiochemistry was ambiguous based on this single measurement. The 2D-ROESY confirmed that oxidation had occurred at C10 and placed the C10 hydroxyl in the β-orientation. This assignment also was supported by an observed n.O.e between the H10 proton (δ 4.90) (FIG. 11B) and the allylic methyl, H18 (δ 1.71), which is consistent with an α-configuration for H10. Additional stereochemical assignments were made by noting correlations between H9β (δ 2.21) and the H17 methyl which must be endo (δ 1.59) (FIG. 11E), the H19 methyl (δ 0.56) which is β-oriented, and the H2β-proton (δ 1.53). The other H9 signal (δ 1.42) correlated with H19 and the H7β-proton (δ 0.90), as well as H10 (δ 4.90) (FIGS. 11D and 11B). It also was noted that $^3J_{HH}$ was large (11.7 Hz) between the H9β- and H10α-protons, consistent with a nearly axial arrangement for this pair; a smaller coupling (5.3 Hz) between H9α and H10 was consistent with an equatorial configuration between these two protons.

ROESY spectroscopy also was used to confirm the stereochemistry at H5. Moderately strong correlations were seen between H5 (δ 5.47) (see Table 4 and FIG. 11A) and both C6 signals (δ 1.66, δ 1.55), consistent with an equatorial orientation for H5. The $^3J_{HH}$ coupling was quite small (<3 Hz) between H5 and all other scalar-coupled partners, providing further evidence for the adopted equatorial orientation of H5. A moderately strong n.O.e between H5 and H20exo was noted, but there were no n.O.e correlations observed between H5 and other protons on the α-face of the molecule. These results confirmed that H5 was β-configured and that the acetate group was α-oriented as in the substrate. One other significant structural motif in taxadiene derivatives was the near occlusion of the H3 proton on the α-face due to the unusual folding of the molecule, thereby making the H3 proton (δ 2.84) a useful probe for this face. Indeed, n.O.e correlations were observed between H3, H10, H13α, and the allylic methyl H18 (Table 4 below, and FIG. 11C).

12:189-206, 1995; and von Wachenfeldt et al., in Ortiz de Montellano (ed.), *Cytochrome P450: Structure, Mechanism, and Biochemistry*, Plenum, New York, N.Y., pp. 183-223, 1995) with PFG element (aa 435-437).

F. In Vitro Assays of Isolated Enzymes for Taxoid Oxygenase Activity

The standard enzyme assay for assessing oxygenase activity of the recombinant cytochrome P450 employed the following conditions: 25 mM HEPES buffer, pH 7.5, 400 μM NADPH, 300 μg protein and 30 μM substrate (taxadiene, taxadienol, or taxadienyl acetate) in a total volume of 1 mL. Samples were incubated at 32° C. for 12 hours, after which 1 mL of saturated NaCl solution was added to the reaction mixture, followed by extraction of the product with 2 mL of hexane/ethyl acetate (4:1, v/v). The extracts were dried and dissolved in acetonitrile for product analysis by radio-HPLC [column: Alltech Econosil C18 5 μm particle size (250 mm×4.6 mm): solvent system A: 0.01% (v/v) $H_3PO_4$, 2% acetonitrile, 97.99% $H_2O$; solvent system B: 0.01% $H_3PO_4$, 99.99 acetonitrile; gradient: 0-5 minutes, 100% A; 5-15 minutes, 0-50% B; 15-55 minutes, 50-100% B; 55-65 minutes, 100% B; 65-70 minutes, 0-100% A; 70-75 minutes, 100% A; flow rate 1 mL/minute; for detection, a radio-chromatography detector (Flow-One®-Beta Series A-100, Radiomatic) was used].

Of the three test substrates (A, B, C), taxadiene was not converted detectably to an oxygenated product by recombinant cytochrome P450 clone F16 (SEQ ID NO: 88). Of the 5α-ol derivatives, taxa-4(20),11(12)-dien-5α-ol was converted most efficiently to a diol product as determined by GC-MS analysis (parent ion indicating a MW of 304). Pre-

TABLE 4 n.O.e. Correlations

| Proton | | n.O.e. | correlations | | | | |
|---|---|---|---|---|---|---|---|
| H3 | alpha | 10 (w) | 13-a (m) | 18 (w) | | | |
| H5 | beta | 20-exo (m) | 6-ab (m) | | | | |
| H7 | beta | 19 (w) | 9-a (m) | 6-ab (m) | 7-a (s) | | |
| H7 | alpha | 7-b (s) | 3 (m) | 10 (m) | 21 (w) ? | | |
| H9 | alpha | 9-b (s) | 7-b (m-w) | 19 (w) | 9-a (m) | OH (w) | |
| H9 | beta | 17 (m) | 9-a (s) | 2-b (w) | 19 (w) | | |
| H10 | alpha | 7-a (m) | 18 (m) | 9-a (m) | 19-b (w) | OH (w) | |
| H13 | beta | 14-b (m) | 13-a (s) | 18 (vw) | 16-exo (m) | | |
| H14 | alpha | 3 (w) | 14-b (s) | 13-a (m) | | | |
| H14 | beta | 14-a (s) | 16-exo (m) | 1 (m) | 13-b (m) | | |
| H16 | exo | 17-endo (m) | 3-b (m) | 14-b (m-w) | 1 (w) | | |
| H19 | beta | 20-endo (w) | 20-exo (w) | 7-b (m) | 9-ab (m) | 2-b (s) | 6-b (w) |
| H20 | endo | 20-exo (s) | 3 (w) | 2-a (s) | 19 (w) | | |
| H20 | exo | 20-endo (m) | 5 (m) | | | | |

This full assignment of the structure confirms the identity of the biosynthetic product as taxa-4(5),11(12)-dien-5α-acetoxy-10β-ol, and indicates that a cDNA encoding the cytochrome P450 taxane 10β-hydroxylase has been isolated. This 1494-bp cDNA (SEQ ID NO:51) translates a 497 residue deduced protein of molecular weight 56,690 that bears a typical N-terminal membrane anchor (Brown et al., *J. Biol. Chem.* 264:4442-4449, 1989), with a hydrophobic insertion segment (Nelson et al., *J. Biol. Chem.* 263:6038-6050, 1988) and a stop-transfer signal (Sakaguchi et al., *EMBO J.* 6:2425-2431, 1987). The protein possesses all of the conserved motifs anticipated for cytochrome P450 oxygenases, including the oxygen-binding domain (Shimada et al., in Bunabiki (ed.) *Oxygenases and Model Systems*, Kluwer, Boston, Mass., pp. 195-221, 1997) and the highly conserved heme-binding motif (Durst et al., *Drug Metab. Drug Interact.* parative incubations with taxadienol allowed the generation of ~100 μg of the diol product that was purified by a combination of reversed phase HPLC, as described above, and normal phase TLC (silica gel with toluene/acetone (3:1, v/v)) in preparation for structural determination by $^1$H— and $^{13}$C-NMR analysis (500 MHz). Comparison of spectra to those of authentic taxa-4(20),11(12)-dien-5α-ol (Hefner et al., *Chem. Biol.* 3:479-489, 1996) indicated that the product of the clone F16 (SEQ ID NO: 88) cytochrome P450 oxygenase reaction is taxa-4(20),11(12)-dien-5α,9α-diol. These results indicated that clone F16 (SEQ ID NO: 82) encodes a cytochrome P450 taxane 9α-hydroxylase, likely representing the third regiospecific hydroxylation step of the Taxol biosynthetic pathway.

Additionally, biochemical studies can be done to determine which diol resides on the Taxol pathway (i.e., the gene encoding the next pathway step suspected to be responsible for C10 hydroxylation), and to determine which activities (and genes) reside further down the pathway (catalyzing formation of triol, tetraol, pentaol, etc.) but that yield a cytochrome P450 oxygenase capable of catalyzing the hydroxylation of taxadien-5α-ol as an adventitious substrate. Other expression systems also can be tested to obtain functional expression of the remaining clones, and all functional clones are being tested with other taxoid substrates.

It is notable that some of the clones that are capable of transforming taxoid intermediates are from the same, closely related family (see placement of clones F9, F12, F14, and F51 (SEQ ID NOS: 61, 56, 64, and 60) in the dendrogram of FIG. 5(A)). Outlying clone 34, although it yielded a reliable CO-difference spectrum (confirming a functional cytochrome P450 and its utility for detecting CO), does not transform the taxoid substrates to oxygenated products. However, this clone when expressed in a different expression system may prove to be active against other taxoid substrates.

III. Other Oxygenases of the Taxol Pathway

The protocol described above yielded 21 related amplicons. Initial use of twelve amplicons as probes for screening the cDNA library allowed for the isolation and characterization of thirteen oxygenase-encoding DNA sequences. Subsequently, additional full-length enzymes were isolated. Several of these full-length sequences were expressed recombinantly and tested in situ, and ten were shown to be capable of binding CO, and, therefore, to be useful for detecting CO (Table 2). Additionally, nine clones were shown to be capable of hydroxylating taxoid substrates in vivo (Table 2).

There are at least five distinct oxygenases in the Taxol biosynthetic pathway (Hezari et al., *Planta Med.* 63:291-295, 1997), and the close relationship between the nucleic acid sequences of the 21 amplicons indicates that the remaining amplicon sequences represent partial nucleic acid sequences of the other oxygenases in the Taxol biosynthetic pathway. Hence, the above-described protocol enables the identification and recombinant production of oxygenases corresponding to the full-length versions of the 21 amplicon sequences provided. Therefore, the following discussion relating to Taxol oxygenases refers to the full-length oxygenases shown in the respective sequence listings, as well as the remaining oxygenases of the Taxol biosynthetic pathway that are identifiable through the use of the amplicon sequences. Furthermore, one of skill in the art will appreciate that the remaining oxygenases can be tested easily for enzymatic activity using "functional assays" such as the spectrophotometric assay described below, and direct assays for catalysis with the appropriate taxoid substrates.

IV. Isolating Oxygenases of the Taxol Biosynthetic Pathway

A. Cell Culture

Initiation, propagation, and induction of *Taxus* sp. cell cultures have been previously described (Hefner et al., *Arch. Biochem. Biophys.* 360:62-75, 1998). Enzymes and reagents were obtained from United States Biochemical Corp. (Cleveland, Ohio), Gibco BRL (Grand Island, N.Y.), Promega (Madison, Wis.) and New England BioLabs, Inc. (Beverly, Miss.), and were used according to the manufacturers' instructions. Chemicals were purchased from Sigma Chemical Co. (St. Louis, Mo.).

B. Vectors and DNA Manipulation

Unless otherwise stated, all routine DNA manipulations and cloning were performed by standard methods (Sambrook et al. (eds.), *Molecular Cloning: A Laboratory Manual* 2nd ed., vols. 1-3, Cold Spring Harbor Laboratory Press, Cold Spring Harbor, N.Y., 1989). PCR amplifications were performed by established procedures (Innis et al., *PCR Protocols: A Guide to Methods and Applications*, Academic Press, New York, 1990). DNA was sequenced using Amplitaq™ DNA polymerase (Roche, Somerville, N.J.) and fluorescence cycle sequencing on an Applied Biosystems Inc. Prism™ 373 DNA Sequencer (Perkin-Elmer, Norwalk, Conn.). The *Saccharomyces cerevisiae* expression vector pYeDP60 was as described previously (Pompon et al., *Methods Enzymol.* 272: 51-64, 1996).

C. *E. coli* and Yeast Strains

The *E. coli* strains XLI-Blue MRF' (Stratagene, La Jolla, Calif.) and TOP10F' (Invitrogen, Carlsbad, Calif.), were used for routine cloning and for cloning PCR products, respectively. The yeast strains used for expression each expressed one of two different *Arabidopsis thaliana* cytochrome P450 reductases, and were designated WAT11 and WAT21, respectively (Pompon et al., *Methods Enzymol.* 272:51-64, 1996).

D. cDNA Library Construction

A cDNA library was prepared from mRNA isolated from *T. cuspidata* suspension cell cultures, which had been induced to maximal Taxol production with methyl jasmonate for 16 hours. Isolation of total RNA from 1.5 g *T. cuspidata* cells was developed empirically using a buffer containing 4 M guanidine thiocyanate, 25 mM EDTA, 14 mM 2-mercaptoethanol, and 100 mM Tris-HCl, pH 7.5. Cells were homogenized on ice using a polytron (VWR Scientific, Salt Lake City, Utah) (4×15 second bursts at setting 7). The homogenate was adjusted to 2% (v/v) Triton X-100 and allowed to stand 15 minutes on ice, after which an equal volume of 3 M sodium acetate, pH 6.0 was added. After mixing, the solution was incubated on ice for an additional 15 minutes, followed by centrifugation at 15,000 g for 30 minutes at 4° C. The supernatant was mixed with 0.8 volume of isopropanol and left to stand on ice for 5 minutes. After centrifugation at 15,000 g for 30 minutes at 4° C., the resulting pellet was redissolved in 8 mL 20 mM Tris-HCl, pH 8.0, containing 1 mM EDTA, then adjusted to pH 7.0 by addition of 2 mL 2 M NaCl in 250 mM MOPS buffer at pH 7.0. Total RNA was recovered by passing this solution over a nucleic-acid-isolation column (Qiagen, Valencia, Calif.) following the manufacturer's instructions. Poly(A)⁺RNA was purified by using the Oligotex™ mRNA kit following the manufacturer's instructions (Qiagen, Valencia, Calif.). Messenger RNA prepared in this fashion was used to construct a library using a λZAPII™-cDNA synthesis kit and ZAP-cDNA gigapack III™ gold packaging kit (Stratagene, La Jolla, Calif.) following the manufacturer's instructions. The isolated mRNA also was used to construct a RACE (Rapid Amplification of cDNA Ends) library using a Marathon cDNA amplification kit (Clontech, Palo Alto, Calif.).

E. Differential Display of mRNA

Differential display of mRNA was performed using the Delta Differential Display Kit (Clontech, Palo Alto, Calif.) by following the manufacturer's instructions except were noted. Total RNA was isolated as described above from two different *Taxus cuspidata* suspension cell cultures, one that had been induced with methyl jasmonate 16 hours before RNA isolation and the other that had not been treated (i.e., uninduced). Cytochrome P450-specific forward primers (FIG. 4), instead of random primers, were used in combination with reverse-anchor-(dT)9N-1N-1 primers (where N−1=A, G, or C) provided in the kit. The anchor designed by Clontech was added to each P450-specific primer to increase the annealing temperature after the fourth low-stringency PCR cycle; this led to a significant reduction of the background signal. Each cytochrome P450-specific primer was used with the three anchored oligo(dT) primers terminated by each nucleotide. PCR reactions were performed with a RoboCycler™ 96 Temperature Cycler (Stratagene, La Jolla, Calif.), using one cycle at 94° C. for 5 minutes, 40° C. for 5 minutes, 68° C. for 5 minutes, followed by three cycles at 94° C. for 30 seconds, 40° C. for 30 seconds, 68° C. for 5 minutes, and 32 cycles at 94° C. for 20 seconds, 60° C. for 30 seconds, and 68° C. for 2 minutes. Finally, the reactions were heated at 68° C. for 7 minutes. The resulting amplicons were separated on a 6% denaturing polyacrylamide gel (HR-100, Genomyx Corporation, Foster City, Calif.) using the LR DNA Sequencer Electrophoresis System (Genomyx Corporation).

Differential display bands of interest were cut from the dried gel, eluted with 100 mL of 10 mM Tris-HCl buffer, pH 8.0, containing 1 mM EDTA, by incubation overnight at 4° C. A 5-mL aliquot of the extract was used to re-amplify the cDNA fragment by PCR using the same primers as in the original amplification. The reactions initially were heated to 94° C. for 2 minutes, then subjected to 30 cycles at 94° C. for 1 minute, 60° C. for 1 minute, and 68° C. for 2 minutes. Finally, to facilitate cloning of the PCR product, the reactions were heated at 68° C. for 7 minutes. Amplicons were analyzed by agarose gel electrophoresis as before. Bands were excised from the gel and the DNA was extracted from the agarose. This gel-purified cDNA was then transferred into the T/A cloning vector pCR2.1-TOPO (Invitrogen, Carlsbad, Calif.).

The DD-RT-PCR-based screening revealed about 100 clearly differentially expressed bands, all of which were sequenced and analyzed. Of these, 39 represented PCR products containing cytochrome P450-like sequences. The nucleotide and deduced peptide sequences of these 39 amplicons were compiled using the GCG fragment assembly programs and the sequence-alignment program "Pileup" (Genetics Computer Group, Program Manual for the Wisconsin Package, Version 9, Genetics Computer Group, 575 Science Drive, Madison, Wis., 1994). This comparison of cloned sequences revealed that C-terminal fragments from 21 different cytochrome P450 genes had been isolated. These cytochrome P450 sequences were used to prepare hybridization probes in order to isolate the corresponding full-length clones by screening the cDNA library.

F. cDNA Library Screening

Initially, 12 probes (SEQ ID NOS: 11, 10, 1, 5, 4, 19, 8, 17, 13, 14, 21, and 6, respectively) were labeled randomly using the Ready-To-Go™ kit (Amersham Pharmacia Biotech, Piscataway, N.J.) following the manufacturer's instructions. Plaque lifts of the *T. cuspidata* phage library were made on nylon membranes and were screened using a mixture of two radiolabeled probes. Phage DNA was cross-linked to the nylon membranes by autoclaving on fast cycle for 3 minutes at 120° C. After cooling, the membranes were washed for 5 minutes in 2×SSC (sodium citrate buffer). Prehybridization was performed for 1 to 2 hours at 65° C. in 6×SSC, containing 0.5% SDS, and 5× Denhardt's reagent. Hybridization was performed in the same buffer for 20 hours at 65° C. The nylon membranes were washed twice for 5 minutes each in 2×SSC with 0.1% SDS at room temperature, and twice for 1 hour each in 1×SSC with 0.1% SDS at 65° C. After washing, the membranes were exposed for 17 hours onto Kodak (Rochester, N.Y.) XAR™ film at −70° C. Positive plaques were purified through one additional round of hybridization. Purified λZAPII clones were excised in vivo as pBluescript II SK(+) phagemids (Stratagene, La Jolla, Calif.) and transformed into *E. coli* SOLR cells. The size of each cDNA insert was determined by PCR using T3 and T7 promoter primers. Inserts (>1.6 kb; of a size necessary to encode a typical cytochrome P450 of 50-60 kDa) were sequenced and sorted into groups based on sequence similarity/identity using the GCG fragment assembly programs (Genetics Computer Group, Program Manual for the Wisconsin Package, Version 9, Genetics Computer Group, 575 Science Drive, Madison, Wis., 1994). Each unique sequence was used as a query in database searching using either BLAST or FASTA programs (Genetics Computer Group, Program Manual for the Wisconsin Package, Version 9, Genetics Computer Group, 575 Science Drive, Madison, Wis., 1994), to define sequences with significant homology to plant cytochrome P450 sequences. These clones also were compared pairwise at both the nucleic acid and amino acid levels using the "Pileup" and "Gap" programs (Genetics Computer Group, Program Manual for the Wisconsin Package, Version 9, Genetics Computer Group, 575 Science Drive, Madison, Wis., 1994).

G. Generation of Full-Length Clones by 5'-RACE

Of the 13 clones initially examined, full-length sequences of nine were obtained by screening of the *T. cuspidata* λ-phage library with the corresponding probes (clones F12, F21, F31, F42, F51, F72, F9, F56, and F10, respectively (SEQ ID NOS: 43, 44, 46, 45, 47, 54, 48, 49, and 55, respectively)). To obtain the 5'-sequence portions of the other four truncated clones F14, F19, F34, and F55 (SEQ ID NOS: 51, 50, 53 and 52, respectively), 5'-RACE was performed using the Marathon cDNA amplification kit (Clontech, Palo Alto, Calif.) according to the manufacturer's instructions. The reverse primers used were: for F14, 5'-TCGGTGATTGTAACG-GAAGAGC-3' (SEQ ID NO: 69); for F19, 5'-CTG-GCTTTTCCAACGGAGCATGAG-3' (SEQ ID NO: 70); for F34, 5'-ATTGTTTCTCAGCCCGCGCAGTATG-3' (SEQ ID NO: 71); for F55, 5'-TCGGTTTCTATGACGGAA-GAGATG-3' (SEQ ID NO: 72). Using the defined 5'-sequences thus acquired, and the previously obtained 3'-sequence information, primers corresponding to these terminal regions were designed and the full-length versions of each clone were obtained by amplification with Pfu polymerase (Stratagene, La Jolla, Calif.) using library cDNA as target. These primers also were designed to contain nucleotide sequences encoding restriction sites that were used to facilitate cloning into the yeast expression vector.

H. cDNA Expression of Cytochrome P450 Enzymes in Yeast

Appropriate restriction sites were introduced by standard PCR methods (Innis et al., *PCR Protocols: A Guide to Methods and Applications*, Academic Press, San Diego, Calif., 1990) immediately upstream of the ATG start codon and downstream of the stop codon of all full-length cytochrome P450 clones. These modified amplicons were gel-purified, digested with the corresponding restriction enzymes, and then ligated into the expression vector pYeDP60. The vector/insert junctions were sequenced to ensure that no errors had been introduced by the PCR construction. Verified clones were transformed into yeast using the lithium acetate method (Ito et al., *J. Bacteriol.* 153:163-168, 1983). Isolated transformants were grown to stationary phase in SGI medium (Pompon et al., *Methods Enzymol.* 272:51-64, 1996), and used as inocula for a large-scale expression culture grown in YPL medium (Pompon et al., *Methods Enzymol.* 272:51-64, 1996). Approximately 24 hours after induction of cytochrome P450 expression with galactose (to 10% final concentration), a portion of the yeast cell culture was harvested by centrifugation. One-half of the culture was treated with carbon monoxide, and the cytochrome P450 CO-difference spectrum was recorded directly (using untreated cells as a control) by spectrophotometry (Omura and Sato, *J Biol. Chem.* 239:2370-2378, 1964).

This direct, in situ method for demonstrating the presence of functional, recombinant cytochrome P450, and for estimating the quantity of the competent enzyme, also can be applied to other expression systems, including *E. coli, Pichia pastoris*, insect cells (as described below), and *Spodoptera fugiperda* cells. Of the 13 full-length clones obtained so far, eight exhibit a detectable CO-difference spectrum when the recombinant cytochrome P450 gene product is expressed in this yeast system and assayed by this in situ method.

I. cDNA Expression of Cytochrome P450 Enzymes in Insect Cells

As mentioned above, insect cell expression systems, such as the baculovirus-*Spodoptera* system described below, can be used to express the oxygenases described herein.

For example, the functional identification of the *Taxus cuspidata* cytochrome P450 clone F16 was accomplished using the baculovirus-*Spodoptera* expression system. (The use of this system for the heterologous expression of cytochrome P450 genes has been described previously (Asseffa et al., *Arch. Biochem. Biophys*. 274:481-490, 1989; Gonzalez et al., *Methods Enzymol*. 206:93-99, 1991; and Kraus et al., *Proc. Natl. Acad. Sci. USA* 92:2071-2075, 1995)). For the heterologous expression of clone F16 in *Spodoptera fugiperda* Sf9 cells with the *Autographa californica* baculovirus expression system, the F16 cytochrome P450 open reading frame (orf) was amplified by PCR using the F16-pYEDP60 construct as a template. For PCR, two gene-specific primers were designed that contained, for the purpose of subcloning the F16 orf into the FastBac-1 vector (Life Technologies), a BamHI and a NotI restriction site (forward primer 5'-gggatccATGGCCCTTAAGCAATTG-GAAGTTTC-3' (SEQ ID NO: 93); reverse primer 5'-ggcg-gccgcTTAAGATCTGGAATAGAGTTTAATGG-3' (SEQ ID NO: 94)). The gel-purified PCR product so obtained was subcloned into the pCR-Blunt vector (Invitrogen, Carlsbad, Calif.). From the derived recombinant pCR-Blunt vector, the subcloned cytochrome P450 orf was excised using the added restriction sites, and the obtained DNA fragment was ligated into the BamHI/NotI-digested pFastBac1 vector (Life Technologies, Grand Island, N.Y.). The sequence and the correct insertion of clone F16 into the pFastBac1 vector were confirmed by sequencing of the insert. The pFastBac/F16orf construct was then used for the preparation of the recombinant Bacmid DNA by transformation of the *Escherichia coli* strain DH10Bac (Life Technologies). Construction of the recombinant Bacmid DNA and the transfection of *Spodoptera frugiperda* Sf9 cells were done according to the manufacturer's protocol.

The *Spodoptera frugiperda* Sf9 cell cultures were propagated either as adherent monolayer cultures in Grace insect cell culture medium (Life Technologies) supplemented with 10% FCS (Life Technologies) or as suspension cultures in Grace medium containing 10% FCS and 0.1% Pluronic F-68 (Sigman, St. Louis, Mo.). The adherent cell cultures were maintained in a chamber at 28° C. The suspension cultures were incubated in a shaker at 28° C. at 140 rpm. The adherent cell cultures were grown in T25 tissue culture flasks (Nalgene Nuc, Rochester, N.Y.) with passage of one-third to one-half of the culture every 2 to 3 days. For heterologous protein production, the cultures were grown as suspensions. The cells from two tissue culture flasks (80-90% confluent) were added to 50 mL of standard suspension insect culture medium in a 100 mL conical flask, and were incubated as above until a cell density of ~2×10$^6$ cells/mL was reached. The cells were collected by centrifugation at room temperature at 140 g for 10 minutes. The resulting cell pellet was resuspended in 1/10 of the original volume with fresh medium.

For the functional characterization of clone F16, the recombinant baculovirus carrying the cytochrome P450 clone F16 ORF was coexpressed with a recombinant baculovirus carrying the *Taxus* NADPH:cytochrome P450 reductase gene. To the insect cell suspension, the two recombinant baculoviruses were added at a multiplicity of infection of 1-5. The viral titers were determined according to the End-Point Dilution method (O'Reilly et al., *Baculovirus Expression Vectors, A Laboratory Manual*, New York, N.Y., Freeman and Company, 1992). For infection, the cells were incubated for 1 hour at 28° C. and 80 rpm. The cell culture volume was brought to 50 mL with standard cell culture medium, and hemin (Sigma) was added to a final concentration of 2 μg/mL. The infected cells were incubated for 48 hours in a gyratory shaker at 28° C. and 140 rpm. The infected insect cells were harvested from the cell culture medium by centrifugation as described above, and washed twice with PBS (50 mM $KH_2PO_4$, pH 7.5, 0.9% NaCl). The cell pellet so obtained was resuspended in 5 mL of HEPES/DTT Buffer (25 mM HEPES, pH 7.5, 1 mM DTT). The cells were lysed by mild sonication (VirSonic, Virtis Company, Gardiner, N.Y.), the cell debris was removed by centrifugation at 5,000 g for 10 minutes at 4° C., and the resulting supernatant was collected for use in enzyme assays.

J. Assay of Recombinant Cytochrome P450 Activity Toward Taxoid Substrates

Isolated transformants for each full-length cytochrome P450 clone shown to express a functional enzyme by CO-difference spectrum (ten clones) were grown to stationary phase in 2 mL SGI medium at 30° C. and used to inoculate a 10-mL expression culture (in YPL medium). Approximately 8 hours after induction, cells were harvested by centrifugation (10 minutes at 1500 rpm), and the pellet was resuspended in 2 mL of fresh YPL medium.

To eliminate additional complication and uncertainty associated with microsome isolations for in vitro assays, 10$^6$ dpm of [20-$^3$H$_3$]taxa-4(5),11(12)-diene (16 Ci/mol) or [20-$^3$H$_2$] taxa-4(20),11(12)-dien-5-α-ol (4.0 Ci/mol), or other taxoid substrate were added directly to the cell suspension to assay conversion in vivo. After 12 hours of incubation at 30° C. with agitation (250 rpm), the mixture was treated for 15 minutes in a sonication bath and extracted 3 times with 2 mL diethyl ether to insure isolation of the biosynthetic products. These ether extracts, containing residual substrate and derived product(s), were concentrated to dryness, resuspended in 200 μL of $CH_3CN$, and filtered. These samples were analyzed by radio-HPLC (Hefner et al., *Chemistry and Biology* 3:479-489, 1996) using a 4.6 mm i.d.×250 mm column of Econosil C18, 5 μ (Alltech, Deerfield, Ill.) with a gradient of $CH_3CN$ in $H_2O$ from 0% to 85% (10 minutes at 1 mL/minute), then to 100% $CH_3CN$ over 40 minutes.

The foregoing method is capable of separating taxoids ranging in polarity from taxadiene to approximately that of taxadien-hexaol. For confirmation of product type, gas chromatography-mass spectrometry (GC-MS) or liquid chromatography-mass spectrometry (LC-MS) is employed, depending on the volatility of the product.

In the present example, of the eight clones confirmed to be functional by CO difference spectra, four exhibited a hydroxylated product in situ when incubated with taxadien-5α-ol.

K. Substrate Preparation

The syntheses of [20-$^3$H$_3$]taxa-4(5),11(12)-diene (16 Ci/mol) and [20-$^3$H$_2$]taxa-4(20),11(12)-dien-5α-ol (4.0 Ci/mol) have been described elsewhere (Hefner et al., *Chemistry and Biology* 3:479-489, 1996; and Rubenstein et al., *J. Org. Chem*. 60:7215-7223, 1995, respectively). Other taxane substrates (diols, triols, and tetraols of taxadiene) needed to monitor more advanced cytochrome P450-mediated bioconversions are generated by incubating radiolabeled taxa-4(20), 11(12)-dien-5α-ol with isolated *T. canadensis* microsomes, or appropriate recombinant cytochrome P450 enzymes, and separating the products by preparative (radio)HPLC. Taxusin (5α,9α,10,13α-tetraacetoxy-taxa-4(20),11(12)-diene) is isolated from *Taxus* heartwood and purified by standard chromatographic procedures (De Case De Marcano et al., *Chem. Commun.* 1282-1294, 1969). Following deacetylation and reacetylation with [$^{14}$C] acetic anhydride, this labeled substrate is used to monitor enzymatic hydroxylation at C1, C2, and C7 and epoxidation at C4-C20. 2α-Isobutyryloxy-5α, 7α, 10β-triacetoxy-taxa-4(20),11(12)-diene, isolated from the same source (De Case De Marcano et al., *Chem. Commun.* 1282-1294, 1969), can be modified similarly to provide a substrate for monitoring hydroxylation at C9 and C13. If taxa-4(20),11(12)-dien-5α-ol is hydroxylated at C10 as an early step, then the surrogate substrates for examining enzymatic oxygenation at all relevant positions of the taxane ring can be procured.

L. NMR Spectrometry

All NMR spectra were recorded on a Varian Inova-500 NMR spectrometer operating at 18° C. using a very sensitive 5 mm pulsed-field-gradient $^1$H indirect-detection probe. The taxadien-diol monoacetate was dissolved in $C_6D_6$ to a final concentration of about 300 μM. A 2D-TOCSY spectrum was acquired using a z-filtered DIPSI mixing sequence, a 60 msec mixing time, 10 kHz spin-lock field, 16 repetitions, 256 ($t_1$)× 2048 ($t_2$) complex points, and 6500 Hz sweep in each dimension. The 2D-ROESY spectrum was acquired using a z-filtered mixing sequence with a 409 msec mixing time, 4 kHz spin-lock field, 128 repetitions, 256 ($t_1$)×2048 ($t_2$) complex points, and 6500 Hz sweep in each dimension. A 2D-HSQC spectrum was acquired using 256 repetitions, 128 ($t_1$)×1024 ($t_2$) complex points, and 6500 Hz in F2 and 15000 Hz in F1. The time between repetitions was 1.5 seconds for these experiments. Data were processed using the Varian, Inc. VNMR software, version 6.1C. The final data size, after linear-prediction in ($t_1$) and zero-filling in both dimensions, was 1024(F1)×2048(F2) complex points for all experiments.

EXAMPLES

1. Oxygenase Protein and Nucleic acid Sequences

As described above, the invention provides oxygenases and oxygenase-specific nucleic acid sequences. With the provision herein of these oxygenase sequences, the polymerase chain reaction (PCR) may be utilized as a preferred method for identifying and producing nucleic acid sequences encoding the oxygenases. For example, PCR amplification of the oxygenase sequences may be accomplished either by direct PCR from a plant cDNA library or by Reverse-Transcription PCR (RT-PCR) using RNA extracted from plant cells as a template. Oxygenase sequences may be amplified from plant genomic libraries, or plant genomic DNA. Methods and conditions for both direct PCR and RT-PCR are known in the art and are described in Innis et al., *PCR Protocols: A Guide to Methods and Applications*, Academic Press: San Diego, 1990.

The selection of PCR primers is made according to the portions of the cDNA (or gene) that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al., *PCR Protocols: A Guide to Methods and Applications*, Academic Press: San Diego, 1990; Sambrook et al. (eds.), *Molecular Cloning: A Laboratory Manual* 2nd ed., vols. 1-3, Cold Spring Harbor Laboratory Press, Cold Spring Harbor, N.Y., 1989; and Ausubel et al. (eds.) *Current Protocols in Molecular Biology*, Greene Publishing and Wiley-Interscience, New York (with periodic updates), 1987. By way of example, the cDNA molecules corresponding to additional oxygenases may be amplified using primers directed toward regions of homology between the 5' and 3' ends of the full-length clone such as the one shown in SEQ ID NO: 43 sequences. Example primers for such a reaction are:

```
primer 1:
5'-CCI CCI GGI AAI ITI-3'          (SEQ ID NO. 81)

primer 2:
5'-ICC I(G/C)C ICC (G/A)AA IGG-3'  (SEQ ID NO. 82)
```

These primers are illustrative only; it will be appreciated by one skilled in the art that many different primers may be derived from the provided nucleic acid sequences. Re-sequencing of PCR products obtained by these amplification procedures is recommended to facilitate confirmation of the amplified sequence and to provide information on natural variation between oxygenase sequences. Oligonucleotides derived from the oxygenase sequence may be used in such sequencing methods.

Oligonucleotides that are derived from the oxygenase sequences are encompassed within the scope of the present invention. Preferably, such oligonucleotide primers comprise a sequence of at least 10-20 consecutive nucleotides of the oxygenase sequences. To enhance amplification specificity, oligonucleotide primers comprising at least 15, 20, 25, 30, 35, 40, 45 or 50 consecutive nucleotides of these sequences also may be used.

A. Oxygenases in Other Plant Species

Orthologs of the oxygenase genes are present in a number of other members of the *Taxus* genus. With the provision herein of the oxygenase nucleic acid sequences, the cloning by standard methods of cDNAs and genes that encode oxygenase orthologs in these other species is now enabled. As described above, orthologs of the disclosed oxygenase genes have oxygenase biological activity and are typically characterized by possession of at least 50% sequence identity counted over the full-length alignment with the amino acid sequence of the disclosed oxygenase sequences using the NCBI Blast 2.0 (gapped blastp set to default parameters). Proteins with even greater sequence identity to the reference sequences will show increasing percentage identities when assessed by this method, such as at least 60%, at least 65%, at least 70%, at least 75%, at least 80%, at least 90%, or at least 95% sequence identity.

Both conventional hybridization and PCR amplification procedures may be utilized to clone sequences encoding oxygenase orthologs. Common to both of these techniques is the hybridization of probes or primers that are derived from the oxygenase nucleic acid sequences. Furthermore, the hybridization may occur in the context of Northern blots, Southern blots, or PCR.

Direct PCR amplification may be performed on cDNA or genomic libraries prepared from the plant species in question, or RT-PCR may be performed using mRNA extracted from the plant cells using standard methods. PCR primers will comprise at least 10 consecutive nucleotides of the oxygenase sequences. One of skill in the art will appreciate that sequence differences between the oxygenase nucleic acid sequence and the target nucleic acid to be amplified may result in lower amplification efficiencies. To compensate for this, longer PCR primers or lower annealing temperatures may be used during the amplification cycle. Whenever lower annealing temperatures are used, sequential rounds of amplification using nested primer pairs may be necessary to enhance specificity.

For conventional hybridization techniques the hybridization probe is preferably conjugated with a detectable label such as a radioactive label, and the probe is preferably at least 10 nucleotides in length. As is well known in the art, increasing the length of hybridization probes tends to give enhanced specificity. The labeled probe derived from the oxygenase nucleic acid sequence may be hybridized to a plant cDNA or genomic library and the hybridization signal detected using methods known in the art. The hybridizing colony or plaque (depending on the type of library used) is purified and the cloned sequence contained in that colony or plaque isolated and characterized.

Orthologs of the oxygenases alternatively may be obtained by immunoscreening of an expression library. With the provision herein of the disclosed oxygenase nucleic acid sequences, the enzymes may be expressed and purified in a heterologous expression system (e.g., *E. coli*) and used to raise antibodies (monoclonal or polyclonal) specific for oxygenases. Antibodies also may be raised against synthetic peptides derived from the oxygenase amino acid sequence presented herein. Methods of raising antibodies are well known in the art and are described generally in Harlow and Lane, *Antibodies, A Laboratory Manual*, Cold Springs Harbor, 1988. Such antibodies can be used to screen an expression cDNA library produced from a plant. This screening will identify the oxygenase ortholog. The selected cDNAs can be confirmed by sequencing and enzyme activity assays.

B. Taxol Oxygenase Variants

With the provision of the oxygenase amino acid sequences (SEQ ID NOS: 56-68) and the corresponding cDNA (SEQ ID NOS: 43-55 and 81-86), variants of these sequences now can be created.

Variant oxygenases include proteins that differ in amino acid sequence from the oxygenase sequences disclosed, but that retain oxygenase biological activity. Such proteins may be produced by manipulating the nucleotide sequence encoding the oxygenase using standard procedures such as site-directed mutagenesis or the polymerase chain reaction. The simplest modifications involve the substitution of one or more amino acids for amino acids having similar biochemical properties. These so-called "conservative substitutions" are likely to have minimal impact on the activity of the resultant protein. Table 4 shows amino acids that may be substituted for an original amino acid in a protein and that are regarded as conservative substitutions.

TABLE 4

| Original Residue | Conservative Substitutions |
|---|---|
| ala | Ser |
| arg | Lys |
| asn | Gln; his |
| asp | Glu |
| cys | Ser |
| gln | Asn |
| glu | Asp |
| gly | Pro |
| his | Asn; gln |
| ile | Leu; val |
| leu | ile; val |
| lys | Arg; gln; glu |
| met | Leu; ile |
| phe | Met; leu; tyr |

TABLE 4-continued

| Original Residue | Conservative Substitutions |
|---|---|
| ser | Thr |
| thr | Ser |
| trp | Tyr |
| tyr | Trp; phe |
| val | ile; leu |

More substantial changes in enzymatic function or other features may be obtained by selecting substitutions that are less conservative than those in Table 4, i.e., by selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions that in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for oxygenase derivatives by analyzing the ability of the derivative proteins to catalyse the conversion of one Taxol precursor to another Taxol precursor.

Variant oxygenase cDNA or genes may be produced by standard DNA-mutagenesis techniques, for example, M13 primer mutagenesis. Details of these techniques are provided in Sambrook et al. (eds.), *Molecular Cloning: A Laboratory Manual* 2nd ed., vols. 1-3, Cold Spring Harbor Laboratory Press, Cold Spring Harbor, N.Y., 1989, Ch. 15. By the use of such techniques, variants may be created that differ in minor ways from the oxygenase cDNA or gene sequences, yet that still encode a protein having oxygenase biological activity. DNA molecules and nucleotide sequences that are derivatives of those specifically disclosed herein and that differ from those disclosed by the deletion, addition, or substitution of nucleotides while still encoding a protein having oxygenase biological activity are comprehended by this invention. In their simplest form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence in such a way that, while the nucleotide sequence is substantially altered, it nevertheless encodes a protein having an amino acid sequence identical or substantially similar to the disclosed oxygenase amino acid sequences. For example, the nineteenth amino acid residue of the oxygenase (Clone F12, SEQ ID NO: 43) is alanine. This is encoded in the open reading frame (ORF) by the nucleotide codon triplet GCT. Because of the degeneracy of the genetic code, three other nucleotide codon triplets-GCA, GCC, and GCG-also code for alanine. Thus, the nucleotide sequence of the ORF can be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences that encode the oxygenase protein but that vary from the disclosed nucleic acid sequences by virtue of the degeneracy of the genetic code.

Variants of the oxygenase also may be defined in terms of their sequence identity with the oxygenase amino acid (SEQ ID NOS: 56-68 and 87-92) and nucleic acid sequences (SEQ ID NOS: 43-55 and 81-86). As described above, oxygenases have oxygenase biological activity and share at least 60% sequence identity with the disclosed oxygenase sequences. Nucleic acid sequences that encode such proteins may be readily determined simply by applying the genetic code to the amino acid sequence of the oxygenase, and such nucleic acid molecules may readily be produced by assembling oligonucleotides corresponding to portions of the sequence.

As previously mentioned, another method of identifying variants of the oxygenases is nucleic acid hybridization. Nucleic acid molecules derived from the oxygenase cDNA and gene sequences include molecules that hybridize under various conditions to the disclosed Taxol oxygenase nucleic acid molecules, or fragments thereof.

Nucleic acid duplex or hybrid stability is expressed as the melting temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by 5° C.). In practice, the change in $T_m$ can be between 0.5° C. and 1.5° C. per 1% mismatch.

Generally, hybridization conditions are classified into categories, for example very high stringency, high stringency, and low stringency. The conditions for probes that are about 600 base pairs or more in length are provided below in three corresponding categories.

| Very High Stringency (sequences greater than 90% sequence identity) | | | | |
|---|---|---|---|---|
| Hybridization in | 5× | SSC at | 65° C. | 16 hours |
| Wash twice in | 2× | SSC at | room temp. | 15 minutes each |
| Wash twice in | 2× | SSC at | 55° C. | 20 minutes each |
| High Stringency (detects sequences that share approximately 80% sequence identity) | | | | |
| Hybridization in | 5× | SSC at | 42° C. | 16 hours |
| Wash twice in | 2× | SSC at | room temp. | 20 minutes each |
| Wash once in | 2× | SSC at | 42° C. | 30 minutes each |
| Low Stringency (detects sequences that share 70% sequence identity or greater) | | | | |
| Hybridization in | 6× | SSC at | room temp. | 16 hours |
| Wash twice in | 2× | SSC at | room temp. | 20 minutes each |

The sequences encoding the oxygenases identified through hybridization may be incorporated into transformation vectors and introduced into host cells to produce the respective oxygenase.

2. Introduction of Oxygenases into Plants

After a cDNA (or gene) encoding a protein involved in the determination of a particular plant characteristic has been isolated, standard techniques may be used to express the cDNA in transgenic plants in order to modify the particular plant characteristic. The basic approach is to clone the cDNA into a transformation vector, such that the cDNA is operably linked to control sequences (e.g., a promoter) directing expression of the cDNA in plant cells. The transformation vector is introduced into plant cells by any of various techniques (e.g., electroporation), and progeny plants containing the introduced cDNA are selected. Preferably all or part of the transformation vector stably integrates into the genome of the plant cell. That part of the transformation vector that integrates into the plant cell and that contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifest as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology include:

U.S. Pat. No. 5,571,706 ("Plant Virus Resistance Gene and Methods")

U.S. Pat. No. 5,677,175 ("Plant Pathogen Induced Proteins")

U.S. Pat. No. 5,510,471 ("Chimeric Gene for the Transformation of Plants")

U.S. Pat. No. 5,750,386 ("Pathogen-Resistant Transgenic Plants")

U.S. Pat. No. 5,597,945 ("Plants Genetically Enhanced for Disease Resistance")

U.S. Pat. No. 5,589,615 ("Process for the Production of Transgenic Plants with Increased Nutritional Value Via the Expression of Modified 2S Storage Albumins")

U.S. Pat. No. 5,750,871 ("Transformation and Foreign Gene Expression in *Brassica* Species")

U.S. Pat. No. 5,268,526 ("Overexpression of Phytochrome in Transgenic Plants")

U.S. Pat. No. 5,262,316 ("Genetically Transformed Pepper Plants and Methods for their Production")

U.S. Pat. No. 5,569,831 ("Transgenic Tomato Plants with Altered Polygalacturonase Isoforms")

These examples include descriptions of transformation vector selection, transformation techniques, and the construction of constructs designed to over-express the introduced cDNA. In light of the foregoing and the provision herein of the oxygenase amino acid sequences and nucleic acid sequences, it is thus apparent that one of skill in the art will be able to introduce the cDNAs, or homologous or derivative forms of these molecules, into plants in order to produce plants having enhanced oxygenase activity. Furthermore, the expression of one or more oxygenases in plants may give rise to plants having increased production of Taxol and related compounds.

A. Vector Construction, Choice of Promoters

A number of recombinant vectors suitable for stable transfection of plant cells or for the establishment of transgenic plants have been described, including those described in Weissbach and Weissbach, *Methods for Plant Molecular Biology*, Academic Press, 1989; and Gelvin et al., *Plant and Molecular Biology Manual*, Kluwer Academic Publishers, 1990. Typically, plant-transformation vectors include one or more cloned plant genes (or cDNAs) under the transcriptional control of 5'- and 3'-regulatory sequences and a dominant selectable marker. Such plant transformation vectors typically also contain a promoter regulatory region (e.g., a regulatory region controlling inducible or constitutive, environmentally or developmentally regulated, or cell- or tissue-specific expression), a transcription-initiation start site, a ribosome-binding site, an RNA processing signal, a transcription-termination site, and/or a polyadenylation signal.

Examples of constitutive plant promoters that may be useful for expressing the cDNA include: the cauliflower mosaic virus (CaMV) 35S promoter, which confers constitutive, high-level expression in most plant tissues (see, e.g., Odel et al., *Nature* 313:810, 1985; Dekeyser et al., *Plant Cell* 2:591, 1990; Terada and Shimamoto, *Mol. Gen. Genet.* 220:389, 1990; and Benfey and Chua, *Science* 250:959-966, 1990); the nopaline synthase promoter (An et al., *Plant Physiol.* 88:547, 1988); and the octopine synthase promoter (Fromm et al., *Plant Cell* 1:977, 1989). *Agrobacterium*-mediated transformation of *Taxus* species has been accomplished, and the resulting callus cultures have been shown to produce Taxol (Han et al., *Plant Science* 95: 187-196, 1994). Therefore, it is likely that incorporation of one or more of the described oxygenases under the influence of a strong promoter (like CaMV promoter) would increase production yields of Taxol and related taxoids in such transformed cells.

A variety of plant gene promoters that are regulated in response to environmental, hormonal, chemical, and/or developmental signals also can be used for expression of the cDNA in plant cells, including promoters regulated by: (a) heat (Callis et al., *Plant Physiol.* 88:965, 1988; Ainley, et al., *Plant Mol. Biol.* 22:13-23, 1993; and Gilmartin et al., *The Plant Cell* 4:839-949, 1992); (b) light (e.g., the pea rbcS-3A promoter, Kuhlemeier et al., *Plant Cell* 1:471, 1989, and the maize rbcS promoter, Schaffner and Sheen, *Plant Cell* 3:997, 1991); (c) hormones, such as abscisic acid (Marcotte et al., *Plant Cell* 1:969, 1989); (d) wounding (e.g., wunI, Siebertz et al., *Plant Cell* 1:961, 1989); and (e) chemicals such as methyl jasmonate or salicylic acid (see also Gatz et al., *Ann. Rev. Plant Physiol. Plant Mol. Biol.* 48:9-108, 1997).

Alternatively, tissue-specific (root, leaf, flower, and seed, for example) promoters (Carpenter et al., *The Plant Cell* 4:557-571, 1992; Denis et al., *Plant Physiol.* 101:1295-1304, 1993; Opperman et al., *Science* 263:221-223, 1993; Stockhause et al., *The Plant Cell* 9:479-489, 1997; Roshal et al., *Embo. J.* 6:1155, 1987; Schernthaner et al., *Embo J.* 7:1249, 1988; and Bustos et al., *Plant Cell* 1:839, 1989) can be fused to the coding sequence to obtain a particular expression in respective organs.

Alternatively, the native oxygenase gene promoters may be utilized. With the provision herein of the oxygenase nucleic acid sequences, one of skill in the art will appreciate that standard molecular biology techniques can be used to determine the corresponding promoter sequences. One of skill in the art also will appreciate that less than the entire promoter sequence may be used in order to obtain effective promoter activity. The determination of whether a particular region of this sequence confers effective promoter activity may be ascertained readily by operably linking the selected sequence region to an oxygenase cDNA (in conjunction with suitable 3' regulatory region, such as the NOS 3' regulatory region as discussed below) and determining whether the oxygenase is expressed.

Plant-transformation vectors also may include RNA processing signals, for example, introns, that may be positioned upstream or downstream of the ORF sequence in the transgene. In addition, the expression vectors also may include additional regulatory sequences from the 3'-untranslated region of plant genes, e.g., a 3'-terminator region, to increase mRNA stability of the mRNA, such as the PI-II terminator region of potato or the octopine or nopaline synthase (NOS) 3'-terminator regions. The native oxygenase gene 3'-regulatory sequence also may be employed.

Finally, as noted above, plant-transformation vectors also may include dominant selectable marker genes to allow for the ready selection of transformants. Such genes include those encoding antibiotic-resistance genes (e.g., resistance to hygromycin, kanamycin, bleomycin, G418, streptomycin, or spectinomycin) and herbicide-resistance genes (e.g., phosphinothricin acetyloxygenase).

B. Arrangement of Taxol oxygenase Sequence in a Vector

The particular arrangement of the oxygenase sequence in the transformation vector is selected according to the type of expression of the sequence that is desired.

In most instances, enhanced oxygenase activity is desired, and the oxygenase ORF is operably linked to a constitutive high-level promoter such as the CaMV 35S promoter. As noted above, enhanced oxygenase activity also may be achieved by introducing into a plant a transformation vector containing a variant form of the oxygenase cDNA or gene, for example a form that varies from the exact nucleotide sequence of the oxygenase ORF, but that encodes a protein retaining an oxygenase biological activity.

C. Transformation and Regeneration Techniques

Transformation and regeneration of both monocotyledonous and dicotyledonous plant cells are now routine, and the appropriate transformation technique can be determined by the practitioner. The choice of method varies with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG)-mediated transformation; transformation using viruses; micro-injection of plant cells; micro-projectile bombardment of plant cells; vacuum infiltration; and *Agrobacterium tumefaciens* (AT)-mediated transformation. Typical procedures for transforming and regenerating plants are described in the patent documents listed at the beginning of this section.

D. Selection of Transformed Plants

Following transformation and regeneration of plants with the transformation vector, transformed plants can be selected using a dominant selectable marker incorporated into the transformation vector. Typically, such a marker confers antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to assess production levels of Taxol and related compounds.

3. Production of Recombinant Taxol oxygenase in Heterologous Expression Systems

Various yeast strains and yeast-derived vectors are used commonly for the expression of heterologous proteins. For instance, *Pichia pastoris* expression systems, obtained from Invitrogen (Carlsbad, Calif.), may be used to practice the present invention. Such systems include suitable *Pichia pastoris* strains, vectors, reagents, transformants, sequencing primers, and media. Available strains include KM71H (a prototrophic strain), SMD1168H (a prototrophic strain), and SMD1168 (a pep4 mutant strain) (Invitrogen Product Catalogue, 1998, Invitrogen, Carlsbad Calif.).

Non-yeast eukaryotic vectors may be used with equal facility for expression of proteins encoded by modified nucleotides according to the invention. Mammalian vector/host cell systems containing genetic and cellular control elements capable of carrying out transcription, translation, and post-translational modification are well known in the art. Examples of such systems are the well-known baculovirus system, the ecdysone-inducible expression system that uses regulatory elements from *Drosophila melanogaster* to allow control of gene expression, and the sindbis viral-expression system that allows high-level expression in a variety of mammalian cell lines, all of which are available from Invitrogen, Carlsbad, Calif.

The cloned expression vector encoding one or more oxygenases may be transformed into any of various cell types for expression of the cloned nucleotide. Many different types of cells may be used to express modified nucleic acid molecules. Examples include cells of yeasts, fungi, insects, mammals, and plants, including transformed and non-transformed cells. For instance, common mammalian cells that could be used include HeLa cells, SW-527 cells (ATCC deposit #7940), WISH cells (ATCC deposit #CCL-25), Daudi cells (ATCC deposit #CCL-213), Mandin-Darby bovine kidney cells (ATCC deposit #CCL-22) and Chinese hamster ovary (CHO) cells (ATCC deposit #CRL-2092). Common yeast cells include *Pichia pastoris* (ATCC deposit #201178) and *Saccharomyces cerevisiae* (ATCC deposit #46024). Insect cells include cells from *Drosophila melanogaster* (ATCC deposit #CRL-10191), the cotton bollworm (ATCC deposit #CRL-9281), and *Trichoplusia ni* egg cell homoflagellates. Fish cells that may be used include those from rainbow trout (ATCC deposit #CLL-55), salmon (ATCC deposit #CRL-1681), and zebrafish (ATCC deposit #CRL-2147). Amphibian cells that may be used include those of the bullfrog, *Rana catesbelana* (ATCC deposit #CLL-41). Reptile cells that may be used include those from Russell's viper (ATCC deposit #CCL-140). Plant cells that could be used include *Chlamydomonas* cells (ATCC deposit #30485), *Arabidopsis* cells (ATCC deposit #54069) and tomato plant cells (ATCC deposit #54003). Many of these cell types are commonly used and are available from the ATCC as well as from commercial suppliers such as Pharmacia (Uppsala, Sweden), and Invitrogen.

Expressed protein may be accumulated within a cell or may be secreted from the cell. Such expressed protein may then be collected and purified. This protein may be characterized for activity and stability and may be used to practice any of the various methods according to the invention.

4. Creation of Oxygenase Specific Binding Agents

Antibodies to the oxygenase enzymes, and fragments thereof, of the present invention may be useful for purification of the enzymes. The provision of the oxygenase sequences allows for the production of specific antibody-based binding agents to these enzymes.

Monoclonal or polyclonal antibodies may be produced to an oxygenase, portions of the oxygenase, or variants thereof. Optimally, antibodies raised against epitopes on these antigens will detect the enzyme specifically. That is, antibodies raised against an oxygenase would recognize and bind the oxygenase, and would not substantially recognize or bind to other proteins. The determination that an antibody specifically binds to an antigen is made by any one of a number of standard immunoassay methods; for instance, Western blotting, Sambrook et al. (eds.), *Molecular Cloning: A Laboratory Manual*, 2nd ed., vols. 1-3, Cold Spring Harbor Laboratory Press, Cold Spring Harbor, N.Y., 1989.

To determine that a given antibody preparation (such as a preparation produced in a mouse against SEQ ID NO: 56) specifically detects the oxygenase by Western blotting, total cellular protein is extracted from cells and electrophoresed on an SDS-polyacrylamide gel. The proteins are transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of 5-bromo-4-chloro-3-indolyl phosphate/nitro blue tetrazolium results in the production of a densely blue-colored compound by immuno-localized alkaline phosphatase.

Antibodies that specifically detect an oxygenase will be shown, by this technique, to bind substantially only the oxygenase band (having a position on the gel determined by the molecular weight of the oxygenase). Non-specific binding of the antibody to other proteins may occur and may be detectable as a weaker signal on the Western blot (which can be quantified by automated radiography). The non-specific nature of this binding will be recognized by one skilled in the art by the weak signal obtained on the Western blot relative to the strong primary signal arising from the specific anti-oxygenase binding.

Antibodies that specifically bind to an oxygenase according to the invention belong to a class of molecules that are referred to herein as "specific binding agents." Specific binding agents capable of specifically binding to the oxygenase of the present invention may include polyclonal antibodies, monoclonal antibodies and fragments of monoclonal antibodies such as Fab, F(ab')$_2$ and Fv fragments, as well as any other agent capable of specifically binding to one or more epitopes on the proteins.

Substantially pure oxygenase suitable for use as an immunogen can be isolated from transfected cells, transformed cells, or from wild-type cells. Concentration of protein in the final preparation is adjusted, for example, by concentration on an Amicon filter device, to the level of a few micrograms per milliliter. Alternatively, peptide fragments of an oxygenase may be utilized as immunogens. Such fragments may be synthesized chemically using standard methods, or may be obtained by cleavage of the whole oxygenase enzyme followed by purification of the desired peptide fragments. Peptides as short as three or four amino acids in length are immunogenic when presented to an immune system in the context of a Major Histocompatibility Complex (MHC) molecule, such as MHC class I or MHC class II. Accordingly, peptides comprising at least 3 and preferably at least 4, 5, 6 or more consecutive amino acids of the disclosed oxygenase amino acid sequences may be employed as immunogens for producing antibodies.

Because naturally occurring epitopes on proteins frequently comprise amino acid residues that are not adjacently arranged in the peptide when the peptide sequence is viewed as a linear molecule, it may be advantageous to utilize longer peptide fragments from the oxygenase amino acid sequences for producing antibodies. Thus, for example, peptides that comprise at least 10, 15, 20, 25, or 30 consecutive amino acid residues of the amino acid sequence may be employed. Monoclonal or polyclonal antibodies to the intact oxygenase, or peptide fragments thereof may be prepared as described below.

A. Monoclonal Antibody Production by Hybridoma Fusion

Monoclonal antibody to any of various epitopes of the oxygenase enzymes that are identified and isolated as described herein can be prepared from murine hybridomas according to the classic method of Kohler & Milstein, *Nature* 256:495, 1975, or a derivative method thereof. Briefly, a mouse is repetitively inoculated with a few micrograms of the selected protein over a period of a few weeks. The mouse is sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA (enzyme-linked immunosorbent assay, as originally described by Engvall, *Enzymol.* 70:419, 1980, or a derivative method thereof. Selected positive clones can be expanded and their monoclonal antibody product harvested for use. Detailed procedures for monoclonal antibody production are described in Harlow & Lane, *Antibodies, A Laboratory Manual*, Cold Spring Harbor Laboratory, New York, 1988.

B. Polyclonal Antibody Production by Immunization

Polyclonal antiserum containing antibodies to heterogenous epitopes of a single protein can be prepared by immunizing suitable animals with the expressed protein, which can be unmodified or modified, to enhance immunogenicity. Effective polyclonal antibody production is affected by many factors related both to the antigen and the host species. For example, small molecules tend to be less immunogenic than other molecules and may require the use of carriers and an adjuvant. Also, host animals vary in response to site of inoculations and dose, with both inadequate or excessive doses of antigen resulting in low-titer antisera. Small doses (ng level) of antigen administered at multiple intradermal sites appear to be most reliable. An effective immunization protocol for rabbits can be found in Vaitukaitis et al., *J. Clin. Endocrinol. Metab.* 33:988-991, 1971.

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., in Wier (ed.), *Handbook of Experimental Immunology*, Chapter 19, Blackwell, 1973. A plateau concentration of antibody is usually in the range of 0.1 to 0.2 mg/mL of serum (about 12 µM). Affinity of the antisera for the antigen is determined by preparing competitive binding curves using conventional methods.

C. Antibodies Raised by Injection of cDNA

Antibodies may be raised against an oxygenase of the present invention by subcutaneous injection of a DNA vector that expresses the enzymes in laboratory animals, such as mice. Delivery of the recombinant vector into the animals may be achieved using a hand-held form of the "Biolistic" system (Sanford et al., *Particulate Sci. Technol.* 5:27-37, 1987, as described by Tang et al., *Nature* (London) 356:153-154, 1992). Expression vectors suitable for this purpose may include those that express the cDNA of the enzyme under the transcriptional control of either the human β-actin promoter or the cytomegalovirus (CMV) promoter. Methods of administering naked DNA to animals in a manner resulting in expression of the DNA in the body of the animal are well known and are described, for example, in U.S. Pat. No. 5,620,896 ("DNA Vaccines Against Rotavirus Infections"); U.S. Pat. No. 5,643,578 ("Immunization by Inoculation of DNA Transcription Unit"); and U.S. Pat. No. 5,593,972 ("Genetic Immunization"), and references cited therein.

D. Antibody Fragments

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178:476-496, 1989; Glockshuber et al. *Biochemistry* 29:1362-1367, 1990; and U.S. Pat. No. 5,648,237 ("Expression of Functional Antibody Fragments"); U.S. Pat. No. 4,946,778 ("Single Polypeptide Chain Binding Molecules"); and U.S. Pat. No. 5,455,030 ("Immunotherapy Using Single Chain Polypeptide Binding Molecules"), and references cited therein.

5. Taxol Production in vivo

The creation of recombinant vectors and transgenic organisms expressing the vectors are important for controlling the production of oxygenases. These vectors can be used to decrease oxygenase production, or to increase oxygenase production. A decrease in oxygenase production likely will result from the inclusion of an antisense sequence or a catalytic nucleic acid sequence that targets the oxygenase encoding nucleic acid sequence. Conversely, increased production of oxygenase can be achieved by including at least one additional oxygenase encoding sequence in the vector. These vectors can be introduced into a host cell, thereby altering oxygenase production. In the case of increased production, the resulting oxygenase may be used in in vitro systems, as well as in vivo for increased production of Taxol, other taxoids, intermediates of the Taxol biosynthetic pathway, and other products.

Increased production of Taxol and related taxoids in vivo can be accomplished by transforming a host cell, such as one derived from the *Taxus* genus, with a vector containing one or more nucleic acid sequences encoding one or more oxygenases. Furthermore, the heterologous or homologous oxygenase sequences can be placed under the control of a constitutive promoter, or an inducible promoter. This will lead to the increased production of oxygenase, thus eliminating any rate-limiting effect on Taxol production caused by the expression and/or activity level of the oxygenase.

6. Taxol Production in vitro

Currently, Taxol is produced by a semisynthetic method described in Hezari and Croteau, *Planta Medica* 63:291-295, 1997. This method involves extracting 10-deacetyl-baccatin III, or baccatin III, intermediates in the Taxol biosynthetic pathway, and then finishing the production of Taxol using in vitro techniques. As more enzymes are identified in the Taxol biosynthetic pathway, it may become possible to completely synthesize Taxol in vitro, or at least increase the number of steps that can be performed in vitro. Hence, the oxygenases of the present invention may be used to facilitate the production of Taxol and related taxoids in synthetic or semi-synthetic methods. Accordingly, the present invention enables the production of transgenic organisms that not only produce increased levels of Taxol, but also transgenic organisms that produce increased levels of important intermediates, such as 10-deacetyl-baccatin III and baccatin III.

7. Alternative Substrates for Use in Assessing Taxoid Oxygenases Activity

The order of oxygenation reactions on the taxane (taxadiene) nucleus en route to Taxol is not precisely known. However, based on comparison of the structures of the several hundred naturally-occurring taxanes (Kingston et al., *The Taxane Diterpenoids*, in Herz et al. (eds.), *Progress in the Chemistry of Organic Natural Products*, Springer-Verlag, New York, Vol. 61, p. 206, 1993; and Baloglu et al., *J. Nat. Prod.* 62:1448-1472, 1999), it can be deduced from relative abundances of taxoids with oxygen substitution at each position (Floss et al., *Biosynthesis of Taxol*, in Suffness (ed.), *Taxol: Science and Applications*, CRC Press, Boca Raton, Fla., pp. 191-208, 1995) that oxygens at C5 (carbon numbers shown in FIG.) and C10 are introduced first, followed by oxygenation at C2 and C9 (could be either order), than at C13. Oxygenations at C7 and C1 of the taxane nucleus are considered to be very late introductions, possibly occurring after oxetane ring formation; however, epoxidation (at C4/C20) and oxetane formation seemingly must precede oxidation of the C9 hydroxyl to a carbonyl (Floss et al., *Biosynthesis of Taxol*, in Suffness (ed.), *Taxol: Science and Applications*, CRC Press, Boca Raton, Fla., pp. 191-208, 1995). Evidence from cell-free enzyme studies with *Taxus* microsomes (Hezari et al., *Planta Medica* 63:291-295, 1997) and in vivo feeding studies with *Taxus* cells (Eisenreich et al., *J. Am. Chem. Soc.* 120:9694-9695, 1998) have indicated that the oxygenation reactions of the taxane core are accomplished by cytochrome P450 oxygenases. Thus, for example, the cytochrome P450-mediated hydroxylation (with double-bond migration) of taxadiene to taxadien-5α-ol has been demonstrated with *Taxus* microsomes (Hefner et al., *Chem. Biol.* 3:479-489, 1996). Most recently, the taxadien-5α-ol (and acetate ester) have been shown to undergo microsomal P450-catalyzed oxygenation to the level of a pentaol (i.e., taxadien-2α,5α,9α,10β,13α-pentaol) (Hezari et al., *Planta Medica* 63:291-295, 1997).

Because downstream steps are not yet defined, the above-referenced research summarized in Table 2 involved the pursuit of reactions (the timing and regiochemistry (position) of subsequent taxoid hydroxylations) through the use of surrogate substrates. Thus, labeled (+)-taxusin (the tetraacetate of taxadien-5,9,10,13-tetraol) was utilized to evaluate hydroxylations at C1, C2 and C7, and the epoxidation at C4/C20 en route to formation of the oxetane D-ring of Taxol.

Microsome preparations from *Taxus cuspidata* cells, optimized for cytochrome P450-mediated reactions, convert taxusin to the level of an epoxy triol (i.e., hydroxylation at C1, C2 and C7 and epoxidation of the C4/C20 double bond of the tetraacetate of taxadien-5,9,10,13-tetraol). Therefore, microsomal P450 reactions have been tentatively demonstrated for all of the relevant positions on the taxane core structure en route to Taxol (C1, C2, C5, C7, C9, C10 and C13, and the C4/C20 epoxidation), although the exact order for the various positions has not been established firmly.

The screening of the functionally expressed (by CO-difference spectra) clones in yeast (using taxadienol and taxadienyl acetate as test substrates) demonstrated that clone F14 encodes the cytochrome P450 taxane-10β-hydroxylase. Similar screening of functionally expressed clones using baculovirus-*Spodoptera* (especially for clones that do not express well in yeast) also revealed clone F16 as encoding the cytochrome P450 taxane-9α-hydroxylase.

The remaining regiospecific (positionally specific) oxygenases that functionalize the taxane core en route to Taxol can be obtained by identifying additional full-length clones by library screening with the appropriate hybridization probes or by RACE methods as necessary. Each clone can be functionally expressed (i.e., exhibiting a CO-difference spectrum which indicates proper folding and heme incorporation) in yeast or *Spodoptera*, as necessary. Each expressed cytochrome P450 clone can be tested for catalytic capability by in vivo (in situ) and in vitro (isolated microsomes) assay with the various taxoid substrates as described below, using GC-MS and NMR methods to identify products and thereby establish the regiochemistry of hydroxylation of the taxane core. Suitable substrates for use in additional assays are provided in Table 5, below.

TABLE 5

| Substrate | Use |
| --- | --- |
| Taxa-4(20),11(12)-dien (taxadiene) | A radiolabeled synthetic substrate employed to search for 5α-hydroxylase. |
| Taxa-4(20),11(12)-dien-5α-ol and the corresponding 5α-acetate (taxadienol and taxadienyl acetate) | Radiolabeled synthetic substrates employed to search for early hydroxylation steps and to assist in sequencing the various regiospecific hydroxylations of the Taxol pathway. These substrates were employed to confirm the taxane 10β-hydroxylase (clone F14) and the taxane 9α-hydroxylase (clone F16), and to indicate the early hydroxylation order as C5, C10 then C9. Preliminary evidence using these substrates suggests that clones F7, F9, F12 and F51 encode the C1, C2, C7 and C13 hydroxylases, but the corresponding products (four different diols (and diol monoacetates)) have not been identified and the sequence of oxygenation following 9α-hydroxylation is not yet known. |
| Taxa-4(20),11(12)-dien-2α,5α-diol (and diacetate ester) | Synthetic substrates used to search for the C1, C7 and C13 hydroxylases and to assist in ordering the C2, C9 and C10 hydroxylation reactions of the pathway. |
| Taxa-4(20),11(12)-dien-5α,9α,10β,13α-tetraol and corresponding tetraacetate (taxusin tetraol and taxusin, respectively) | Radiolabeled, semisynthetic substrates used to search for the C4/C20 epoxidase and late-stage oxygenations, including C1 and C7 hydroxylases and the C2 hydroxylase. Also used to assist in ordering the late-stage oxygenation steps of the pathway. Although taxusin (and tetraol) do |

TABLE 5-continued

| Substrate | Use |
|---|---|
| | not reside on the Taxol pathway (Floss et al., Biosynthesis of Taxol, in Suffness (ed.), Taxol: Science and Applications, CRC Press, Boca Raton, FL, pp. 191-208, 1995), this surrogate substrate is metabolized to the level of a presumptive taxadien-4,20-epoxy-1,2,5,7,9,10,13-heptaol (and tetraacetate) by microsomal preparations, but structures of the reaction products have not yet been confirmed by NMR. |
| *Taxa-4(20),11(12)-dien-5α,9α-diol (and monoacetate and diacetate) | Labeled biosynthetic substrates prepared from taxadienol (and acetate) using the above-described clones (clone 16). Used in searching for and ordering downstream oxygenation reactions. |
| *Taxa-4(20),11(12)-dien-5α,10β-diol (and monoacetate and diacetate) | Labeled biosynthetic substrates prepared from taxadienol (and acetate) using the above-described clones (clone 14). Used in searching for and ordering downstream oxygenation reactions. |
| Taxa-4(20),11(12)-dien-5α,9α,10β-triol (an acetate esters) | Semisynthetic substrate prepared from taxusin, and used as in * above. |

Using these natural and surrogate substrates, along with the established expression methods and bioanalytical protocols, it is anticipated that all of the regiospecific cytochrome P450 taxoid oxygenases of the Taxol pathway will be acquired from the extant set of related cytochrome P450s.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

The invention claimed is:

1. A plant cell transformed with a nucleic acid molecule comprising a nucleic acid sequence having at least 95% sequence identity with SEQ ID NO:82; wherein the nucleic acid sequence encodes a polypeptide having taxoid oxygenase activity.

2. The plant cell of claim 1, wherein the nucleic acid molecule further comprises a promoter sequence operably linked to the nucleic acid sequence.

3. The plant cell of claim 2, wherein the nucleic acid molecule comprises the nucleic acid sequence of SEQ ID NO:82.

4. A plant cell transformed with a nucleic acid molecule comprising a nucleic acid sequence that encodes a polypeptide comprising an amino acid sequence having at least 95% sequence identity with SEQ ID NO: 88; wherein the polypeptide has taxoid oxygenase activity.

5. The plant cell of claim 4, wherein the nucleic acid sequence encodes a polypeptide comprising the amino acid sequence of SEQ ID NO:88.

6. The plant cell of claim 4, wherein the nucleic acid molecule further comprises a promoter sequence operably linked to the nucleic acid sequence.

7. A method for producing a taxoid oxygenase, comprising growing a cell transformed with a nucleic acid molecule comprising a nucleic acid sequence having at least 95% sequence identity with SEQ ID NO:82, wherein the nucleic acid sequence encodes a polypeptide having taxoid oxygenase activity, and recovering from the cell the taxoid oxygenase encoded by the nucleic acid sequence.

8. A method for producing a taxoid oxygenase, comprising growing the plant cell of claim 4 and recovering from the plant cell the taxoid oxygenase encoded by the nucleic acid sequence.

* * * * *

SEQUENCE LISTING

```
<160> NUMBER OF SEQ ID NOS: 95

<210> SEQ ID NO 1
<211> LENGTH: 192
<212> TYPE: DNA
<213> ORGANISM: Taxus cuspidata

<400> SEQUENCE: 1
ccatttggag gaggacggcg gacatgtcca ggatgggaat acgcaaaagt ggaaatatta      60
ctgttcctcc atcattttgt gaaagcattc agtggttaca ccccaactga ccctcatgaa     120
aggatttgtg ggtatccagt ccctcttgtc cctgtcaagg gatttccaat aaaacttatc     180
gccagatcct ga                                                         192

<210> SEQ ID NO 2
<211> LENGTH: 192
<212> TYPE: DNA
<213> ORGANISM: Taxus cuspidata

<400> SEQUENCE: 2
cctttcggag gaggcatgcg tgtttgtcca gggtgggaat tcgccaagat ggagacatta      60
ctgtttctcc atcattttgt taaagccttc tctgggttga aggcaattga tccaaatgaa     120
aaactttcag ggaaaccact tcctcctctc cctgtcaatg ggcttcccat taaactctat     180
tccagatctt aa                                                         192

<210> SEQ ID NO 3
<211> LENGTH: 192
```

-continued

```
<212> TYPE: DNA
<213> ORGANISM: Taxus cuspidata

<400> SEQUENCE: 3
ccattcggag caggagtgcg catatgtgca ggatgggaat ttgcgaagac agaactatta     60
ctgtttgtcc atcactttgt taaaaacttc agaggttgca ttgtaattga tcctaatgaa    120
aaaatttcag gggatccatt ccctccactc cctaccagtg acaactcat gaaacttatt    180 ccgagatcat aa                                                         192

<210> SEQ ID NO 4
<211> LENGTH: 192
<212> TYPE: DNA
<213> ORGANISM: Taxus cuspidata

<400> SEQUENCE: 4
ccattcggag caggcgtacg catatgtgca ggatgggaat ttgcaaagac agaactatta     60
ctctttgtcc atcactttgt taaaaacttc agcggttgca ttgtaattga tcctagtgaa    120
aaaatttcag gggatccatt ccctcctctc cctaccagtg acaacgcat gaaacttatt    180 ccgagatcct aa                                                         192

<210> SEQ ID NO 5
<211> LENGTH: 192
<212> TYPE: DNA
<213> ORGANISM: Taxus cuspidata

<400> SEQUENCE: 5
cctttcgggg caggcaaacg catatgccca ggatgggagt tcgctaagtt ggagatgtta     60
ctgttcatcc atcattttgt caaaaatttc agcggatacc tcccacttga caccaaggaa    120
aagatctccg gagatccatt ccctcctctc cccaaaaatg gatttcccat taaactattt    180
ccgagaacct aa                                                         192

<210> SEQ ID NO 6
<211> LENGTH: 201
<212> TYPE: DNA
<213> ORGANISM: Taxus cuspidata

<400> SEQUENCE: 6
ccattcggag gaggcgcgcg cacatgccca ggatgggaat tttcaaagac ggagatatta     60
ctgttcatcc atcattttgt tagaactttc agcagctacc tcccagttga ctccaacgaa    120
aaaatttcag cagatccatt ccctcccctc cctgccaatg ggttctccat aaaacttttt    180
cccagatctc aatccaattg a                                               201

<210> SEQ ID NO 7
<211> LENGTH: 192
<212> TYPE: DNA
<213> ORGANISM: Taxus cuspidata

<400> SEQUENCE: 7
ccattcggag gaggcctgcg cacatgtcca ggatgggaat tctcaaagac ggagatatta     60
ctgtttatcc atcattttgt taaaactttc ggcagctacc tcccagttga ccccaacgaa    120
aaaatttcag cagatccatt ccctcctctc cctgccaatg gctttctat aaaacttttt    180 cccagatctt aa                                                         192

<210> SEQ ID NO 8
```

```
<211> LENGTH: 192
<212> TYPE: DNA
<213> ORGANISM: Taxus cuspidata

<400> SEQUENCE: 8
ccgttcggag gcggcctgcg catatgtcca ggatgggaat tgcaaagac agagatgtta      60 ctgtttatac attattttgt taaaactttc agcagctacg tcccagttga ccccaacgaa    120
aagatttcag cagatccgct cgcttcttcc cctgttaatg gattctccgt aaaactttt    180 ccaaggtcct aa                                                         192

<210> SEQ ID NO 9
<211> LENGTH: 192
<212> TYPE: DNA
<213> ORGANISM: Taxus cuspidata

<400> SEQUENCE: 9
ccatttggag caggcctgcg cgtatgtcca ggatgggaat tggctaagac ggagatatta     60
ctgtttgtgc atcattttgt taaaacgttc agtagctaca tacctgttga ccctaaagaa   120
aaactctcag ctgatccact tcctccgctc cctctcaatg ggttttccat taaactttt    180 tcgagatcct aa                                                         192

<210> SEQ ID NO 10
<211> LENGTH: 192
<212> TYPE: DNA
<213> ORGANISM: Taxus cuspidata

<400> SEQUENCE: 10
ccattcggag gaggcctgcg catctgtcca ggccgggaat tgcgaagat ggagatatta      60 gtgtttatgc atcattttgt taaagctttc agcagcttca ttccagttga ccctaacgaa   120
aaaatttcaa cagatccgct tccttccatc cctgtcaatg gattttccat aaaccttgtt   180
cccagatcct aa                                                         192

<210> SEQ ID NO 11
<211> LENGTH: 192
<212> TYPE: DNA
<213> ORGANISM: Taxus cuspidata

<400> SEQUENCE: 11
ccatttggag gaggcctgcg catctgtgca ggctgggaat tgcaaagat ggagatatta      60 ctgtttatgc atcattttgt taaaactttc agtcacttca ttccagttga ccccaacgaa   120
aagatttcga gagatccact gcctcccatc cctgtcaaag gattttccat aaagcctttt   180
cctagatcat aa                                                         192

<210> SEQ ID NO 12
<211> LENGTH: 192
<212> TYPE: DNA
<213> ORGANISM: Taxus cuspidata

<400> SEQUENCE: 12
cccttcggtg gaggccaacg gtcatgtgtg ggatgggaat tttcaaagat ggagatatta    60
ctattcgttc atcattttgt caaaactttt agcagctaca cccagttga tcccgacgaa    120 aaaatatcag gggatccact ccctcctctt ccttccaagg gattttccat taaactgttt   180
ccgagaccat ag                                                         192
```

<210> SEQ ID NO 13
<211> LENGTH: 192
<212> TYPE: DNA
<213> ORGANISM: Taxus cuspidata

<400> SEQUENCE: 13

```
ccatttggag gaggcctgcg cacatgtcca ggatgggaat tttcaaagat tgaaatatta      60
ctgtttgtcc atcatttcgt taaaaatttc agcagctaca ttccagttga tcccaatgaa     120
aaagttttat cagatccact acctcctctc cctgccaatg gattttccat aaaactttttt   180
ccgagatcct aa                                                        192
```

<210> SEQ ID NO 14
<211> LENGTH: 192
<212> TYPE: DNA
<213> ORGANISM: Taxus cuspidata

<400> SEQUENCE: 14

```
cccttcggag gagggagcg cacctgtcca ggatatgaat tttcaaagac tcatatatta      60
ctgttcatcc accaatttgt taaaactttc actggttaca tcccgcttga tccaaacgaa    120
agcatttcgg cgaatccgct cccccctcta cctgccaatg gatttcctgt aaacttttt   180
ctcaggtcct aa                                                        192
```

<210> SEQ ID NO 15
<211> LENGTH: 192
<212> TYPE: DNA
<213> ORGANISM: Taxus cuspidata

<400> SEQUENCE: 15

```
cccttcggcc agggtaatcg gatgtgcccc ggaaatgaat tcgcaaggtt ggaaatggaa      60
ttatttctat atcatttggt tttgagatat gattgggaat taatggaggc ggatgaacgc    120
accaacatgt acttcattcc tcaccctgtg cacagtttgc ctttactact taaacacgtt    180
cctcctacat ga                                                        192
```

<210> SEQ ID NO 16
<211> LENGTH: 154
<212> TYPE: DNA
<213> ORGANISM: Taxus cuspidata

<400> SEQUENCE: 16

```
ccatttggca agatttgaaa ttgctctctt tcttcacaac tttgtcacta aattcagatg      60
ggagcagctg gaaattgatc gtgcgactta ctttcctctt ccttccacag aaaatggttt    120
tccaatccgt ctctattctc gagtacacga atga                                154
```

<210> SEQ ID NO 17
<211> LENGTH: 210
<212> TYPE: DNA
<213> ORGANISM: Taxus cuspidata

<400> SEQUENCE: 17

```
ccgtttggtt cagggagaag aatgtgtccg ggcatgagtc tggcattgag tgttgttacg      60
tatacgctgg ggaggctgct gcagagcttc gagtggtctg ttccagaagg tgtgataatc    120
gacatgacgg agggtttggg actaacaatg cccaaagcag ttccgttgga gaccattatc    180
aaacctcgcc ttcccttcca tctctactga                                     210
```

<210> SEQ ID NO 18

```
<211> LENGTH: 202
<212> TYPE: DNA
<213> ORGANISM: Taxus cuspidata

<400> SEQUENCE: 18
cccttcggct gtatccggcg gggcctctgt tagttcctga tgaatcgaca gaggactgca      60
gtgtcggagg gtatcatgtc ccagcagtcg cgttcctgcg ggtacaacaa ttgacatgag     120
agagggtttt ggactcacaa tgcccaaagc gattccgttg aagccaata taaaacctcg     180 cctgcccttt catctctact ag                                              202

<210> SEQ ID NO 19
<211> LENGTH: 228
<212> TYPE: DNA
<213> ORGANISM: Taxus cuspidata

<400> SEQUENCE: 19 cccttttggtg gaggccagcg ttcatgtcca ggatgggaat tttcaaagat ggagattttta    60 ctgtcggtgc atcattttgt taaaacattc agcaccttca ccccagttga cccagcagaa    120
ataattgcaa gagattccct ctgccctctc ccttccaatg gttttctgt aaaacttttt     180 cctagatcct attcacttca cacaggcaac caggtcaaga aaatataa                  228

<210> SEQ ID NO 20
<211> LENGTH: 219
<212> TYPE: DNA
<213> ORGANISM: Taxus cuspidata

<400> SEQUENCE: 20
cccttcggag caggcgtgcg cacctgccca ggatgggaat tttcaaaaac ccagatatta     60
ctgttcttac attattttgt taaaactttc agtggctaca tcccactcga ccctgacgaa    120
aaagtgttag ggaatccagt ccctcctctc cctgccaatg gatttgctat aaaacttttc    180 cccaggcccct cattcgatca aggatcaccc atggaataa                           219

<210> SEQ ID NO 21
<211> LENGTH: 201
<212> TYPE: DNA
<213> ORGANISM: Taxus cuspidata

<400> SEQUENCE: 21 cctttttggtg cgggaaggag aggatgccca ggggcaagca tggccgttgt gacgatggaa     60
cttgcgttgg cacaactcat gcactgcttc cagtggcgca ttgaaggaga gttggatatg    120
agtgaacgct tcgcagcctc cttgcaaaga aaagtcgatc tttgtgttct tcctcaatgg    180
aggctaacta gtagcccttg a                                               201

<210> SEQ ID NO 22
<211> LENGTH: 63
<212> TYPE: PRT
<213> ORGANISM: Taxus cuspidata

<400> SEQUENCE: 22

Pro Phe Gly Gly Gly Arg Arg Thr Cys Pro Gly Trp Glu Tyr Ala Lys
 1               5                  10                  15

Val Glu Ile Leu Leu Phe Leu His His Phe Val Lys Ala Phe Ser Gly
            20                  25                  30

Tyr Thr Pro Thr Asp Pro His Glu Arg Ile Cys Gly Tyr Pro Val Pro
        35                  40                  45
```

-continued

Leu Val Pro Val Lys Gly Phe Pro Ile Lys Leu Ile Ala Arg Ser
        50                  55                  60

<210> SEQ ID NO 23
<211> LENGTH: 63
<212> TYPE: PRT
<213> ORGANISM: Taxus cuspidata

<400> SEQUENCE: 23

Pro Phe Gly Gly Gly Met Arg Val Cys Pro Gly Trp Glu Phe Ala Lys
 1               5                  10                  15

Met Glu Thr Leu Leu Phe Leu His His Phe Val Lys Ala Phe Ser Gly
            20                  25                  30

Leu Lys Ala Ile Asp Pro Asn Glu Lys Leu Ser Gly Lys Pro Leu Pro
        35                  40                  45

Pro Leu Pro Val Asn Gly Leu Pro Ile Lys Leu Tyr Ser Arg Ser
    50                  55                  60

<210> SEQ ID NO 24
<211> LENGTH: 63
<212> TYPE: PRT
<213> ORGANISM: Taxus cuspidata

<400> SEQUENCE: 24

Pro Phe Gly Ala Gly Val Arg Ile Cys Ala Gly Trp Glu Phe Ala Lys
 1               5                  10                  15

Thr Glu Leu Leu Leu Phe Val His His Phe Val Lys Asn Phe Arg Gly
            20                  25                  30

Cys Ile Val Ile Asp Pro Asn Glu Lys Ile Ser Gly Asp Pro Phe Pro
        35                  40                  45

Pro Leu Pro Thr Ser Gly Gln Leu Met Lys Leu Ile Pro Arg Ser
    50                  55                  60

<210> SEQ ID NO 25
<211> LENGTH: 63
<212> TYPE: PRT
<213> ORGANISM: Taxus cuspidata

<400> SEQUENCE: 25

Pro Phe Gly Ala Gly Val Arg Ile Cys Ala Gly Trp Glu Phe Ala Lys
 1               5                  10                  15

Thr Glu Leu Leu Leu Phe Val His His Phe Val Lys Asn Phe Ser Gly
            20                  25                  30

Cys Ile Val Ile Asp Pro Ser Glu Lys Ile Ser Gly Asp Pro Phe Pro
        35                  40                  45

Pro Leu Pro Thr Ser Gly Gln Arg Met Lys Leu Ile Pro Arg Ser
    50                  55                  60

<210> SEQ ID NO 26
<211> LENGTH: 63
<212> TYPE: PRT
<213> ORGANISM: Taxus cuspidata

<400> SEQUENCE: 26

Leu Ser Gly Ala Gly Lys Arg Ile Cys Pro Gly Trp Glu Phe Ala Lys
 1               5                  10                  15

Leu Glu Met Leu Leu Phe Ile His His Phe Val Lys Asn Phe Ser Gly
            20                  25                  30

Tyr Leu Pro Leu Asp Thr Lys Glu Lys Ile Ser Gly Asp Pro Phe Pro
        35                  40                  45

```
Pro Leu Pro Lys Asn Gly Phe Pro Ile Lys Leu Phe Pro Arg Thr
        50                  55                  60
```

<210> SEQ ID NO 27
<211> LENGTH: 66
<212> TYPE: PRT
<213> ORGANISM: Taxus cuspidata

<400> SEQUENCE: 27

```
Pro Phe Gly Gly Gly Ala Arg Thr Cys Pro Gly Trp Glu Phe Ser Lys
  1               5                  10                  15

Thr Glu Ile Leu Leu Phe Ile His His Phe Val Arg Thr Phe Ser Ser
             20                  25                  30

Tyr Leu Pro Val Asp Ser Asn Glu Lys Ile Ser Ala Asp Pro Phe Pro
         35                  40                  45

Pro Leu Pro Ala Asn Gly Phe Ser Ile Lys Leu Phe Pro Arg Ser Gln
     50                  55                  60

Ser Asn
 65
```

<210> SEQ ID NO 28
<211> LENGTH: 63
<212> TYPE: PRT
<213> ORGANISM: Taxus cuspidata

<400> SEQUENCE: 28

```
Pro Phe Gly Gly Gly Leu Arg Thr Cys Pro Gly Trp Glu Phe Ser Lys
  1               5                  10                  15

Thr Glu Ile Leu Leu Phe Ile His His Phe Val Lys Thr Phe Gly Ser
             20                  25                  30

Tyr Leu Pro Val Asp Pro Asn Glu Lys Ile Ser Ala Asp Pro Phe Pro
         35                  40                  45

Pro Leu Pro Ala Asn Gly Phe Ser Ile Lys Leu Phe Pro Arg Ser
     50                  55                  60
```

<210> SEQ ID NO 29
<211> LENGTH: 63
<212> TYPE: PRT
<213> ORGANISM: Taxus cuspidata

<400> SEQUENCE: 29

```
Pro Phe Gly Gly Gly Leu Arg Ile Cys Pro Gly Trp Glu Phe Ala Lys
  1               5                  10                  15

Thr Glu Met Leu Leu Phe Ile His Tyr Phe Val Lys Thr Phe Ser Ser
             20                  25                  30

Tyr Val Pro Val Asp Pro Asn Glu Lys Ile Ser Ala Asp Pro Leu Ala
         35                  40                  45

Ser Phe Pro Val Asn Gly Phe Ser Val Lys Leu Phe Pro Arg Ser
     50                  55                  60
```

<210> SEQ ID NO 30
<211> LENGTH: 63
<212> TYPE: PRT
<213> ORGANISM: Taxus cuspidata

<400> SEQUENCE: 30

```
Pro Phe Gly Ala Gly Leu Arg Val Cys Pro Gly Trp Glu Leu Ala Lys
  1               5                  10                  15

Thr Glu Ile Leu Leu Phe Val His His Phe Val Lys Thr Phe Ser Ser
```

```
                    20                  25                  30

Tyr Ile Pro Val Asp Pro Lys Glu Lys Leu Ser Ala Asp Pro Leu Pro
        35                  40                  45

Pro Leu Pro Leu Asn Gly Phe Ser Ile Lys Leu Phe Ser Arg Ser
    50                  55                  60

<210> SEQ ID NO 31
<211> LENGTH: 63
<212> TYPE: PRT
<213> ORGANISM: Taxus cuspidata

<400> SEQUENCE: 31

Pro Phe Gly Gly Gly Leu Arg Ile Cys Pro Gly Arg Glu Phe Ala Lys
1               5                   10                  15

Met Glu Ile Leu Val Phe Met His His Phe Val Lys Ala Phe Ser Ser
            20                  25                  30

Phe Ile Pro Val Asp Pro Asn Glu Lys Ile Ser Thr Asp Pro Leu Pro
        35                  40                  45

Ser Ile Pro Val Asn Gly Phe Ser Ile Asn Leu Val Pro Arg Ser
    50                  55                  60

<210> SEQ ID NO 32
<211> LENGTH: 63
<212> TYPE: PRT
<213> ORGANISM: Taxus cuspidata

<400> SEQUENCE: 32

Pro Phe Gly Gly Gly Leu Arg Ile Cys Ala Gly Trp Glu Phe Ala Lys
1               5                   10                  15

Met Glu Ile Leu Leu Phe Met His His

```
Ile Glu Ile Leu Leu Phe Val His His Phe Val Lys Asn Phe Ser Ser
            20                  25                  30

Tyr Ile Pro Val Asp Pro Asn Glu Lys Val Leu Ser Asp Pro Leu Pro
            35                  40                  45

Pro Leu Pro Ala Asn Gly Phe Ser Ile Lys Leu Phe Pro Arg Ser
    50                  55                  60
```

<210> SEQ ID NO 35
<211> LENGTH: 63
<212> TYPE: PRT
<213> ORGANISM: Taxus cuspidata

<400> SEQUENCE: 35

```
Pro Phe Gly Gly Gly Glu Arg Thr Cys Pro Gly Tyr Glu Phe Ser Lys
1               5                   10                  15

Thr His Ile Leu Leu Phe Ile His Gln Phe Val Lys Thr Phe Thr Gly
            20                  25                  30

Tyr Ile Pro Leu Asp Pro Asn Glu Ser Ile Ser Ala Asn Pro Leu Pro
            35                  40                  45

Pro Leu Pro Ala Asn Gly Phe Pro Val Lys Leu Phe Leu Arg Ser
    50                  55                  60
```

<210> SEQ ID NO 36
<211> LENGTH: 63
<212> TYPE: PRT
<213> ORGANISM: Taxus cuspidata

<400> SEQUENCE: 36

```
Pro Phe Gly Gln Gly Asn Arg Met Cys Pro Gly Asn Glu Phe Ala Arg
1               5                   10                  15

Leu Glu Met Glu Leu Phe Leu Tyr His Leu Val Leu Arg Tyr Asp Trp
            20                  25                  30

Glu Leu Met Glu Ala Asp Glu Arg Thr Asn Met Tyr Phe Ile Pro His
            35                  40                  45

Pro Val His Ser Leu Pro Leu Leu Lys His Val Pro Pro Thr
    50                  55                  60
```

<210> SEQ ID NO 37
<211> LENGTH: 50
<212> TYPE: PRT
<213> ORGANISM: Taxus cuspidata

<400> SEQUENCE: 37

```
His Leu Ala Arg Phe Glu Ile Ala Leu Phe Leu His Asn Phe Val Thr
1               5                   10                  15

Lys Phe Arg Trp Glu Gln Leu Glu Ile Asp Arg Ala Thr Tyr Phe Pro
            20                  25                  30

Leu Pro Ser Thr Glu Asn Gly Phe Pro Ile Arg Leu Tyr Ser Arg Val
            35                  40                  45

His Glu
    50
```

<210> SEQ ID NO 38
<211> LENGTH: 69
<212> TYPE: PRT
<213> ORGANISM: Taxus cuspidata

<400> SEQUENCE: 38

```
Pro Phe Gly Ser Gly Arg Arg Met Cys Pro Gly Met Ser Leu Ala Leu
1               5                   10                  15
```

-continued

Ser Val Val Thr Tyr Thr Leu Gly Arg Leu Leu Gln Ser Phe Glu Trp
            20                  25                  30

Ser Val Pro Glu Gly Val Ile Ile Asp Met Thr Glu Gly Leu Gly Leu
        35                  40                  45

Thr Met Pro Lys Ala Val Pro Leu Glu Thr Ile Ile Lys Pro Arg Leu
    50                  55                  60

Pro Phe His Leu Tyr
 65

<210> SEQ ID NO 39
<211> LENGTH: 66
<212> TYPE: PRT
<213> ORGANISM: Taxus cuspidata
<220> FEATURE:
<221> NAME/KEY: MISC_FEATURE
<222> LOCATION: (1)..(66)
<223> OTHER INFORMATION: "Xaa" equals any peptide

<400> SEQUENCE: 39

Leu Arg Leu Tyr Pro Ala Gly Pro Leu Leu Val Pro Asp Glu Ser Thr
 1               5                  10                  15

Glu Asp Cys Ser Val Gly Gly Tyr His Val Pro Xaa Xaa Xaa Val Pro
            20                  25                  30

Ala Gly Thr Thr Ile Asp Met Arg Glu Gly Phe Gly Leu Thr Met Pro
        35                  40                  45

Lys Ala Ile Pro Leu Glu Ala Asn Ile Lys Pro Arg Leu Pro Phe His
    50                  55                  60

Leu Tyr
 65

<210> SEQ ID NO 40
<211> LENGTH: 75
<212> TYPE: PRT
<213> ORGANISM: Taxus cuspidata

<400> SEQUENCE: 40

Pro Phe Gly Gly Gly Gln Arg Ser Cys Pro Gly Trp Glu Phe Ser Lys
 1               5                  10                  15

Met Glu Ile Leu Leu Ser Val His His Phe Val Lys Thr Phe Ser Thr
            20                  25                  30

Phe Thr Pro Val Asp Pro Ala Glu Ile Ile Ala Arg Asp Ser Leu Cys
        35                  40                  45

Pro Leu Pro Ser Asn Gly Phe Ser Val Lys Leu Phe Pro Arg Ser Tyr
    50                  55                  60

Ser Leu His Thr Gly Asn Gln Val Lys Lys Ile
 65                  70                  75

<210> SEQ ID NO 41
<211> LENGTH: 72
<212> TYPE: PRT
<213> ORGANISM: Taxus cuspidata

<400> SEQUENCE: 41

Pro Phe Gly Ala Gly Val Arg Thr Cys Pro Gly Trp Glu Phe Ser Lys
 1               5                  10                  15

Thr Gln Ile Leu Leu Phe Leu His Tyr Phe Val Lys Thr Phe Ser Gly
            20                  25                  30

Tyr Ile Pro Leu Asp Pro Asp Glu Lys Val Leu Gly Asn Pro Val Pro
        35                  40                  45

Pro Leu Pro Ala Asn Gly Phe Ala Ile Lys Leu Phe Pro Arg Pro Ser
        50                  55                  60

Phe Asp Gln Gly Ser Pro Met Glu
 65                  70

<210> SEQ ID NO 42
<211> LENGTH: 66
<212> TYPE: PRT
<213> ORGANISM: Taxus cuspidata

<400> SEQUENCE: 42

Pro Phe Gly Ala Gly Arg Arg Gly Cys Pro Gly Ala Ser Met Ala Val
 1               5                   10                  15

Val Thr Met Glu Leu Ala Leu Ala Gln Leu Met His Cys Phe Gln Trp
            20                  25                  30

Arg Ile Glu Gly Glu Leu Asp Met Ser Glu Arg Phe Ala Ala Ser Leu
        35                  40                  45

Gln Arg Lys Val Asp Leu Cys Val Leu Pro Gln Trp Arg Leu Thr Ser
    50                  55                  60

Ser Pro
 65

<210> SEQ ID NO 43
<211> LENGTH: 1455
<212> TYPE: DNA
<213> ORGANISM: Taxus cuspidata

<400> SEQUENCE: 43
atggatacct tcattcagca cgagtcttcc ccacttcttc tttctcttac tctcgctgtt      60
attcttggca caattcttct tttgatatta agtggtaaac agtacagatc ttctcgtaaa     120
cttccccctg aaacatggg cttccctctc attggggaga ctatagcact tatatcagat     180
acacctcgga agtttatcga cgacagagtg aagaaattcg gcctggtttt caagacttcg     240
ctaattggtc atcccgcagt tgtaatatgc ggctcctccg caaaccgttt cctcctctcc     300
aacgaggaaa agctggtgcg gatgtctttg cccaacgcag tactgaaact cttggggcag     360
gattgcgtta tggggaaaac cggagtggag catgggattg tacgtaccgc actagcccgc     420
gccttgggcc cccaggcgtt gcagaattat gtggccaaaa tgagttcaga gatcgaacac     480
catatcaacc aaaaatggaa ggggaaagat gaggtgaagg tgcttcctct gataagaagc     540
ctcgtcttct ccatttcaac cagcttgttt ttcggtataa acgatgagca ccaacagaag     600
cgacttcatc atcttttgga aactgtagct atgggacttg tgagtattcc cctagctttt     660
ccaggaactc gttttcgtaa agcactttac gcgcggtcga agctcgatga aattatgtct     720
tctgtaatag aaaggagaag aagcgatctt cgttcaggag cagcttcaag cgaccaagat     780
ctactgtcgg tgttggtcac cttcaaagat gaaagaggga attcattcgc agacaaggag     840
atactggata acttctcttt tctacttcac gccttatacg acaccacaat ttcaccactc     900
accttgatat ttaagctgct ctcctctagt cctgaatgct atgagaatat agctcaagag     960
cagctggaaa tacttggcaa taaaaaggat agagaggaaa tcagctggaa ggatctgaag    1020
gatatgaaat acatggca agcagttcag gaaactttga ggatgttccc tccagtttat    1080
ggatatattc gcgaggcttt gacagatatt gactatgatg ctatacaat accaaaagga    1140
tggagaaat tatgttcacc tcatactacg catagtaaag aggagtattt cgatgagccg    1200
gaagaattca gaccttcaag attcgaggat caaggaaggc atgtggctcc ttacacattc    1260

```
ataccatttg gaggaggcct gcgcatctgt gcaggctggg aatttgcaaa gatggagata    1320
ttactgttta tgcatcattt tgttaaaact ttcagtcact tcattccagt tgaccccaac    1380
gaaaagattt cgagagatcc actgcctccc atccctgtca aggattttc cataaagcct    1440 tttcctagat cataa                                                    1455

<210> SEQ ID NO 44
<211> LENGTH: 1455
<212> TYPE: DNA
<213> ORGANISM: Taxus cuspidata

<400> SEQUENCE: 44
atgcttatcg aaatggatac cttcgttcag ctcgagtctt ccctgttct tctttccctt    60 accctcacac ttattcttct ttttatattc tgtagtaaac aatacagatc ctctcttaaa    120 cttcccctg gaaacatggg cttccctctc attggggaga cgatagcact ggcatcacag    180
acacctgata aattttcgg cgatagaatg aagaaattcg gcaaggtttt caagacttcg    240
ttaattgggc atcccacaat tgtgctctgc ggttcctccg gaaaccgttt tctcctctcc    300
aacgaggaaa aactggtgcg gatgtttccg cccaactcat ccagcaaact cctggggcag    360
gattctgttc tggggaaaat aggagaggag catcggattg tacgtaccgc actagcccgc    420
tgtttgggcc cccaagcgct gcagaattac gtgtccaaaa tgagttcaga gatccaacgt    480
catatcaacc aaaaatgga gggaaaaggt gaagtgaaga tgcttcctct gataagaagc    540
cttgtcttct ccatcgcaac cagcttattt tttggtatta ccgatgagca acaacaagaa    600
cgacttcatc atcttctgga aacagttgtt acgggacttt tgtgtattcc gctcgacttt    660
ccaggaacta catttcgtaa agcacttcac gcgcggtcga agctcgatga gattatgtct    720
tctgtaatag aaaggagaag aaacgatctg cgtttaggcg cagcttcaag cgaccaagat    780
ctattgtcgg tgttgctcac cttcaaagat gaaagaggga atccattcgc tgacaaggag    840
atcctggata acttctcttt tctacttcat gccttatacg acaccacaat ttcaccactc    900
acgttggtat ttaagctggt gtcctccaat cctgaatgct acgaaaatat agctcaagag    960
caattggaaa ttcttcgcaa taaaaaggat ggagaagata tcagctgggc ggatctgaag    1020
gatatgaaat atacgtggca agcagttcag gaaaccttga ggatgtgtcc tccagtttac    1080
ggaaattttc gcaaggcttt gacagatatt cattatgatg gctatacaat cccaaaagga    1140
tggaggattt tatgttcacc ttatactaca catagtaaag aggagtattt tgacgacccg    1200
gagaaattca gaccttcaag attcgaagag caaggaaggg atgtggctcc ttacacattc    1260
ataccattcg gaggaggcct gcgcatctgt ccaggccggg aatttgcgaa gatggagata    1320
ttagtgttta tgcatcattt tgttaaagct ttcagcagct tcattccagt tgaccctaac    1380
gaaaaaattt caacagatcc gcttccttcc atccctgtca atggattttc cataaacctt    1440
gttcccagat cctaa                                                    1455

<210> SEQ ID NO 45
<211> LENGTH: 1506
<212> TYPE: DNA
<213> ORGANISM: Taxus cuspidata

<400> SEQUENCE: 45
atggattcct tcagttttct aaaaagcatg gaagcgaaat cggccaagt catacaccgg    60 gatcagtctt ccagtactgc tcttctgtcc ctcgcattca cagctgctgt tgccattttt    120
```

-continued

```
cttgtgttgc tctttcgatt taaaagccgg ccctctacta atttccctcc aggaaatttt       180
ggcttcccct tcattggaga gacgatacag ttcttgcggg cacttcgatc agaatcgcct       240
catatgtttt ttgatgagag attgaagaaa tttgggcgtg tattcaagac gtcattaact       300
gggcatccca cagctgtgtt ctgcgggcct gcgggaaacc ggtttattta ctcgaatgag       360
cacaagctgg tgcagtcgtc tgggcccaac tccttcgtca aactggttgg gcagcaatcc       420
atcgtgacca aaacaggaga ggagcaccgc atctttcttg gtgtcctgaa cgagtttctg       480
gggcctcatg ccttacagag ttatacgcct aaaatgagtt ccaaaatcca ggagaatatc       540
aataagcatt ggaagggtaa agatgaagtg aacatgcttc cttcgataag acagctcgtc       600
ttctccattt caagcagctt gttttttgat attaatgatg aggatcaaca ggaacaactt       660
aaaactcttt tagaaactat tcttgtggga actttgtcgg ttcccctcga cattccagga       720
tctaattttc gtaaagctct tcgggcgcgt tccaagctgg atgaaattct gtctcgttta       780
atcgaaagca aagaaaaga tatgcgttct gggatagctt ctaccagtaa aaatctactg       840
tcggtgctgc tcgccttcaa agatgaaaga gggaatccat tgacggacac ggagatcctc       900
gacaactttt cttttatgct tcacgcctca tacgacacca ccgtttcgcc cacagtttgt       960
atatttaagc tgctctccgc caatccagaa tgctatgaaa agtagttca agaacaattg      1020 ggaatacttg gcaataaaaa ggacggtgaa gaaatgtgtt ggaacgatct gaaagctatg      1080
aaatatacat ggcaagcagc tcaagaaaca atgaggcttt ccctccagc gtttggatca      1140 tttcgcaagg tcatcgccga tattcatcat gatggctata taattcccaa aggatggaaa      1200
gctatggtga caaattacag tacaagtagg aaagaagagt acttcgatga accagacaat      1260
ttcaagccct tcaagatttgg ggatggaaag tatgtggctc cgtacacatt cttacctttc      1320
ggggcaggca tacgcatatg cccaggatgg gagttcgcta agttggagat gttactgttc      1380
atccatcatt ttgtcaaaaa tttcagcgga tacctcccac ttgacaccaa ggaaaagatt      1440
tccggagatc cattccctcc tctccccaaa aatggatttc ccattaaact atttccgaga      1500
acctaa                                                               1506
```

<210> SEQ ID NO 46
<211> LENGTH: 1503
<212> TYPE: DNA
<213> ORGANISM: Taxus cuspidata

<400> SEQUENCE: 46

```
atggatgccc tttctcttgt aaacagcaca gttgcaaaat ttaatgaggt aacgcagcta        60
caggcttccc ctgctattct gtccactgcc ctcactgcta ttgcaggcat tattgtgctc       120
ctcgtcatca cttctaaacg ccgttcctct cttaaacttc ctcctggaaa actaggcctc       180
cctttcattg gcgagacttt agagttcgtg aaggctcttc gatcagacac acttcgacaa       240
tttgtggagg aaagggaggg gaaatttgga cgtgtgttca agacttcatt gcttgggaag       300
cccactgtaa tactctgcgg ccctgcggga aaccgcttag ttctttccaa cgaggaaaaa       360
ctgttgcacg tgtcgtggtc cgcccaaatt gccagaatcc tgggtctcaa ttctgttgca       420
gtgaaaaggg gagatgatca ccgcgttctg cgtgtcgcac tagcaggttt ttttgggctct       480 gcagggctac agctttacat aggtaaaatg agtgcactta tcagaaatca tatcaatgaa       540
aaatggaagg gaaaagatga agtgaatgta ctgagtttgg taagagatct tgtcatggac       600
aattcagcta tcttgttttt caatatatac gataaagagc gaaagcaaca actgcatgaa       660
atattgaaaa tcattcttgc ctcacatttc ggcatacctt taaacattcc cggatttctg       720
```

```
tatcgcaaag cactcaaggg gagcttgaag cggaaaaaaa ttctctccgc tttactggaa      780
aagagaaaag acgaactgcg ctcaagatta gcgtctagca atcaagatct tctctctgtt      840
ttgctcagct tcagagatga aagagggaaa ccactgagcg acgaggcagt cttagacaac      900
tgttttgcaa tgctggatgc ctcctatgac accaccactt cacaaatgac tctgatttta      960
aagatgttgt cttccaatcc agaatgcttt gaaaaagtag ttcaagagca attggagata     1020
gcgtcaaata aaaggaggg agaagaaatc acaatgaagg atatcaaagc catgaaatac      1080
acatggcaag tgctccagga aagtctacgg atgctttctc cagtatttgg aacacttcgt     1140
aagaccatga atgacattaa tcacgatggt tacacaattc aaaaggatg gcaggttgta      1200 tggacaactt attctacaca tcagaaagac atatatttca agcagccaga taaattcatg     1260
ccttcgagat tcgaagagga agatgggcat ttggatgctt atacattcgt accatttgga     1320
ggaggacggc ggacatgtcc aggatgggaa tacgcaaaag tggaaatatt actgttcctc     1380
catcattttg tgaaagcatt cagtggttac accccaactg accctcatga aaggatttgt     1440
gggtatccag tccctcttgt ccctgtcaag ggatttccaa taaaacttat cgccagatcc     1500
tga                                                                    1503

<210> SEQ ID NO 47
<211> LENGTH: 1476
<212> TYPE: DNA
<213> ORGANISM: Taxus cuspidata
<220> FEATURE:
<221> NAME/KEY: misc_feature
<222> LOCATION: (1)..(1476)
<223> OTHER INFORMATION: "n" equals any oligonucleotide

<400> SEQUENCE: 47
atggatacca tacgagcaag ttttggcgaa gttattcagc cagagtattc tcctctcatc       60
atttccgncg ctctggcagc ttttcttggt attgttattt tctcgatctt cagttccact      120
cgacgatcct atgtgaatct cccccctgga aatttaggtt tacctttcat tggcgagacg      180
atacagttct tgggggcact tcagtcagaa aaaccccata cattttttcga tgagagagtg     240 aagaaattcg gtaaggtctt caagacttct ctaattgggg atcccacggt ggtactctgc      300
gggccggcgg gaaaccgctt agttctgtcg aacgaagaca agctggtgca gtccgcaggg      360
cccaagtctt tcctgaaact gtttggggag gattccgttg cggccaaaag agaagagagc      420
catcgcatct tacgttcggc tctgggtcga tttctgggtc cccatgcttt acagaattat      480
attgggaaaa tgaattcaga aatgcaacgn catttcgatg acaaatggaa gggaaaagat      540
gaggtgaagg tgcttccttt ggttagaggc ctcattttct ccattgctac ctccctgttc      600
ttcaatataa atgatgacag acaacgtgag caactccatg gtctgctgga tacaatactt      660
gtgggaagta tgactattcc tctgaacatt ccaggaactc tttttcgtaa agctgtcaag      720
gcacgggcga agctggacga aattcttttt gctttgatag agaacagaag aagagagctg      780
agatcgggcc taaattctgg taatcaagat cttctgtcgt ccttgctcac cttcaaagat      840
gaaaaaggga atccactgac agacaaggag atcctcgaca acttctctgt tatgcttcat      900
gcctcgtatg acactactgt ttcaccaacg gtcttgatat tgaagcttct cgcctccaat      960
cctgaatgct atgaaaaagt tgttcaagag cagttgggaa tacttgctag taaaaaggag     1020
ggagaagaag tcaattggaa ggatctgaaa gctatgccat atacatggca agcaattcag     1080 gaaccccctaa gnatgccccn ccagcttttg gaatgtttcg aagagctttc cctgatattc     1140
```

```
agttggaagg ctatacaatt ccaaaaggat gggcaattgt gtggccanct tatagtcaat    1200
gggagagaag agttcttcaa tgaaccagac aaattcaagc cttccagatt cgaggaagga    1260
aagcccctgg atccttacac attcatacca ttcggagcag gggtacgcat atgtgcagga    1320
tgggaatttg caaaggctga actattactg tttgtccatc cctttgttaa aaacttcagc    1380
ggttgcatta taattgatcc gaatgaaaaa atttcagggg atccattccc tccactccct    1440
accagtggac aactcatgaa acttattccg agatca                              1476
```

<210> SEQ ID NO 48
<211> LENGTH: 1503
<212> TYPE: DNA
<213> ORGANISM: Taxus cuspidata
<220> FEATURE:
<221> NAME/KEY: misc_feature
<222> LOCATION: (1)..(1503)
<223> OTHER INFORMATION: "n" equals any oligonucleotide

<400> SEQUENCE: 48

```
atggatagct tcaatttctt gagaggcatt ggagcagatt ttgggggatt cattcagttc      60
cagtcttccc ctgctgttct ttcccttttcc ctgatcacaa ctattcttgg cgttctactt    120
ctctggttct tccttcataa aaacggttcc tctgttactc tcccccctgg aaatttaggc    180 ttcccttttca ttggggagac cataccattc ttgaggcac ttcgatcaga aacacctcag    240
acgttttttg atgagagggt gaagaaattc ggtgttgtat tcaagactcg gatagttggg    300
catcccacag ttgtactctg cgggcctgag ggaaaccgct tcttctctc caacgaggac    360 aaactggtgc aggcgtcatt gcccaactct tccgagaaac taattgggaa atattccatt    420
ctgtccaaaa gagggggagga gcatcgcata ttacgtgctg cacttgcccg cttttttgcga    480 cccccaagctt tgcagggtta tgttgctaaa atgagttcag aaatccaaca tcatatcaag    540
caaaaatgga agggaaatga tgaagtgaag gtgcttcctc tgataagaac cctgatcttc    600
aacattgcaa gcagcctgtt tttcggcata aatgatgaac caacagga acagcttcat      660 catcttttgg aagccattgt tctgggaagt ctgtctgttc cgctcgactt tccaggaact    720
cgttttcgta aagctcttga tgcgcggtct aagctggatg agattctttc ttctttaatg    780
gagagcagaa gaagggatct gcgtttgggc acggcttctg agaatcaaga tcttcttttct    840 gtgttgctca ccttcaaaga tgaaagaggg aatccactca cagacaagga aatcttcgac    900 aattttttcat ttatgcttca tgcctcgtat gataccactg tttcaccaac ggggtttgatg    960 cttaagcttc tcttctctag tcctgattgc tatgaaaaac tagttcaaga acaattggga   1020
atagttggca ataaaaagga gggagaagaa atcagctgga acgatctgaa agctatgaaa   1080
tatacatgca aggttgtgca ggaaagtatg aggatgctcc ctccagttttt tggatcgtat   1140 cgcaaggcta ncacctatat ccattatgat gggtatacaa ttccaaaagg atggaatata   1200
ttctggtcac cttatactac acacgggaaa gaagaatact tcaatgaagc ggacaagttc   1260
atgccttcga gattcgagga aggcaaatat gttgctcctt acacattctt gccattcgga   1320
gcaggtctgc gcgtatgtcc aggatgggaa tttgcaaaga ccgagatatt actgttcgtc   1380 catcattta ttacaacttt cagcagctac atcccaattg accccaaaga taaaatttca   1440
ggggatccat ttcctcctct gcctaccaat ggatttttcca tgaaacttttt taccagatct   1500 taa                                                                 1503
```

<210> SEQ ID NO 49
<211> LENGTH: 1452

<212> TYPE: DNA
<213> ORGANISM: Taxus cuspidata

<400> SEQUENCE: 49

```
atggatacct taattcagat ccagtcttcc cctgatttcc tttcctttac tctcacagcg      60
tttctgggcg ttgttgtgct tttgatattc cgttataaac accgatccgc tctcaaactt     120
ccacctggaa atttaggctt gcccttcatt ggggagacaa taacatttgc atctcaacct     180
cctcagaagt ttttaaacga gaggggaag aaatttggtc ctgttttcaa gacgtcgcta      240
attgggcatc ccacagttgt tctctgcggc tcctcgggaa accgttttct cctctccaac     300
gaggaaaagc tggtgcggat gtcttttgccc aactcataca tgaaactcct ggggcaggat    360
tcccttctgg ggaaaacggg acaggaacat cggattgtgc gtaccgcact aggacgtttt    420
ttgggccccc aagagttgca gaatcatgtg gccaagatga gttcagacat tcagcatcac    480
atcaaccaaa aatggaaggg gaatgatgaa gtgaaggtgc ttcctctgat aaggaacctt    540
gtcttctcca ttgcaaccag cttgtttttc ggtataaacg atgagcacca acaggagcga    600
cttcatcttc ttttggaaac tattgtaatg ggagctgtgt gtattccgct cgcctttcca    660
ggatctggtt ttcgtaaagc gcttcaggca cggtcggagc tcgatggaat tctcattctt   720
ttaatgaaaa tcagaagaag cgatctgcgt tcaggcgcag cttcaagcaa ccaagatcta    780
ctgtcggtgt tgctcacctt caaagatgaa agaggaaatc cattgacaga caaggagatc    840
ctcgacaact tctctgttct acttcatggc ttatatgaca ccacaatttc accactcacc    900
ttgatttta agctcatgtc ctccaatact gaatgctacg agaatgtagt ccaagagcaa     960
ttagaaatac tttcccatag agagaaggga gaggagatcg gttggaagga tctgaaatct   1020
atgaaatata cttggcaagc cattcaggaa accttgagaa tgttccctcc ggtttacgga   1080
aattttcgca aggctttgac tgatattcat tacgatggct atacaatccc aaaagggtgg   1140
agggttttat gttcgccttt taccacgcac agcaatgaag aatatttaa tgagccagat   1200
gaattcagac cttcaagatt cgaggggcaa ggaaagaatg tgccttctta cacattcata   1260
ccgttcggag gcggcctgcg catatgtcca ggatgggaat ttgcaaagac agagatgtta   1320
ctgtttatac attattttgt taaaactttc agcagctacg tcccagttga ccccaacgaa   1380
aagatttcag cagatccgct cgcttctttc cctgttaatg gattctccgt aaaacttttt   1440
ccaaggtcct aa                                                        1452
```

<210> SEQ ID NO 50
<211> LENGTH: 1512
<212> TYPE: DNA
<213> ORGANISM: Taxus cuspidata
<220> FEATURE:
<221> NAME/KEY: misc_feature
<222> LOCATION: (1)..(1512)
<223> OTHER INFORMATION: "n" equals any oligonucleotide

<400> SEQUENCE: 50

```
atggacgctt ttaatatttt aaagggccct gctgcaaaac ttaatggagt cgtgcagctc      60
ggctcttaca ccgatcgtat tctttccatt acagtcgttg ccttcattac tattctcctg     120
ttgctcatgc tccgttggaa aagccagtct tctgtgaagc ttccccccggg gaactttggc    180
ttccctttga tcggcgaaac attacaattg ttgagggcat ttcgatctaa cacgactcaa     240
cagttttttg atgagaggca aaaaaaattt ggttgtgttt tcaagacatc actagtcgga    300
gaacgcacgg tagtactctg cggtccgtct ggaaaccgtt tagtgctcgc caaccagaac     360
```

```
aaggtggtgg agtcatcgtg gccgagcgct tcatcaaac tcatcggaga ggattccatt      420
gccaacacaa acgagagaa gcatcggatc ttacgcgccg cactgcttag atatcttggt      480
cccgggtcgt tacagaatta tgtggggaaa atgaggtcag aaatcgaaca tcatatcaat    540
gagaaatgga agggaaaaga tgaagtgaag gtgctcgatt tggtaagaaa gaatgtcttc     600
tccgttgcaa ccgccttgtt tttcggtgtn aatgacgagg aaagaaaaag gatccgacct     660
ccatcaatct tgcggaaact gcactttgcg ggcagttttt ctattccgct ggactttcca    720
ggaactagtt atcggagagc tctggaggca cggttgaagc tggataaaat cctctcttct    780
ctgatagaaa ggagaagaag cgatctgcgc tcgggcttgg catctggtaa tgaggatctg    840
gtctccgtgt tgctcacctt caaagacgaa ggaggaaatc ctctgacaga caaggagatc    900
ctcgataatt tctccgggct acttcacgca tcgtatgaca ccacaacttc agcactcacc    960
ttgacattca agctcatgtc ctcctctgct gaatgctatg acaaagtagt tcaagagcaa   1020
ctgagaatag tttccaataa aaaggaggga gaagaaatca gcttgaaaga tctgaaagac   1080
atgaaatata catggcaagt ggtgcaggaa actctgagga tgttccctcc gcttttcgga   1140
tcatttcgga agaccatcgc cgacattcag tacgatggct atacaattcc aaaaggatgg   1200
aaagttttat gggcaactta taccacacat gggagagatg agtatttcag tgagccccaa   1260
aaattcaggc cttcgagatt cgaagaggga ggaaagcatg tggctcctta cacattcttg   1320
cccttcgaag gaggggagcg cacctgtcca ggatatgaat tttcaaagac tcatatatta   1380
ctgttcatcc accaatttgt taaaactttc actggttaca tcccgcttga tccaaacgaa   1440
agcatttcgg cgaatccgct ccccccctcta cctgccaatg gatttcctgt aaaactttt    1500
caaaggtcct aa                                                        1512

<210> SEQ ID NO 51
<211> LENGTH: 1494
<212> TYPE: DNA
<213> ORGANISM: Taxus cuspidata

<400> SEQUENCE: 51
atggatagct tcatttttct gagaagcata ggaacaaaat ttgggcagct ggagtcttcc     60
cctgctattc tttcccttac cctcgcacct attctcgcca ttattcttct cttgctcttc    120
cgttacaatc accgatcctc tgttaaactt cccctggaa agttaggttt tcctctcatc     180
ggggagacca tacaattatt gcggacactc cgatcagaaa cacctcaaaa gttttttgat    240
gatagattga agaaattcgg tcctgtttac atgacttccc taattgggca tcccacagtt    300
gtactctgcg ggcctgcggg aaacaaatta gttctttcga acgaggacaa gctggtagag    360
atggaagggc ccaagtcttt catgaaactg attggggaag attccattgt tgctaaaaga    420
ggcgaggatc atcgcatctt acgcactgca cttgctcggt ttttgggcgc tcaagctttca   480
caaaattatc tgggtagaat gagttcagaa ataggacacc atttcaatga aaatggaag     540
ggtaaagatg aagtgaaggt gcttcctttg gtaagagggc ttatcttctc cattgcaagc    600
accctgtttt tcgatgtaaa tgatggacac caacagaagc aacttcatca tcttctggaa    660
actattcttg tgggaagttt gtcagtcccg ctggactttc aggaactcg ttatcgtaaa    720
gggcttcagg cgcggctgaa gcttgatgaa attctctcct ctctaataaa acgcagaaga    780
agagatctgc gttcaggcat agcttctgat gatcaagatc tactgtcggt gttgctcacc    840
ttcagagatg aaaaagggaa ctcactgaca gaccagggga ttctggacaa cttttctgct    900
atgtttcatg cttcatatga caccactgtt gcaccaatgg ccttgatatt taagcttcta    960
```

```
tactccaatc ctgaatacca tgaaaaagta tttcaagagc agttggaaat aattggcaat      1020
aaaaaggaag gggaagaaat cagttggaag gatttgaaat ctatgaaata tacatggcaa      1080
gcagttcaag aatcactacg aatgtaccca ccagttttttg gaatatttcg taaggctatc     1140
actgatattc attatgatgg gtatacaatt ccaaaaggat ggagggtttt atgttcacct      1200
tatactacac atctgagaga agagtacttc cctgagcctg aagaattcag gccttcaaga     1260
tttgaggatg aaggcaggca tgtgactcct tacacatatg taccatttgg aggaggcctg     1320
cgcacatgtc caggatggga attttcaaag attgaaatat tactgtttgt ccatcatttc      1380
gttaaaaatt tcagcagcta cattccagtt gatcccaatg aaaaagtttt atcagatcca     1440
ctacctcctc tccctgccaa tggattttcc ataaaacttt ttccgagatc ctaa             1494

<210> SEQ ID NO 52
<211> LENGTH: 1524
<212> TYPE: DNA
<213> ORGANISM: Taxus cuspidata
<220> FEATURE:
<221> NAME/KEY: misc_feature
<222> LOCATION: (1)..(1524)
<223> OTHER INFORMATION: "n" equals any oligonucleotide

<400> SEQUENCE: 52
atggaaacta aatttgggca acttatgcag ctngagtttc ttcccttttat cctcacacct       60 attctcggcg cccttgttct ctccatctc ttccgtcata gaaaccgatc ctctgttaaa       120
cttccacctg gaaagttagg tttccccgtc attggggaga cgatacagtt cctgagggca     180
cttcgatcac aaacacctca aaagttttttc gatgatagag tgcagaaatt tggtggtgtt      240
ttcaagactt cactaattgg aaatccccta gtggtcatgt gcgggcctgc gggaaaccgg     300
ttagttctgt ccaacgagga caagcttgtg cagttggaag cgcccaattc cttgatgaaa     360
ctgatggggc aggactccct cctggccaaa agacaagagg accaccgcac cttacgtgct      420
gcactagccc ggttttttagg cccccaagct ctacanaatt atatgactaa atcagttca      480 agaaccgaac atcatatgaa tgaaaaatgg aaggaaaag atgaagtgag gacgcttcct       540
ttgataagag agctcatctt ctccaatgca agcagcttgt ttttcgatat caatgatgag      600
caccaacagg agcgacttca tcatcttttg gaagctgttg ttgttggaag tatgtctatt       660
ccgctggact ttccaggaac tcgcttacgt aaagcccttc aggcgcgatc taagctggat     720
gaaattctct cctctttaat aaaaagcaga gaaaagatc ttgtttcagg atagcttct        780 gatgatcaag atctactgtc ggtgttgctc accttcaaag acgagagagg aaatccactg     840
accgacaaag agatcctcga caactttttct cttctgcttc atgcctcgta tgacaccact     900
gtttccccaa tggttttgac attgaagctc ctctctcca atccagaatg ctatgaaaaa       960
gtagttcaag agcaattggg aatagttgcc aataaaagga taggaagaa aatcagctgg       1020 aaggatttga aagccatgaa atacacatgg caagtagttc aggaaacact gagaatgttc     1080
cctccacttt ttggatcatt tcgcaaggct atggttgata ttgattatga tggctacaca     1140
attccgaaag gatggatgat tttatggaca acttacggta cacacctgag agaagagtac     1200
ttcaatgaac cgttgaaatt taggccttca agatttgaag aagacgggcg tgtgactcct      1260
tacacattca taccattcgg aggaggcgcg cgcacatgcc caggatggga attttcaaag      1320
acggagatat tactgttcat ccatcatttt gttagaactt tcagcagcta cctcccagtt     1380
gactccaacg aaaaaatttc agcagatcca ttccctcccc tccctgccaa tgggttctcc     1440
```

```
ataaaacttt cagcagatcc attccctccc ctccctgcca atgggttctc cataaaactt   1500
tttcccagat ctcaatccaa ttga                                          1524

<210> SEQ ID NO 53
<211> LENGTH: 1539
<212> TYPE: DNA
<213> ORGANISM: Taxus cuspidata
<220> FEATURE:
<221> NAME/KEY: misc_feature
<222> LOCATION: (1)..(1539)
<223> OTHER INFORMATION: "n" equals any oligonucleotide

<400> SEQUENCE: 53
atggcttatc cggagttgct cgaaaattta tcgggagacc gagctcaatc tccagcaata     60
gccgcggtgc ttacaatttt attcttgttg gggattttct acatactgcg cgggctgaga    120
aacaatggaa gaagattgcc ccccggccca attccatggc cgatcgtggg aaatctccac    180
cagttgggaa agcttcccaa ccgtaatctg aagagctcg caaagaaaca cggacccatc     240
atgctcatga aattgggttc cgttcctgcc gttatcgttt cttcctctgc catggcaaaa    300
gaagttctga aaactcatga tctggttttc gccagccgac ccgaaagcgc cgcaggaaaa    360
tacatagcgt ataattacaa ggatatagtt ttctctccct acggacctta ctggagacag    420
atgaagaaaa tatgcgtggt ggaattgttg aatgccagaa gaatcgagtc gttgagatcc    480
gtaagagagg aagaggtgtc tgttataatt cgttcggtgt gggagaagag caagcagggt    540
gcggtcgccg tcaatctgag caagacgctg tcatcccctta cagggact catgttgcag     600 atcttttcca gtaacgatga cggcgggaat agcagcgtca ccgccattaa agaaatgatg    660
tcggaggtgt ctgagacggc gggagctttt aacattggag attatttcc atggatggac     720 tggatggatt tgcagggtat acagcggcgc atgacgaagg cacacgatta tttcgaccag    780
gtcattacga aaattatga gcaacaccag aggacgagag cgatggagga cactcaacaa     840
ccaaaagaca taattgacgc cctgttgcag atggagaaca ccgatggcgt caccatcaca    900
atggaaaata tcaaagccgt cgttttgggt attttctgg gcggagcgga gacgacgtcc     960
actacgttgg aatgggcgat gagcgcgatg cttgaaaacc ctgaggtggc caagaaagtg   1020
caagaagaga tcgaatccgt tgtgggaaga aagagggtgg tgaaagaaat gatctgggaa   1080
agtatggaat acctgcaatg tgtggtgaaa agacgatga gattatatcc ggcggtgcct    1140
ttgcttatcc cgcacgaatc gacccaagat tgcactgtca atggatactt cattcctgaa   1200
agaaccagaa ttctcgttaa cgcgtgggcg ataggaaaag atccaaacgt gtgggatgat   1260
gcgctggcat tcaaaccaaa aagatttttg ggcanaaatg tggacttgca aaaggaaaa    1320 gagtttttcg atatggttcc ctttggtgcg ggaaggaaag gatgcccagg ggcaagcatg   1380
gccgttgtga cgatggaaca tgcgttggca caactcatgc actgcttcca gtggcgcatt   1440
gaaggagagt tggatatgag tgaacgcttg gcagcctccg tgcaaaaaaa agtcgatctt   1500
tgtgttcttc cccaatggag gctaactagt agcccctga                          1539

<210> SEQ ID NO 54
<211> LENGTH: 1530
<212> TYPE: DNA
<213> ORGANISM: Taxus cuspidata

<400> SEQUENCE: 54
atggatgtct ttatccgtt aaaaagtaca gtagcaaaat ttaacgaatg tttccctgct      60
attcttttca ttgtcctcag tgctgttgct ggcattgttc tgccctgct gctgttccta    120
```

```
cgttctaaac gccgttcctc tgttggacta cccccaggga aattaggtta ccctttcatt      180
ggcgagtcgt tactgttcct gaaggctctt cgatcaaaca cagttgaaca attttttggac    240 gagagagtga agaatttcgg gaatgtcttc aagacgtcat taattgggca tccgacagta    300
gttctctgcg ggcctgcagg aaaccggcta atcctggcga acgaggagaa gctggtgcag    360
atgtcgtggc ccaaatcctc tatgaaactc atggggagaa gtctattac tgccaaaagg     420 ggcgaaggcc atatgatcat ccgctccgca ctgcaaggct ttttcagccc tggtgctctg    480
cagaaataca taggccaaat gagtaaaaca atagaaaatc atattaatga aaatggaag    540 ggaaacgacc aagtgagtgt agttgctttg gtaggagatc tcgtcttcga tatttcggcc    600
tgtttgttct tcaatataaa tgagaagcat gaacgggaac gactgtttga gcttttggag    660
attatagctg tcggagtttt ggctgttccg gtggatcttc ccgggtttgc ttaccatcgg    720
gcacttcaag cacggtcgaa gcttaatgca attctctccg gtttgataga aagagaaaa    780 atggatctga gctcaggatt agcgactagc aatcaggatc ttctttctgt gtttctcacc    840
ttcaaagatg acagaggaaa tccatgcagc gatgaggaaa tcctcgacaa cttttccggg    900
ctgcttcatg gatcctatga caccactgtt tcagcaatgg cctgcgtttt taagcttttg    960
tcttccaatc ccgaatgcta tgaaaaagta gttcaagagc aattggggat actttcgaat    1020
aaattggaag gagacgaaat cacatggaaa gatgtgaaat ccatgaaata tacatggcaa    1080
gtcgttcagg aaacgttacg attgtatccg tcaatttttg gatcatttcg ccaggccatc    1140
actgacattc attataatgg ttacataatt ccaaaagggt ggaagctttt gtggacacca    1200
tacacaacac atcccaagga aatgtatttc agtgagccgg agaaattcct gccttcgagg    1260
ttcgatcagg aagggaaact tgtagctcct tacacatttt tacccttggg tggaggccag    1320
cgttcatgtc caggatggga attttcaaag atggagattt tactgtcggt gcatcatttt    1380
gttaaaacat tcagcacctt cacccagtt gacccagcag aaataattgc aagagattcc    1440
ctctgccctc tcccttccaa tgggttttct gtaaaacttt ttcctagatc ctattcactt    1500
cacacaggca accaggtcaa gaaaatataa                                      1530

<210> SEQ ID NO 55
<211> LENGTH: 1545
<212> TYPE: DNA
<213> ORGANISM: Taxus cuspidata

<400> SEQUENCE: 55
atggcattcg aagcagctac tgttattctt ttcactctgg ctgccctgtt gctagtcgtc      60
atacagcgcc gtagaattag aaggcacaaa ttgcagggga aggtgaaggc accacaacct    120
ccttcatggc ccgttattgg gaatcttcat ctgcttacac agaaagtgcc tattcaccga    180
attctatctt cgctttcgga gagctatgga ccaatcatgc atcttcaact cggtctccga    240
ccagctttgg ttattgcctc ttcagatctg gcgaaagaat gcttcacaac aaatgacaaa    300
gccttcgctt ctcgcccacg tctgtctgca ggaaagcatg taggatatga ctacaaaatc    360
ttcagtatgg ctccttacgg ttcctactgg cgaaaccttc ggaaaatgtg cacgatccag    420
atcctctctg caaccagaat tgactccttc agacacatcc gcgtagagga agtttctgct    480
ctcattcgtt cgttgtttga cagttgccag cgagaggaca ctccagtcaa catgaaagcg    540
aggctctctg atctcacgtt tagtatcatc ctccgtatgg ttgccaacaa gaaattatca    600
ggacctgttt attccgagga atacgaagaa gcggatcatt ttaaccagat gataaaacag    660
```

```
tctgtgttct tacttggagc atttgaggtt ggagatttcc tgccgtttct caagtggctt      720
gatcttcagg gtttcatagc tgctatgaaa aaactgcagc agaaaagaga tgtctttatg      780
cagaaattgg tgattgatca ccgtgagaag agagggagag tcgatgcaaa tgcacaagac      840
ttaattgatg ttctcatctc tgcaacagac aaccatgaaa ttcagtccga tagtaacgac      900
gatgttgtga agccaccgcc cttacaatg ctgaacgcag gtacagatac atcctcggtg       960
accatcgaat gggcattggc ggctctgatg cagcaccctc atattttgag caaagcccag     1020
caggagctcg acacgcatat cggacgcagc cgattactag aggaagcaga tctgcacgag     1080
ctgaaatatt tgcaggcaat tgtgaaagaa acgttgaggc tatatccagc cgcacctctc     1140
ttagttcctc acgaagccat tgaggattgc actgttggag gtaccatgt ctccgcagga      1200 acgcgactga ttgtgaatgc ttgggcaatt cacagagacc cggcagtgtg gaacggccg      1260 accgtgttcg atcctgaacg ttttgaag agcggaaaag aggttgacgt aaaagggcgg       1320
gagtttgaat tgattccgtt tggttcaggg agaagaatgt gtccgggcat gagtctggca     1380
ttgagtgttg ttacgtatac gctggggagg ctgctgcaga gcttcgagtg gtctgttcca     1440
gaaggtatga taattgacat gacggaaggt ttgggactca caatgcccaa agcagttccg     1500
ttggagacca ttatcaaacc tcgccttccc ttccatctct actga                    1545

<210> SEQ ID NO 56
<211> LENGTH: 484
<212> TYPE: PRT
<213> ORGANISM: Taxus cuspidata

<400> SEQUENCE: 56

Met Asp Thr Phe Ile Gln His Glu Ser Ser Pro Leu Leu Ser Leu
  1               5                  10                  15

Thr Leu Ala Val Ile Leu Gly Thr Ile Leu Leu Ile Leu Ser Gly
                 20                  25                  30

Lys Gln Tyr Arg Ser Ser Arg Lys Leu Pro Pro Gly Asn Met Gly Phe
         35                  40                  45

Pro Leu Ile Gly Glu Thr Ile Ala Leu Ile Ser Asp Thr Pro Arg Lys
     50                  55                  60

Phe Ile Asp Asp Arg Val Lys Lys Phe Gly Leu Val Phe Lys Thr Ser
 65                  70                  75                  80

Leu Ile Gly His Pro Ala Val Val Ile Cys Gly Ser Ser Ala Asn Arg
                 85                  90                  95

Phe Leu Leu Ser Asn Glu Glu Lys Leu Val Arg Met Ser Leu Pro Asn
                100                 105                 110

Ala Val Leu Lys Leu Leu Gly Gln Asp Cys Val Met Gly Lys Thr Gly
            115                 120                 125

Val Glu His Gly Ile Val Arg Thr Ala Leu Ala Arg Ala Leu Gly Pro
        130                 135                 140

Gln Ala Leu Gln Asn Tyr Val Ala Lys Met Ser Ser Glu Ile Glu His
145                 150                 155                 160

His Ile Asn Gln Lys Trp Lys Gly Lys Asp Glu Val Lys Val Leu Pro
                165                 170                 175

Leu Ile Arg Ser Leu Val Phe Ser Ile Ser Thr Ser Leu Phe Phe Gly
            180                 185                 190

Ile Asn Asp Glu His Gln Gln Lys Arg Leu His His Leu Leu Glu Thr
        195                 200                 205

Val Ala Met Gly Leu Val Ser Ile Pro Leu Asp Phe Pro Gly Thr Arg
    210                 215                 220
```

```
Phe Arg Lys Ala Leu Tyr Ala Arg Ser Lys Leu Asp Glu Ile Met Ser
225                 230                 235                 240

Ser Val Ile Glu Arg Arg Ser Asp Leu Arg Ser Gly Ala Ala Ser
            245                 250                 255

Ser Asp Gln Asp Leu Leu Ser Val Leu Val Thr Phe Lys Asp Glu Arg
        260                 265                 270

Gly Asn Ser Phe Ala Asp Lys Glu Ile Leu Asp Asn Phe Ser Phe Leu
            275                 280                 285

Leu His Ala Leu Tyr Asp Thr Thr Ile Ser Pro Leu Thr Leu Ile Phe
        290                 295                 300

Lys Leu Leu Ser Ser Ser Pro Glu Cys Tyr Glu Asn Ile Ala Gln Glu
305                 310                 315                 320

Gln Leu Glu Ile Leu Gly Asn Lys Lys Asp Arg Glu Glu Ile Ser Trp
                325                 330                 335

Lys Asp Leu Lys Asp Met Lys Tyr Thr Trp Gln Ala Val Gln Glu Thr
                340                 345                 350

Leu Arg Met Phe Pro Pro Val Tyr Gly Tyr Ile Arg Glu Ala Leu Thr
            355                 360                 365

Asp Ile Asp Tyr Asp Gly Tyr Thr Ile Pro Lys Gly Trp Arg Ile Leu
        370                 375                 380

Cys Ser Pro His Thr Thr His Ser Lys Glu Glu Tyr Phe Asp Glu Pro
385                 390                 395                 400

Glu Glu Phe Arg Pro Ser Arg Phe Glu Asp Gln Gly Arg His Val Ala
                405                 410                 415

Pro Tyr Thr Phe Ile Pro Phe Gly Gly Gly Leu Arg Ile Cys Ala Gly
            420                 425                 430

Trp Glu Phe Ala Lys Met Glu Ile Leu Leu Phe Met His His Phe Val
        435                 440                 445

Lys Thr Phe Ser His Phe Ile Pro Val Asp Pro Asn Glu Lys Ile Ser
        450                 455                 460

Arg Asp Pro Leu Pro Pro Ile Pro Val Lys Gly Phe Ser Ile Lys Pro
465                 470                 475                 480

Phe Pro Arg Ser

<210> SEQ ID NO 57
<211> LENGTH: 484
<212> TYPE: PRT
<213> ORGANISM: Taxus cuspidata

<400> SEQUENCE: 57

Met Leu Ile Glu Met Asp Thr Phe Val Gln Leu Glu Ser Ser Pro Val
1               5                   10                  15

Leu Leu Ser Leu Thr Leu Thr Leu Ile Leu Leu Phe Ile Phe Cys Ser
            20                  25                  30

Lys Gln Tyr Arg Ser Ser Leu Lys Leu Pro Pro Gly Asn Met Gly Phe
        35                  40                  45

Pro Leu Ile Gly Glu Thr Ile Ala Leu Ala Ser Gln Thr Pro Asp Lys
    50                  55                  60

Phe Phe Gly Asp Arg Met Lys Lys Phe Gly Lys Val Phe Lys Thr Ser
65                  70                  75                  80

Leu Ile Gly His Pro Thr Ile Val Leu Cys Gly Ser Ser Gly Asn Arg
                85                  90                  95

Phe Leu Leu Ser Asn Glu Glu Lys Leu Val Arg Met Phe Pro Pro Asn
            100                 105                 110
```

```
Ser Ser Ser Lys Leu Leu Gly Gln Asp Ser Val Leu Gly Lys Ile Gly
            115                 120                 125

Glu Glu His Arg Ile Val Arg Thr Ala Leu Ala Arg Cys Leu Gly Pro
        130                 135                 140

Gln Ala Leu Gln Asn Tyr Val Ser Lys Met Ser Ser Glu Ile Gln Arg
145                 150                 155                 160

His Ile Asn Gln Lys Trp Lys Gly Lys Gly Glu Val Lys Met Leu Pro
                165                 170                 175

Leu Ile Arg Ser Leu Val Phe Ser Ile Ala Thr Ser Leu Phe Phe Gly
            180                 185                 190

Ile Thr Asp Glu Gln Gln Gln Glu Arg Leu His His Leu Leu Glu Thr
        195                 200                 205

Val Val Thr Gly Leu Leu Cys Ile Pro Leu Asp Phe Pro Gly Thr Thr
    210                 215                 220

Phe Arg Lys Ala Leu His Ala Arg Ser Lys Leu Asp Glu Ile Met Ser
225                 230                 235                 240

Ser Val Ile Glu Arg Arg Asn Asp Leu Arg Leu Gly Ala Ala Ser
                245                 250                 255

Ser Asp Gln Asp Leu Leu Ser Val Leu Leu Thr Phe Lys Asp Glu Arg
            260                 265                 270

Gly Asn Pro Phe Ala Asp Lys Glu Ile Leu Asp Asn Phe Ser Phe Leu
        275                 280                 285

Leu His Ala Leu Tyr Asp Thr Thr Ile Ser Pro Leu Thr Leu Val Phe
    290                 295                 300

Lys Leu Val Ser Ser Asn Pro Glu Cys Tyr Glu Asn Ile Ala Gln Glu
305                 310                 315                 320

Gln Leu Glu Ile Leu Arg Asn Lys Lys Asp Gly Glu Asp Ile Ser Trp
                325                 330                 335

Ala Asp Leu Lys Asp Met Lys Tyr Thr Trp Gln Ala Val Gln Glu Thr
            340                 345                 350

Leu Arg Met Cys Pro Pro Val Tyr Gly Asn Phe Arg Lys Ala Leu Thr
        355                 360                 365

Asp Ile His Tyr Asp Gly Tyr Thr Ile Pro Lys Gly Trp Arg Ile Leu
    370                 375                 380

Cys Ser Pro Tyr Thr Thr His Ser Lys Glu Glu Tyr Phe Asp Asp Pro
385                 390                 395                 400

Glu Lys Phe Arg Pro Ser Arg Phe Glu Glu Gln Gly Arg Asp Val Ala
                405                 410                 415

Pro Tyr Thr Phe Ile Pro Phe Gly Gly Gly Leu Arg Ile Cys Pro Gly
            420                 425                 430

Arg Glu Phe Ala Lys Met Glu Ile Leu Val Phe Met His His Phe Val
        435                 440                 445

Lys Ala Phe Ser Ser Phe Ile Pro Val Asp Pro Asn Glu Lys Ile Ser
    450                 455                 460

Thr Asp Pro Leu Pro Ser Ile Pro Val Asn Gly Phe Ser Ile Asn Leu
465                 470                 475                 480

Val Pro Arg Ser

<210> SEQ ID NO 58
<211> LENGTH: 501
<212> TYPE: PRT
<213> ORGANISM: Taxus cuspidata

<400> SEQUENCE: 58
```

-continued

```
Met Asp Ser Phe Ser Phe Leu Lys Ser Met Glu Ala Lys Phe Gly Gln
 1               5                  10                  15

Val Ile His Arg Asp Gln Ser Ser Thr Ala Leu Leu Ser Leu Ala
             20                  25                  30

Phe Thr Ala Ala Val Ala Ile Phe Leu Val Leu Leu Phe Arg Phe Lys
             35                  40                  45

Ser Arg Pro Ser Thr Asn Phe Pro Pro Gly Asn Phe Gly Phe Pro Phe
         50                  55                  60

Ile Gly Glu Thr Ile Gln Phe Leu Arg Ala Leu Arg Ser Glu Ser Pro
 65                  70                  75                  80

His Met Phe Phe Asp Glu Arg Leu Lys Lys Phe Gly Arg Val Phe Lys
                 85                  90                  95

Thr Ser Leu Thr Gly His Pro Thr Ala Val Phe Cys Gly Pro Ala Gly
                100                 105                 110

Asn Arg Phe Ile Tyr Ser Asn Glu His Lys Leu Val Gln Ser Ser Gly
                115                 120                 125

Pro Asn Ser Phe Val Lys Leu Val Gly Gln Gln Ser Ile Val Thr Lys
    130                 135                 140

Thr Gly Glu Glu His Arg Ile Phe Leu Gly Val Leu Asn Glu Phe Leu
145                 150                 155                 160

Gly Pro His Ala Leu Gln Ser Tyr Thr Pro Lys Met Ser Ser Lys Ile
                165                 170                 175

Gln Glu Asn Ile Asn Lys His Trp Lys Gly Lys Asp Glu Val Asn Met
                180                 185                 190

Leu Pro Ser Ile Arg Gln Leu Val Phe Ser Ile Ser Ser Ser Leu Phe
    195                 200                 205

Phe Asp Ile Asn Asp Glu Asp Gln Gln Glu Gln Leu Lys Thr Leu Leu
    210                 215                 220

Glu Thr Ile Leu Val Gly Thr Leu Ser Val Pro Leu Asp Ile Pro Gly
225                 230                 235                 240

Ser Asn Phe Arg Lys Ala Leu Arg Ala Arg Ser Lys Leu Asp Glu Ile
                245                 250                 255

Leu Ser Arg Leu Ile Glu Ser Arg Arg Lys Asp Met Arg Ser Gly Ile
                260                 265                 270

Ala Ser Thr Ser Lys Asn Leu Leu Ser Val Leu Leu Ala Phe Lys Asp
                275                 280                 285

Glu Arg Gly Asn Pro Leu Thr Asp Thr Glu Ile Leu Asp Asn Phe Ser
    290                 295                 300

Phe Met Leu His Ala Ser Tyr Asp Thr Thr Val Ser Pro Thr Val Cys
305                 310                 315                 320

Ile Phe Lys Leu Leu Ser Ala Asn Pro Glu Cys Tyr Glu Lys Val Val
                325                 330                 335

Gln Glu Gln Leu Gly Ile Leu Gly Asn Lys Lys Asp Gly Glu Glu Met
                340                 345                 350

Cys Trp Asn Asp Leu Lys Ala Met Lys Tyr Thr Trp Gln Ala Ala Gln
                355                 360                 365

Glu Thr Met Arg Leu Phe Pro Pro Ala Phe Gly Ser Phe Arg Lys Val
                370                 375                 380

Ile Ala Asp Ile His His Asp Gly Tyr Ile Ile Pro Lys Gly Trp Lys
385                 390                 395                 400

Ala Met Val Thr Asn Tyr Ser Thr Ser Arg Lys Glu Glu Tyr Phe Asp
                405                 410                 415
```

```
Glu Pro Asp Asn Phe Lys Pro Ser Arg Phe Gly Asp Gly Lys Tyr Val
            420                 425                 430

Ala Pro Tyr Thr Phe Leu Pro Phe Gly Ala Gly Ile Arg Ile Cys Pro
            435                 440                 445

Gly Trp Glu Phe Ala Lys Leu Glu Met Leu Leu Phe Ile His His Phe
    450                 455                 460

Val Lys Asn Phe Ser Gly Tyr Leu Pro Leu Asp Thr Lys Glu Lys Ile
465                 470                 475                 480

Ser Gly Asp Pro Phe Pro Leu Pro Lys Asn Gly Phe Pro Ile Lys
            485                 490                 495

Leu Phe Pro Arg Thr
            500

<210> SEQ ID NO 59
<211> LENGTH: 500
<212> TYPE: PRT
<213> ORGANISM: Taxus cuspidata

<400> SEQUENCE: 59

Met Asp Ala Leu Ser Leu Val Asn Ser Thr Val Ala Lys Phe Asn Glu
  1               5                  10                  15

Val Thr Gln Leu Gln Ala Ser Pro Ala Ile Leu Ser Thr Ala Leu Thr
                 20                  25                  30

Ala Ile Ala Gly Ile Ile Val Leu Leu Val Ile Thr Ser Lys Arg Arg
             35                  40                  45

Ser Ser Leu Lys Leu Pro Pro Gly Lys Leu Gly Leu Pro Phe Ile Gly
     50                  55                  60

Glu Thr Leu Glu Phe Val Lys Ala Leu Arg Ser Asp Thr Leu Arg Gln
 65                  70                  75                  80

Phe Val Glu Glu Arg Glu Gly Lys Phe Gly Arg Val Phe Lys Thr Ser
                 85                  90                  95

Leu Leu Gly Lys Pro Thr Val Ile Leu Cys Gly Pro Ala Gly Asn Arg
                100                 105                 110

Leu Val Leu Ser Asn Glu Glu Lys Leu Leu His Val Ser Trp Ser Ala
            115                 120                 125

Gln Ile Ala Arg Ile Leu Gly Leu Asn Ser Val Ala Val Lys Arg Gly
        130                 135                 140

Asp Asp His Arg Val Leu Arg Val Ala Leu Ala Gly Phe Leu Gly Ser
145                 150                 155                 160

Ala Gly Leu Gln Leu Tyr Ile Gly Lys Met Ser Ala Leu Ile Arg Asn
                165                 170                 175

His Ile Asn Glu Lys Trp Lys Gly Lys Asp Glu Val Asn Val Leu Ser
            180                 185                 190

Leu Val Arg Asp Leu Val Met Asp Asn Ser Ala Ile Leu Phe Phe Asn
        195                 200                 205

Ile Tyr Asp Lys Glu Arg Lys Gln Gln Leu His Glu Ile Leu Lys Ile
    210                 215                 220

Ile Leu Ala Ser His Phe Gly Ile Pro Leu Asn Ile Pro Gly Phe Leu
225                 230                 235                 240

Tyr Arg Lys Ala Leu Lys Gly Ser Leu Lys Arg Lys Ile Leu Ser
                245                 250                 255

Ala Leu Leu Glu Lys Arg Lys Asp Glu Leu Arg Ser Arg Leu Ala Ser
            260                 265                 270

Ser Asn Gln Asp Leu Leu Ser Val Leu Leu Ser Phe Arg Asp Glu Arg
        275                 280                 285
```

```
Gly Lys Pro Leu Ser Asp Glu Ala Val Leu Asp Asn Cys Phe Ala Met
        290                 295                 300

Leu Asp Ala Ser Tyr Asp Thr Thr Thr Ser Gln Met Thr Leu Ile Leu
305                 310                 315                 320

Lys Met Leu Ser Ser Asn Pro Glu Cys Phe Glu Lys Val Val Gln Glu
                325                 330                 335

Gln Leu Glu Ile Ala Ser Asn Lys Lys Glu Gly Glu Glu Ile Thr Met
            340                 345                 350

Lys Asp Ile Lys Ala Met Lys Tyr Thr Trp Gln Val Leu Gln Glu Ser
            355                 360                 365

Leu Arg Met Leu Ser Pro Val Phe Gly Thr Leu Arg Lys Thr Met Asn
370                 375                 380

Asp Ile Asn His Asp Gly Tyr Thr Ile Pro Lys Gly Trp Gln Val Val
385                 390                 395                 400

Trp Thr Thr Tyr Ser Thr His Gln Lys Asp Ile Tyr Phe Lys Gln Pro
                405                 410                 415

Asp Lys Phe Met Pro Ser Arg Phe Glu Glu Asp Gly His Leu Asp
                420                 425                 430

Ala Tyr Thr Phe Val Pro Phe Gly Gly Gly Arg Arg Thr Cys Pro Gly
            435                 440                 445

Trp Glu Tyr Ala Lys Val Glu Ile Leu Leu Phe Leu His His Phe Val
        450                 455                 460

Lys Ala Phe Ser Gly Tyr Thr Pro Thr Asp Pro His Glu Arg Ile Cys
465                 470                 475                 480

Gly Tyr Pro Val Pro Leu Val Pro Val Lys Gly Phe Pro Ile Lys Leu
                485                 490                 495

Ile Ala Arg Ser
            500

<210> SEQ ID NO 60
<211> LENGTH: 492
<212> TYPE: PRT
<213> ORGANISM: Taxus cuspidata
<220> FEATURE:
<221> NAME/KEY: misc_feature
<222> LOCATION: (1)..(492)
<223> OTHER INFORMATION: "Xaa" equals any peptide

<400> SEQUENCE: 60

Met Asp Thr Ile Arg Ala Ser Phe Gly Glu Val Ile Gln Pro Glu Tyr
1               5                   10                  15

Ser Pro Leu Ile Ile Ser Xaa Ala Leu Ala Ala Phe Leu Gly Ile Val
                20                  25                  30

Ile Phe Ser Ile Phe Ser Ser Thr Arg Arg Ser Tyr Val Asn Leu Pro
            35                  40                  45

Pro Gly Asn Leu Gly Leu Pro Phe Ile Gly Glu Thr Ile Gln Phe Leu
        50                  55                  60

Gly Ala Leu Gln Ser Glu Lys Pro His Thr Phe Phe Asp Glu Arg Val
65                  70                  75                  80

Lys Lys Phe Gly Lys Val Phe Lys Thr Ser Leu Ile Gly Asp Pro Thr
                85                  90                  95

Val Val Leu Cys Gly Pro Ala Gly Asn Arg Leu Val Leu Ser Asn Glu
            100                 105                 110

Asp Lys Leu Val Gln Ser Ala Gly Pro Lys Ser Phe Leu Lys Leu Phe
        115                 120                 125
```

```
Gly Glu Asp Ser Val Ala Ala Lys Arg Glu Glu Ser His Arg Ile Leu
            130                 135                 140

Arg Ser Ala Leu Gly Arg Phe Leu Gly Pro His Ala Leu Gln Asn Tyr
145                 150                 155                 160

Ile Gly Lys Met Asn Ser Glu Met Gln Arg His Phe Asp Asp Lys Trp
                165                 170                 175

Lys Gly Lys Asp Glu Val Lys Val Leu Pro Leu Val Arg Gly Leu Ile
            180                 185                 190

Phe Ser Ile Ala Thr Ser Leu Phe Phe Asn Ile Asn Asp Asp Arg Gln
                195                 200                 205

Arg Glu Gln Leu His Gly Leu Leu Asp Thr Ile Leu Val Gly Ser Met
210                 215                 220

Thr Ile Pro Leu Asn Ile Pro Gly Thr Leu Phe Arg Lys Ala Val Lys
225                 230                 235                 240

Ala Arg Ala Lys Leu Asp Glu Ile Leu Phe Ala Leu Ile Glu Asn Arg
                245                 250                 255

Arg Arg Glu Leu Arg Ser Gly Leu Asn Ser Gly Asn Gln Asp Leu Leu
            260                 265                 270

Ser Ser Leu Leu Thr Phe Lys Asp Glu Lys Gly Asn Pro Leu Thr Asp
                275                 280                 285

Lys Glu Ile Leu Asp Asn Phe Ser Val Met Leu His Ala Ser Tyr Asp
290                 295                 300

Thr Thr Val Ser Pro Thr Val Leu Ile Leu Lys Leu Leu Ala Ser Asn
305                 310                 315                 320

Pro Glu Cys Tyr Glu Lys Val Val Gln Glu Gln Leu Gly Ile Leu Ala
                325                 330                 335

Ser Lys Lys Glu Gly Glu Glu Val Asn Trp Lys Asp Leu Lys Ala Met
            340                 345                 350

Pro Tyr Thr Trp Gln Ala Ile Gln Glu Pro Leu Xaa Met Pro Xaa Gln
                355                 360                 365

Leu Leu Glu Cys Phe Glu Glu Leu Ser Leu Ile Phe Ser Trp Lys Ala
370                 375                 380

Ile Gln Phe Gln Lys Asp Gly Gln Leu Cys Gly Xaa Leu Ile Val Asn
385                 390                 395                 400

Gly Arg Glu Glu Phe Phe Asn Glu Pro Asp Lys Phe Lys Pro Ser Arg
                405                 410                 415

Phe Glu Glu Gly Lys Pro Leu Asp Pro Tyr Thr Phe Ile Pro Phe Gly
            420                 425                 430

Ala Gly Val Arg Ile Cys Ala Gly Trp Glu Phe Ala Lys Ala Glu Leu
                435                 440                 445

Leu Leu Phe Val His Pro Phe Val Lys Asn Phe Ser Gly Cys Ile Ile
450                 455                 460

Ile Asp Pro Asn Glu Lys Ile Ser Gly Asp Pro Phe Pro Leu Pro
465                 470                 475                 480

Thr Ser Gly Gln Leu Met Lys Leu Ile Pro Arg Ser
                485                 490

<210> SEQ ID NO 61
<211> LENGTH: 500
<212> TYPE: PRT
<213> ORGANISM: Taxus cuspidata
<220> FEATURE:
<221> NAME/KEY: misc_feature
<222> LOCATION: (1)..(500)
<223> OTHER INFORMATION: "Xaa" equals any peptide
```

<400> SEQUENCE: 61

```
Met Asp Ser Phe Asn Phe Leu Arg Gly Ile Gly Ala Asp Phe Gly Gly
  1               5                  10                  15

Phe Ile Gln Phe Gln Ser Ser Pro Ala Val Leu Ser Leu Ser Leu Ile
             20                  25                  30

Thr Thr Ile Leu Gly Val Leu Leu Trp Phe Phe Leu His Lys Asn
         35                  40                  45

Gly Ser Ser Val Thr Leu Pro Pro Gly Asn Leu Gly Phe Pro Phe Ile
     50                  55                  60

Gly Glu Thr Ile Pro Phe Leu Arg Ala Leu Arg Ser Glu Thr Pro Gln
 65                  70                  75                  80

Thr Phe Phe Asp Glu Arg Val Lys Lys Phe Gly Val Val Phe Lys Thr
                 85                  90                  95

Arg Ile Val Gly His Pro Thr Val Val Leu Cys Gly Pro Glu Gly Asn
                100                 105                 110

Arg Phe Leu Leu Ser Asn Glu Asp Lys Leu Val Gln Ala Ser Leu Pro
            115                 120                 125

Asn Ser Ser Glu Lys Leu Ile Gly Lys Tyr Ser Ile Leu Ser Lys Arg
        130                 135                 140

Gly Glu Glu His Arg Ile Leu Arg Ala Ala Leu Ala Arg Phe Leu Arg
145                 150                 155                 160

Pro Gln Ala Leu Gln Gly Tyr Val Ala Lys Met Ser Ser Glu Ile Gln
                165                 170                 175

His His Ile Lys Gln Lys Trp Lys Gly Asn Asp Glu Val Lys Val Leu
            180                 185                 190

Pro Leu Ile Arg Thr Leu Ile Phe Asn Ile Ala Ser Ser Leu Phe Phe
        195                 200                 205

Gly Ile Asn Asp Glu His Gln Gln Glu Gln Leu His His Leu Leu Glu
    210                 215                 220

Ala Ile Val Leu Gly Ser Leu Ser Val Pro Leu Asp Phe Pro Gly Thr
225                 230                 235                 240

Arg Phe Arg Lys Ala Leu Asp Ala Arg Ser Lys Leu Asp Glu Ile Leu
                245                 250                 255

Ser Ser Leu Met Glu Ser Arg Arg Arg Asp Leu Arg Leu Gly Thr Ala
            260                 265                 270

Ser Glu Asn Gln Asp Leu Leu Ser Val Leu Leu Thr Phe Lys Asp Glu
        275                 280                 285

Arg Gly Asn Pro Leu Thr Asp Lys Glu Ile Phe Asp Asn Phe Ser Phe
    290                 295                 300

Met Leu His Ala Ser Tyr Asp Thr Thr Val Ser Pro Thr Gly Leu Met
305                 310                 315                 320

Leu Lys Leu Leu Phe Ser Ser Pro Asp Cys Tyr Glu Lys Leu Val Gln
                325                 330                 335

Glu Gln Leu Gly Ile Val Gly Asn Lys Lys Gly Glu Glu Ile Ser
            340                 345                 350

Trp Asn Asp Leu Lys Ala Met Lys Tyr Thr Cys Lys Val Val Gln Glu
        355                 360                 365

Ser Met Arg Met Leu Pro Pro Val Phe Gly Ser Tyr Arg Lys Ala Xaa
    370                 375                 380

Thr Tyr Ile His Tyr Asp Gly Tyr Thr Ile Pro Lys Gly Trp Asn Ile
385                 390                 395                 400

Phe Trp Ser Pro Tyr Thr Thr His Gly Lys Glu Glu Tyr Phe Asn Glu
                405                 410                 415
```

-continued

```
Ala Asp Lys Phe Met Pro Ser Arg Phe Glu Glu Gly Lys Tyr Val Ala
            420                 425                 430

Pro Tyr Thr Phe Leu Pro Phe Gly Ala Gly Leu Arg Val Cys Pro Gly
            435                 440                 445

Trp Glu Phe Ala Lys Thr Glu Ile Leu Leu Phe Val His His Phe Ile
            450                 455                 460

Thr Thr Phe Ser Ser Tyr Ile Pro Ile Asp Pro Lys Asp Lys Ile Ser
465                 470                 475                 480

Gly Asp Pro Phe Pro Pro Leu Pro Thr Asn Gly Phe Ser Met Lys Leu
                485                 490                 495

Phe Thr Arg Ser
            500

<210> SEQ ID NO 62
<211> LENGTH: 483
<212> TYPE: PRT
<213> ORGANISM: Taxus cuspidata

<400> SEQUENCE: 62

Met Asp Thr Leu Ile Gln Ile Gln Ser Ser Pro Asp Phe Leu Ser Phe
  1               5                  10                  15

Thr Leu Thr Ala Phe Leu Gly Val Val Val Leu Leu Ile Phe Arg Tyr
             20                  25                  30

Lys His Arg Ser Ala Leu Lys Leu Pro Pro Gly Asn Leu Gly Leu Pro
         35                  40                  45

Phe Ile Gly Glu Thr Ile Thr Phe Ala Ser Gln Pro Pro Gln Lys Phe
     50                  55                  60

Leu Asn Glu Arg Gly Lys Lys Phe Gly Pro Val Phe Lys Thr Ser Leu
 65                  70                  75                  80

Ile Gly His Pro Thr Val Leu Cys Gly Ser Ser Gly Asn Arg Phe
                 85                  90                  95

Leu Leu Ser Asn Glu Glu Lys Leu Val Arg Met Ser Leu Pro Asn Ser
                100                 105                 110

Tyr Met Lys Leu Leu Gly Gln Asp Ser Leu Leu Gly Lys Thr Gly Gln
            115                 120                 125

Glu His Arg Ile Val Arg Thr Ala Leu Gly Arg Phe Leu Gly Pro Gln
        130                 135                 140

Glu Leu Gln Asn His Val Ala Lys Met Ser Ser Asp Ile Gln His His
145                 150                 155                 160

Ile Asn Gln Lys Trp Lys Gly Asn Asp Glu Val Lys Val Leu Pro Leu
                165                 170                 175

Ile Arg Asn Leu Val Phe Ser Ile Ala Thr Ser Leu Phe Phe Gly Ile
            180                 185                 190

Asn Asp Glu His Gln Gln Glu Arg Leu His Leu Leu Glu Thr Ile
        195                 200                 205

Val Met Gly Ala Val Cys Ile Pro Leu Ala Phe Pro Gly Ser Gly Phe
    210                 215                 220

Arg Lys Ala Leu Gln Ala Arg Ser Glu Leu Asp Gly Ile Leu Ile Ser
225                 230                 235                 240

Leu Met Lys Ile Arg Arg Ser Asp Leu Arg Ser Gly Ala Ala Ser Ser
                245                 250                 255

Asn Gln Asp Leu Leu Ser Val Leu Leu Thr Phe Lys Asp Glu Arg Gly
            260                 265                 270

Asn Pro Leu Thr Asp Lys Glu Ile Leu Asp Asn Phe Ser Val Leu Leu
```

```
                275                 280                 285
His Gly Leu Tyr Asp Thr Thr Ile Ser Pro Leu Thr Leu Ile Phe Lys
    290                 295                 300

Leu Met Ser Ser Asn Thr Glu Cys Tyr Glu Asn Val Val Gln Glu Gln
305                 310                 315                 320

Leu Glu Ile Leu Ser His Arg Glu Lys Gly Glu Ile Gly Trp Lys
                325                 330                 335

Asp Leu Lys Ser Met Lys Tyr Thr Trp Gln Ala Ile Gln Glu Thr Leu
                340                 345                 350

Arg Met Phe Pro Pro Val Tyr Gly Asn Phe Arg Lys Ala Leu Thr Asp
            355                 360                 365

Ile His Tyr Asp Gly Tyr Thr Ile Pro Lys Gly Trp Arg Val Leu Cys
        370                 375                 380

Ser Pro Phe Thr Thr His Ser Asn Glu Glu Tyr Phe Asn Glu Pro Asp
385                 390                 395                 400

Glu Phe Arg Pro Ser Arg Phe Glu Gly Gln Gly Lys Asn Val Pro Ser
                405                 410                 415

Tyr Thr Phe Ile Pro Phe Gly Gly Gly Leu Arg Ile Cys Pro Gly Trp
            420                 425                 430

Glu Phe Ala Lys Thr Glu Met Leu Leu Phe Ile His Tyr Phe Val Lys
        435                 440                 445

Thr Phe Ser Ser Tyr Val Pro Val Asp Pro Asn Glu Lys Ile Ser Ala
    450                 455                 460

Asp Pro Leu Ala Ser Phe Pro Val Asn Gly Phe Ser Val Lys Leu Phe
465                 470                 475                 480

Pro Arg Ser

<210> SEQ ID NO 63
<211> LENGTH: 503
<212> TYPE: PRT
<213> ORGANISM: Taxus cuspidata

<400> SEQUENCE: 63

Met Asp Ala Phe Asn Ile Leu Lys Gly Pro Ala Ala Lys Leu Asn Gly
  1               5                  10                  15

Val Val Gln Leu Gly Ser Tyr Thr Asp Arg Ile Leu Ser Ile Thr Val
                 20                  25                  30

Val Ala Phe Ile Thr Ile Leu Leu Leu Met Leu Arg Trp Lys Ser
             35                  40                  45

Gln Ser Ser Val Lys Leu Pro Pro Gly Asn Phe Gly Phe Pro Leu Ile
     50                  55                  60

Gly Glu Thr Leu Gln Leu Leu Arg Ala Phe Arg Ser Asn Thr Thr Gln
 65                  70                  75                  80

Gln Phe Phe Asp Glu Arg Gln Lys Phe Gly Cys Val Phe Lys Thr
             85                  90                  95

Ser Leu Val Gly Glu Arg Thr Val Val Leu Cys Gly Pro Ser Gly Asn
                100                 105                 110

Arg Leu Val Leu Ala Asn Gln Asn Lys Val Val Glu Ser Ser Trp Pro
            115                 120                 125

Ser Ala Phe Ile Lys Leu Ile Gly Glu Asp Ser Ile Ala Asn Thr Asn
    130                 135                 140

Gly Glu Lys His Arg Ile Leu Arg Ala Ala Leu Leu Arg Tyr Leu Gly
145                 150                 155                 160

Pro Gly Ser Leu Gln Asn Tyr Val Gly Lys Met Arg Ser Glu Ile Glu
```

```
                165                 170                 175
His His Ile Asn Glu Lys Trp Lys Gly Lys Asp Glu Val Lys Val Leu
            180                 185                 190

Asp Leu Val Arg Lys Asn Val Phe Ser Val Ala Thr Ala Leu Phe Phe
            195                 200                 205

Gly Val Asn Asp Glu Glu Arg Lys Arg Ile Arg Pro Pro Ser Ile Leu
            210                 215                 220

Arg Lys Leu His Phe Ala Gly Ser Phe Ser Ile Pro Leu Asp Phe Pro
225                 230                 235                 240

Gly Thr Ser Tyr Arg Arg Ala Leu Glu Ala Arg Leu Lys Leu Asp Lys
                245                 250                 255

Ile Leu Ser Ser Leu Ile Glu Arg Arg Arg Ser Asp Leu Arg Ser Gly
            260                 265                 270

Leu Ala Ser Gly Asn Glu Asp Leu Val Ser Val Leu Leu Thr Phe Lys
            275                 280                 285

Asp Glu Gly Gly Asn Pro Leu Thr Asp Lys Glu Ile Leu Asp Asn Phe
            290                 295                 300

Ser Gly Leu Leu His Ala Ser Tyr Asp Thr Thr Thr Ser Ala Leu Thr
305                 310                 315                 320

Leu Thr Phe Lys Leu Met Ser Ser Ser Ala Glu Cys Tyr Asp Lys Val
                325                 330                 335

Val Gln Glu Gln Leu Arg Ile Val Ser Asn Lys Lys Glu Gly Glu Glu
            340                 345                 350

Ile Ser Leu Lys Asp Leu Lys Asp Met Lys Tyr Thr Trp Gln Val Val
            355                 360                 365

Gln Glu Thr Leu Arg Met Phe Pro Pro Leu Phe Gly Ser Phe Arg Lys
            370                 375                 380

Thr Ile Ala Asp Ile Gln Tyr Asp Gly Tyr Thr Ile Pro Lys Gly Trp
385                 390                 395                 400

Lys Val Leu Trp Ala Thr Tyr Thr Thr His Gly Arg Asp Glu Tyr Phe
                405                 410                 415

Ser Glu Pro Gln Lys Phe Arg Pro Ser Arg Phe Glu Glu Gly Gly Lys
            420                 425                 430

His Val Ala Pro Tyr Thr Phe Leu Pro Phe Glu Gly Gly Glu Arg Thr
            435                 440                 445

Cys Pro Gly Tyr Glu Phe Ser Lys Thr His Ile Leu Leu Phe Ile His
450                 455                 460

Gln Phe Val Lys Thr Phe Thr Gly Tyr Ile Pro Leu Asp Pro Asn Glu
465                 470                 475                 480

Ser Ile Ser Ala Asn Pro Leu Pro Pro Leu Pro Ala Asn Gly Phe Pro
                485                 490                 495

Val Lys Leu Phe Gln Arg Ser
            500

<210> SEQ ID NO 64
<211> LENGTH: 497
<212> TYPE: PRT
<213> ORGANISM: Taxus cuspidata

<400> SEQUENCE: 64

Met Asp Ser Phe Ile Phe Leu Arg Ser Ile Gly Thr Lys Phe Gly Gln
1               5                   10                  15

Leu Glu Ser Ser Pro Ala Ile Leu Ser Leu Thr Leu Ala Pro Ile Leu
            20                  25                  30
```

-continued

```
Ala Ile Ile Leu Leu Leu Phe Arg Tyr Asn His Arg Ser Ser Val
         35                  40                  45

Lys Leu Pro Pro Gly Lys Leu Gly Phe Pro Leu Ile Gly Glu Thr Ile
 50                  55                  60

Gln Leu Leu Arg Thr Leu Arg Ser Glu Thr Pro Gln Lys Phe Phe Asp
 65                  70                  75                  80

Asp Arg Leu Lys Lys Phe Gly Pro Val Tyr Met Thr Ser Leu Ile Gly
                 85                  90                  95

His Pro Thr Val Val Leu Cys Gly Pro Ala Gly Asn Lys Leu Val Leu
                100                 105                 110

Ser Asn Glu Asp Lys Leu Val Glu Met Glu Gly Pro Lys Ser Phe Met
            115                 120                 125

Lys Leu Ile Gly Glu Asp Ser Ile Val Ala Lys Arg Gly Glu Asp His
130                 135                 140

Arg Ile Leu Arg Thr Ala Leu Ala Arg Phe Leu Gly Ala Gln Ala Leu
145                 150                 155                 160

Gln Asn Tyr Leu Gly Arg Met Ser Ser Glu Ile Gly His His Phe Asn
                165                 170                 175

Glu Lys Trp Lys Gly Lys Asp Glu Val Lys Val Leu Pro Leu Val Arg
            180                 185                 190

Gly Leu Ile Phe Ser Ile Ala Ser Thr Leu Phe Phe Asp Val Asn Asp
            195                 200                 205

Gly His Gln Gln Lys Gln Leu His His Leu Leu Glu Thr Ile Leu Val
            210                 215                 220

Gly Ser Leu Ser Val Pro Leu Asp Phe Pro Gly Thr Arg Tyr Arg Lys
225                 230                 235                 240

Gly Leu Gln Ala Arg Leu Lys Leu Asp Glu Ile Leu Ser Ser Leu Ile
                245                 250                 255

Lys Arg Arg Arg Arg Asp Leu Arg Ser Gly Ile Ala Ser Asp Asp Gln
                260                 265                 270

Asp Leu Leu Ser Val Leu Leu Thr Phe Arg Asp Glu Lys Gly Asn Ser
            275                 280                 285

Leu Thr Asp Gln Gly Ile Leu Asp Asn Phe Ser Ala Met Phe His Ala
290                 295                 300

Ser Tyr Asp Thr Thr Val Ala Pro Met Ala Leu Ile Phe Lys Leu Leu
305                 310                 315                 320

Tyr Ser Asn Pro Glu Tyr His Glu Lys Val Phe Gln Glu Gln Leu Glu
                325                 330                 335

Ile Ile Gly Asn Lys Lys Glu Gly Glu Ile Ser Trp Lys Asp Leu
            340                 345                 350

Lys Ser Met Lys Tyr Thr Trp Gln Ala Val Gln Glu Ser Leu Arg Met
            355                 360                 365

Tyr Pro Pro Val Phe Gly Ile Phe Arg Lys Ala Ile Thr Asp Ile His
370                 375                 380

Tyr Asp Gly Tyr Thr Ile Pro Lys Gly Trp Arg Val Leu Cys Ser Pro
385                 390                 395                 400

Tyr Thr Thr His Leu Arg Glu Glu Tyr Phe Pro Glu Pro Glu Glu Phe
                405                 410                 415

Arg Pro Ser Arg Phe Glu Asp Glu Gly Arg His Val Thr Pro Tyr Thr
            420                 425                 430

Tyr Val Pro Phe Gly Gly Gly Leu Arg Thr Cys Pro Gly Trp Glu Phe
            435                 440                 445

Ser Lys Ile Glu Ile Leu Leu Phe Val His His Phe Val Lys Asn Phe
```

-continued

```
                450                 455                 460
Ser Ser Tyr Ile Pro Val Asp Pro Asn Glu Lys Val Leu Ser Asp Pro
465                 470                 475                 480

Leu Pro Pro Leu Pro Ala Asn Gly Phe Ser Ile Lys Leu Phe Pro Arg
                485                 490                 495

Ser

<210> SEQ ID NO 65
<211> LENGTH: 507
<212> TYPE: PRT
<213> ORGANISM: Taxus cuspidata
<220> FEATURE:
<221> NAME/KEY: misc_feature
<222> LOCATION: (1)..(507)
<223> OTHER INFORMATION: "Xaa" equals any peptide

<400> SEQUENCE: 65

Met Glu Thr Lys Phe Gly Gln Leu Met Gln Leu Glu Phe Leu Pro Phe
  1                 5                  10                  15

Ile Leu Thr Pro Ile Leu Gly Ala Leu Val Leu Leu His Leu Phe Arg
                 20                  25                  30

His Arg Asn Arg Ser Ser Val Lys Leu Pro Pro Gly Lys Leu Gly Phe
                 35                  40                  45

Pro Val Ile Gly Glu Thr Ile Gln Phe Leu Arg Ala Leu Arg Ser Gln
 50                  55                  60

Thr Pro Gln Lys Phe Phe Asp Asp Arg Val Gln Lys Phe Gly Gly Val
 65                  70                  75                  80

Phe Lys Thr Ser Leu Ile Gly Asn Pro Leu Val Val Met Cys Gly Pro
                 85                  90                  95

Ala Gly Asn Arg Leu Val Leu Ser Asn Glu Asp Lys Leu Val Gln Leu
                100                 105                 110

Glu Ala Pro Asn Ser Leu Met Lys Leu Met Gly Gln Asp Ser Leu Leu
                115                 120                 125

Ala Lys Arg Gln Glu Asp His Arg Thr Leu Arg Ala Ala Leu Ala Arg
130                 135                 140

Phe Leu Gly Pro Gln Ala Leu Xaa Asn Tyr Met Thr Lys Ile Ser Ser
145                 150                 155                 160

Arg Thr Glu His His Met Asn Glu Lys Trp Lys Gly Lys Asp Glu Val
                165                 170                 175

Arg Thr Leu Pro Leu Ile Arg Glu Leu Ile Phe Ser Asn Ala Ser Ser
                180                 185                 190

Leu Phe Phe Asp Ile Asn Asp Glu His Gln Gln Glu Arg Leu His His
                195                 200                 205

Leu Leu Glu Ala Val Val Val Gly Ser Met Ser Ile Pro Leu Asp Phe
                210                 215                 220

Pro Gly Thr Arg Leu Arg Lys Ala Leu Gln Ala Arg Ser Lys Leu Asp
225                 230                 235                 240

Glu Ile Leu Ser Ser Leu Ile Lys Ser Arg Arg Lys Asp Leu Val Ser
                245                 250                 255

Gly Ile Ala Ser Asp Asp Gln Asp Leu Leu Ser Val Leu Leu Thr Phe
                260                 265                 270

Lys Asp Glu Arg Gly Asn Pro Leu Thr Asp Lys Glu Ile Leu Asp Asn
                275                 280                 285

Phe Ser Leu Leu Leu His Ala Ser Tyr Asp Thr Thr Val Ser Pro Met
                290                 295                 300
```

```
Val Leu Thr Leu Lys Leu Leu Ser Ser Asn Pro Glu Cys Tyr Glu Lys
305                 310                 315                 320

Val Val Gln Glu Gln Leu Gly Ile Val Ala Asn Lys Arg Ile Gly Glu
            325                 330                 335

Glu Ile Ser Trp Lys Asp Leu Lys Ala Met Lys Tyr Thr Trp Gln Val
            340                 345                 350

Val Gln Glu Thr Leu Arg Met Phe Pro Pro Leu Phe Gly Ser Phe Arg
        355                 360                 365

Lys Ala Met Val Asp Ile Asp Tyr Asp Gly Tyr Thr Ile Pro Lys Gly
    370                 375                 380

Trp Met Ile Leu Trp Thr Thr Tyr Gly Thr His Leu Arg Glu Glu Tyr
385                 390                 395                 400

Phe Asn Glu Pro Leu Lys Phe Arg Pro Ser Arg Phe Glu Glu Asp Gly
                405                 410                 415

Arg Val Thr Pro Tyr Thr Phe Ile Pro Phe Gly Gly Gly Ala Arg Thr
            420                 425                 430

Cys Pro Gly Trp Glu Phe Ser Lys Thr Glu Ile Leu Leu Phe Ile His
        435                 440                 445

His Phe Val Arg Thr Phe Ser Ser Tyr Leu Pro Val Asp Ser Asn Glu
    450                 455                 460

Lys Ile Ser Ala Asp Pro Phe Pro Pro Leu Pro Ala Asn Gly Phe Ser
465                 470                 475                 480

Ile Lys Leu Ser Ala Asp Pro Phe Pro Pro Leu Pro Ala Asn Gly Phe
                485                 490                 495

Ser Ile Lys Leu Phe Pro Arg Ser Gln Ser Asn
            500                 505

<210> SEQ ID NO 66
<211> LENGTH: 512
<212> TYPE: PRT
<213> ORGANISM: Taxus cuspidata
<220> FEATURE:
<221> NAME/KEY: misc_feature
<222> LOCATION: (1)..(512)
<223> OTHER INFORMATION: "Xaa" equals any peptide

<400> SEQUENCE: 66

Met Ala Tyr Pro Glu Leu Leu Glu Asn Leu Ser Gly Asp Arg Ala Gln
1               5                   10                  15

Ser Pro Ala Ile Ala Ala Val Leu Thr Ile Leu Phe Leu Leu Gly Ile
            20                  25                  30

Phe Tyr Ile Leu Arg Gly Leu Arg Asn Asn Gly Arg Arg Leu Pro Pro
        35                  40                  45

Gly Pro Ile Pro Trp Pro Ile Val Gly Asn Leu His Gln Leu Gly Lys
    50                  55                  60

Leu Pro Asn Arg Asn Leu Glu Glu Leu Ala Lys Lys His Gly Pro Ile
65                  70                  75                  80

Met Leu Met Lys Leu Gly Ser Val Pro Ala Val Ile Val Ser Ser Ser
                85                  90                  95

Ala Met Ala Lys Glu Val Leu Lys Thr His Asp Leu Val Phe Ala Ser
            100                 105                 110

Arg Pro Glu Ser Ala Ala Gly Lys Tyr Ile Ala Tyr Asn Tyr Lys Asp
        115                 120                 125

Ile Val Phe Ser Pro Tyr Gly Pro Tyr Trp Arg Gln Met Lys Lys Ile
    130                 135                 140

Cys Val Val Glu Leu Leu Asn Ala Arg Arg Ile Glu Ser Leu Arg Ser
```

```
                145                 150                 155                 160
Val Arg Glu Glu Val Ser Val Ile Ile Arg Ser Val Trp Glu Lys
                165                 170                 175

Ser Lys Gln Gly Ala Val Ala Val Asn Leu Ser Lys Thr Leu Ser Ser
            180                 185                 190

Leu Thr Gln Gly Leu Met Leu Gln Ile Phe Ser Ser Asn Asp Asp Gly
            195                 200                 205

Gly Asn Ser Ser Val Thr Ala Ile Lys Glu Met Met Ser Glu Val Ser
        210                 215                 220

Glu Thr Ala Gly Ala Phe Asn Ile Gly Asp Tyr Phe Pro Trp Met Asp
225                 230                 235                 240

Trp Met Asp Leu Gln Gly Ile Gln Arg Arg Met Thr Lys Ala His Asp
                245                 250                 255

Tyr Phe Asp Gln Val Ile Thr Lys Ile Ile Glu Gln His Gln Arg Thr
                260                 265                 270

Arg Ala Met Glu Asp Thr Gln Gln Pro Lys Asp Ile Ile Asp Ala Leu
            275                 280                 285

Leu Gln Met Glu Asn Thr Asp Gly Val Thr Ile Thr Met Glu Asn Ile
        290                 295                 300

Lys Ala Val Val Leu Gly Ile Phe Leu Gly Gly Ala Glu Thr Thr Ser
305                 310                 315                 320

Thr Thr Leu Glu Trp Ala Met Ser Ala Met Leu Glu Asn Pro Glu Val
                325                 330                 335

Ala Lys Lys Val Gln Glu Glu Ile Glu Ser Val Val Gly Arg Lys Arg
            340                 345                 350

Val Val Lys Glu Met Ile Trp Glu Ser Met Glu Tyr Leu Gln Cys Val
        355                 360                 365

Val Lys Lys Thr Met Arg Leu Tyr Pro Ala Val Pro Leu Leu Ile Pro
370                 375                 380

His Glu Ser Thr Gln Asp Cys Thr Val Asn Gly Tyr Phe Ile Pro Glu
385                 390                 395                 400

Arg Thr Arg Ile Leu Val Asn Ala Trp Ala Ile Gly Lys Asp Pro Asn
                405                 410                 415

Val Trp Asp Asp Ala Leu Ala Phe Lys Pro Lys Arg Phe Leu Gly Xaa
            420                 425                 430

Asn Val Asp Leu Gln Lys Gly Lys Glu Phe Phe Asp Met Val Pro Phe
        435                 440                 445

Gly Ala Gly Arg Lys Gly Cys Pro Gly Ala Ser Met Ala Val Val Thr
        450                 455                 460

Met Glu His Ala Leu Ala Gln Leu Met His Cys Phe Gln Trp Arg Ile
465                 470                 475                 480

Glu Gly Glu Leu Asp Met Ser Glu Arg Leu Ala Ala Ser Val Gln Lys
                485                 490                 495

Lys Val Asp Leu Cys Val Leu Pro Gln Trp Arg Leu Thr Ser Ser Pro
            500                 505                 510

<210> SEQ ID NO 67
<211> LENGTH: 509
<212> TYPE: PRT
<213> ORGANISM: Taxus cuspidata

<400> SEQUENCE: 67

Met Asp Val Phe Tyr Pro Leu Lys Ser Thr Val Ala Lys Phe Asn Glu
1               5                   10                  15
```

```
Cys Phe Pro Ala Ile Leu Phe Ile Val Leu Ser Ala Val Ala Gly Ile
                20                  25                  30

Val Leu Pro Leu Leu Leu Phe Leu Arg Ser Lys Arg Ser Ser Val
        35                  40                  45

Gly Leu Pro Pro Gly Lys Leu Gly Tyr Pro Phe Ile Gly Glu Ser Leu
        50                  55                  60

Leu Phe Leu Lys Ala Leu Arg Ser Asn Thr Val Glu Gln Phe Leu Asp
65                  70                  75                  80

Glu Arg Val Lys Asn Phe Gly Asn Val Phe Lys Thr Ser Leu Ile Gly
                85                  90                  95

His Pro Thr Val Val Leu Cys Gly Pro Ala Gly Asn Arg Leu Ile Leu
            100                 105                 110

Ala Asn Glu Glu Lys Leu Val Gln Met Ser Trp Pro Lys Ser Ser Met
            115                 120                 125

Lys Leu Met Gly Glu Lys Ser Ile Thr Ala Lys Arg Gly Gly His
        130                 135                 140

Met Ile Ile Arg Ser Ala Leu Gln Gly Phe Phe Ser Pro Gly Ala Leu
145                 150                 155                 160

Gln Lys Tyr Ile Gly Gln Met Ser Lys Thr Ile Glu Asn His Ile Asn
                165                 170                 175

Glu Lys Trp Lys Gly Asn Asp Gln Val Ser Val Val Ala Leu Val Gly
            180                 185                 190

Asp Leu Val Phe Asp Ile Ser Ala Cys Leu Phe Phe Asn Ile Asn Glu
        195                 200                 205

Lys His Glu Arg Glu Arg Leu Phe Glu Leu Leu Glu Ile Ile Ala Val
            210                 215                 220

Gly Val Leu Ala Val Pro Val Asp Leu Pro Gly Phe Ala Tyr His Arg
225                 230                 235                 240

Ala Leu Gln Ala Arg Ser Lys Leu Asn Ala Ile Leu Ser Gly Leu Ile
                245                 250                 255

Glu Lys Arg Lys Met Asp Leu Ser Ser Gly Leu Ala Thr Ser Asn Gln
            260                 265                 270

Asp Leu Leu Ser Val Phe Leu Thr Phe Lys Asp Arg Gly Asn Pro
        275                 280                 285

Cys Ser Asp Glu Glu Ile Leu Asp Asn Phe Ser Gly Leu Leu His Gly
290                 295                 300

Ser Tyr Asp Thr Thr Val Ser Ala Met Ala Cys Val Phe Lys Leu Leu
305                 310                 315                 320

Ser Ser Asn Pro Glu Cys Tyr Glu Lys Val Val Gln Glu Gln Leu Gly
                325                 330                 335

Ile Leu Ser Asn Lys Leu Glu Gly Asp Glu Ile Thr Trp Lys Asp Val
            340                 345                 350

Lys Ser Met Lys Tyr Thr Trp Gln Val Val Gln Glu Thr Leu Arg Leu
        355                 360                 365

Tyr Pro Ser Ile Phe Gly Ser Phe Arg Gln Ala Ile Thr Asp Ile His
370                 375                 380

Tyr Asn Gly Tyr Ile Ile Pro Lys Gly Trp Lys Leu Leu Trp Thr Pro
385                 390                 395                 400

Tyr Thr Thr His Pro Lys Glu Met Tyr Phe Ser Glu Pro Glu Lys Phe
                405                 410                 415

Leu Pro Ser Arg Phe Asp Gln Glu Gly Lys Leu Val Ala Pro Tyr Thr
            420                 425                 430

Phe Leu Pro Phe Gly Gly Gly Gln Arg Ser Cys Pro Gly Trp Glu Phe
```

```
                435                 440                 445
Ser Lys Met Glu Ile Leu Leu Ser Val His His Phe Val Lys Thr Phe
    450                 455                 460

Ser Thr Phe Thr Pro Val Asp Pro Ala Glu Ile Ile Ala Arg Asp Ser
465                 470                 475                 480

Leu Cys Pro Leu Pro Ser Asn Gly Phe Ser Val Lys Leu Phe Pro Arg
                485                 490                 495

Ser Tyr Ser Leu His Thr Gly Asn Gln Val Lys Lys Ile
                500                 505

<210> SEQ ID NO 68
<211> LENGTH: 514
<212> TYPE: PRT
<213> ORGANISM: Taxus cuspidata

<400> SEQUENCE: 68

Met Ala Phe Glu Ala Ala Thr Val Ile Leu Phe Thr Leu Ala Ala Leu
1               5                   10                  15

Leu Leu Val Val Ile Gln Arg Arg Ile Arg Arg His Lys Leu Gln
            20                  25                  30

Gly Lys Val Lys Ala Pro Gln Pro Pro Ser Trp Pro Val Ile Gly Asn
        35                  40                  45

Leu His Leu Leu Thr Gln Lys Val Pro Ile His Arg Ile Leu Ser Ser
    50                  55                  60

Leu Ser Glu Ser Tyr Gly Pro Ile Met His Leu Gln Leu Gly Leu Arg
65              70                  75                  80

Pro Ala Leu Val Ile Ala Ser Ser Asp Leu Ala Lys Glu Cys Phe Thr
                85                  90                  95

Thr Asn Asp Lys Ala Phe Ala Ser Arg Pro Arg Leu Ser Ala Gly Lys
            100                 105                 110

His Val Gly Tyr Asp Tyr Lys Ile Phe Ser Met Ala Pro Tyr Gly Ser
        115                 120                 125

Tyr Trp Arg Asn Leu Arg Lys Met Cys Thr Ile Gln Ile Leu Ser Ala
    130                 135                 140

Thr Arg Ile Asp Ser Phe Arg His Ile Arg Val Glu Glu Val Ser Ala
145                 150                 155                 160

Leu Ile Arg Ser Leu Phe Asp Ser Cys Gln Arg Glu Asp Thr Pro Val
                165                 170                 175

Asn Met Lys Ala Arg Leu Ser Asp Leu Thr Phe Ser Ile Ile Leu Arg
            180                 185                 190

Met Val Ala Asn Lys Lys Leu Ser Gly Pro Val Tyr Ser Glu Glu Tyr
        195                 200                 205

Glu Glu Ala Asp His Phe Asn Gln Met Ile Lys Gln Ser Val Phe Leu
    210                 215                 220

Leu Gly Ala Phe Glu Val Gly Asp Phe Leu Pro Phe Leu Lys Trp Leu
225                 230                 235                 240

Asp Leu Gln Gly Phe Ile Ala Ala Met Lys Lys Leu Gln Gln Lys Arg
                245                 250                 255

Asp Val Phe Met Gln Lys Leu Val Ile Asp His Arg Glu Lys Arg Gly
            260                 265                 270

Arg Val Asp Ala Asn Ala Gln Asp Leu Ile Asp Val Leu Ile Ser Ala
        275                 280                 285

Thr Asp Asn His Glu Ile Gln Ser Asp Ser Asn Asp Val Val Lys
    290                 295                 300
```

```
Ala Thr Ala Leu Thr Met Leu Asn Ala Gly Thr Asp Thr Ser Ser Val
305                 310                 315                 320

Thr Ile Glu Trp Ala Leu Ala Ala Leu Met Gln His Pro His Ile Leu
            325                 330                 335

Ser Lys Ala Gln Gln Glu Leu Asp Thr His Ile Gly Arg Ser Arg Leu
        340                 345                 350

Leu Glu Glu Ala Asp Leu His Glu Leu Lys Tyr Leu Gln Ala Ile Val
    355                 360                 365

Lys Glu Thr Leu Arg Leu Tyr Pro Ala Ala Pro Leu Leu Val Pro His
370                 375                 380

Glu Ala Ile Glu Asp Cys Thr Val Gly Gly Tyr His Val Ser Ala Gly
385                 390                 395                 400

Thr Arg Leu Ile Val Asn Ala Trp Ala Ile His Arg Asp Pro Ala Val
                405                 410                 415

Trp Glu Arg Pro Thr Val Phe Asp Pro Glu Arg Phe Leu Lys Ser Gly
            420                 425                 430

Lys Glu Val Asp Val Lys Gly Arg Glu Phe Glu Leu Ile Pro Phe Gly
        435                 440                 445

Ser Gly Arg Arg Met Cys Pro Gly Met Ser Leu Ala Leu Ser Val Val
    450                 455                 460

Thr Tyr Thr Leu Gly Arg Leu Leu Gln Ser Phe Glu Trp Ser Val Pro
465                 470                 475                 480

Glu Gly Met Ile Ile Asp Met Thr Glu Gly Leu Gly Leu Thr Met Pro
                485                 490                 495

Lys Ala Val Pro Leu Glu Thr Ile Ile Lys Pro Arg Leu Pro Phe His
            500                 505                 510

Leu Tyr

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 69
tcggtgattg taacggaaga gc                                            22

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 70
ctggcttttc caacggagca tgag                                          24

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 71
attgtttctc agcccgcgca gtatg                                         25

<210> SEQ ID NO 72
```

```
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 72
tcggtttcta tgacggaagc gatg                                          24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 73
attaaccctc actaaacctt ttgg                                          24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 74
attaaccctc actaaacctt tcgg                                          24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 75
attaaccctc actaaaccat ttgg                                          24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 76
attaaccctc actaaaccat tcgg                                          24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 77
attaaccctc actaaaccgt ttgg                                          24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 78
```
attaaccctc actaaaccgt tcgg    24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 79
attaaccctc actaaacccct ttgg    24

<210> SEQ ID NO 80
<211> LENGTH: 1539
<212> TYPE: DNA
<213> ORGANISM: Taxus cuspidata

<400> SEQUENCE: 80

```
atggacgctt ttaatgtttt aatgggccct ctagcaaaat ttgataattt catgcagctc     60
ggctcttact ctgaaaatct ttccgttaca attaccgtca cagcgattgc cgtcattact    120
cttctcctgg tgttgatccg ttccaaaccc caatcttgtg taaaccttcc tccgggaaag    180
cttggctacc ctttcatcgg cgaaacatta caattgttgc aggcatttcg atcgaacagg    240
ccgcaacagt tctttgatga gaggcagaag aaatttgggt ctgttttcaa gacttcacta    300
attggggacc gcacagtggt gctgtgcggt ccctcaggaa accgtttgct gctctccaac    360
gaaaacaagc tggtggaggc atcctggccg agttcttcca ttaaattgat cggagaggat    420
tccattgctg ggaaaaacgg agagaagcat cggatcttac gcgccgcggt aaaccgttac    480
ctgggacccg agcattaca gaattatatg gcgaagatga ggtcagaaat cgaacatcat    540
atgaatgaga atggaagggg aaagagcaa gtgaaggtgc ttccctttggt aaaagagaat    600
gtcttctcca tcgcaaccag cttgttttt ggtgtcaatg atgacggaga acgggaacgg    660
cttcatgacc ttttggaaac cgcacttgcg ggtgtttttt ctattccact ggattttcca    720
ggaacaaatt atcggaaagc ccttgaagcg cggttaaaac tggataaagt cctttcttct    780
ctgatagaaa ggagaagaag cgatctgcga tcaggcgtgg catctggtaa tgaggatctg    840
ctctctgtgt ggctcacttt caaagacgaa aagggaatc tctgacaga caaggagatc    900
ctcgacaact tctccacctt gcttcatgca tcatatgaca ccacaacctc agcactcacc    960
ttgacattaa agctcatgtc ctcctctact gaatgctatc acaaagtagt tcaagagcaa   1020
ctgagaatag tttccaacaa aaaggaggga gaagaaatca gcttgaaaga tctgaaagac   1080
atgaaatata catggcaagt tgtgcaggaa actctgagga tgttccctcc gcttttttgga   1140
tcatttcgta aggccatcac tgacattcat tatgatggtt atacaatccc aaaaggatgg   1200
aaagttttat ggacaactta tagtacacat gggagagaag agtatttcaa tgaaccagag   1260
aaattcatgc cttcaagatt cgaagaggaa ggaaggcatg ttgctcctta cacattttta   1320
ccctttcggag caggcgtgcg cacctgccca ggatgggaat tttcaaaaac ccagatatta   1380
ctgttcttac attattttgt taaaactttc agtggctaca tcccactcga ccctgacgaa   1440
aaagtgttag ggaatccagt ccctcctctc cctgccaatg gatttgctat aaaacttttc   1500
cccaggccct cattcgatca aggatccccc atggaataa                          1539
```

<210> SEQ ID NO 81
<211> LENGTH: 1458
<212> TYPE: DNA

<213> ORGANISM: Taxus cuspidata

<400> SEQUENCE: 81

| | |
|---|---|
| atggatgccc ttaagcaatt ggaagtttcc ccttccattc ttttcgttac cctcgcagta | 60 |
| atggcaggca ttatcctctt cttccgctct aaacgccatt cctctgtaaa actccccct | 120 |
| ggaaatctag gcttccctct ggttggggag acactgcagt tcgtgaggtc acttggctcg | 180 |
| agcactccac agcagtttat tgaagagaga atgagcaaat tggggatgt gttcaagact | 240 |
| tccataatcg ggcatcccac agtagtgctg tgtggacctg ccggaaaccg gttggttctg | 300 |
| tcgaacgaga acaagctggt gcagatgtca tggccgagct ccatgatgaa actcatcggc | 360 |
| gaagattgtc tcggcggcaa aacgggagag cagcatcgga tcgtacgcgc tgcactaact | 420 |
| cggttttttgg gtcctcaagc attgcagaat catttcgcta aaatgagctc gggaatccaa | 480 |
| cgccacatca atgaaaaatg aagggaaag gatgaggcca ctgtacttcc tttggtaaaa | 540 |
| gacctcgtct tctccgtcgc aagccgcttg ttttttggta taactgagga gcacctgcag | 600 |
| gagcaacttc ataacttgtt ggaagttatt cttgtgggat cttttctgt ccactcaac | 660 |
| attcccggat tcagttacca taaagcgatt caggcaaggg ccaccctcgc tgacatcatg | 720 |
| acccatttga tagaaaagag gagaaatgag ctgcgtgcag gcactgcatc tgagaatcaa | 780 |
| gatttgctct ctgttttgct cactttcact gacgaaaggg ggaattcact gcggacaag | 840 |
| gagatcctcg acaactttc tatgttactt catggatcat atgactccac caattcccca | 900 |
| cttaccatgt tgattaaagt cttggcctcc catccagaaa gctatgaaaa agtggctcaa | 960 |
| gagcaatttg gaatactctc caccaaaatg gagggagaag aaattgcttg gaaagacctg | 1020 |
| aaggagatga atattcatg gcaagttgtt caggaaacat tgcgcatgta tcctcccatt | 1080 |
| tttggaacat ttcgcaaagc catcactgac attcattaca atggttatac aattccaaaa | 1140 |
| ggatggaaac ttttatggac aacttacagt actcaaacca aggaagagta ttcaaggac | 1200 |
| gccgatcaat tcaagccatc aagatttgag gaggaaggga agcatgtaac cccttacaca | 1260 |
| tacttacctt tcggaggagg catgcgtgtt tgtccagggt gggaattcgc caagatggag | 1320 |
| acattactgt ttctccatca ttttgttaaa gccttctctg ggttgaaggc aattgatcca | 1380 |
| aatgaaaaac tttcagggaa accacttcct cctctccctg tcaatgggct tcccattaaa | 1440 |
| ctctattcca gatcttaa | 1458 |

<210> SEQ ID NO 82
<211> LENGTH: 1482
<212> TYPE: DNA
<213> ORGANISM: Taxus cuspidata

<400> SEQUENCE: 82

| | |
|---|---|
| atggacagct tcactttgt aaccatcaaa atgggaaaaa tttggcaagt cattcaggtg | 60 |
| gagtacattc tatcccttac cctcacagct attcttctct tcttcttccg ttacagaaac | 120 |
| aaatcctctc ataaacttcc ccctggaaac ttgggcttcc cttttattgg ggagaccata | 180 |
| caattcttgc gttcacttcg atcacaaaca cctgaatttt ttttgacga gagggtgaag | 240 |
| aaattcggtc ctgttttcaa gacctcgcta attggggctc ccacagtgat attctgcggg | 300 |
| gcggcaggga gccgattagt tctgtctaac gaggacaagc tggtgcagat ggaatcgcca | 360 |
| agctctttaa agaagctaat gggggagaat tccattctgt ataaaagaga gaggaacac | 420 |
| cgcattttgc gttctgcatt atcccgcttt ttggtccccc aagctttgca aacttacatt | 480 |
| gctaaaatga gtacagaaat cgagcgtcat atcaacgaaa aatggaaggg aaaagaagaa | 540 |

```
gtgaagacgc ttcctttgat aagagggctc gtcttctcca ttgcaagcag tctgttttc      600 gatataaatg atgagcccca acaggagcga cttcatcatc atttggaaag tcttgttgca     660
ggaagtatgg ctgttcgcct cgactttcca ggaactcgct ttcgtaaagc cgttgaggcg    720
cgttcgaagc tggatgaagc tctccattct ttaataaaaa gcagacgaag cgatctgctt    780
tctggcaaag cttcaagtaa tcaagatctt cttccggtgc tgctcagctt caaagatgaa    840
agaggaaatc cactgagaga cgaggagatc ctcgacaatt tttctcttat acttcatgcc    900
tcgtatgata ccactatttc accaatggtt ttgacattga agctgctgtc ctccaatcca    960
gaatgctatg acaaagtagt tcaagagcaa tttggaatac ttgccaataa aaagaggga    1020 gaggaaatca gttggaagga tctgaaagct atgaaatata catggcaagt agtgcaggaa   1080
acactgagga tgttccctcc acttttgga tcattccgca aggctatggt tgatattaat   1140
tatgacggtt acacaattcc aaaggatgg atcgttttat ggacaactta cagtacacat   1200 gtgaagaag agtacttcaa tgaacctggc aaattcaggc cttcaagatt cgagcatgat   1260
ggaaggcatg tggctcctta cacattctta ccattcggag gaggcctgcg cacatgtcca   1320
ggatgggaat tctcaaagac ggagatatta ctgtttatcc atcattttgt taaaactttc   1380
ggcagctacc tcccagttga ccccaacgaa aaaatttcag cagatccatt ccctcctctc   1440
cctgccaatg gcttttctat aaaacttttt cccagatctt aa                       1482
```

<210> SEQ ID NO 83
<211> LENGTH: 1491
<212> TYPE: DNA
<213> ORGANISM: Taxus cuspidata

<400> SEQUENCE: 83

```
atggaactgt ggaatatgtt tctgccatgg atctccattg caacagcaac atcccttaca     60
gtgggcatgg catccgcatt cgctataatt tatgctcctc ttttgctgtc attcctgaga    120
ttgaagacgg ccagaagaaa tatgcctccg attcctccag gaagcatggg aatgccattc    180
tggggagaat ctctgggcta ctcggctca tggataacc agagcaaccc tgacgtgtgg    240
tacgacacac ggaaggccaa acacggcaaa attttcacaa cccacattct gggcagcccc    300
actgtggtca tgtgggtcc ggatgccaac aggttcatcc tcattaacga aaacaagctt    360
tttctcaaca gttggcccaa atctctcaac gctctcatcg gaaagcacgc cctcatcact    420
tcgcagggcg cagaacacaa aaggatgcgc cgaattatac attccgtgct cggcccaaga    480
aaccctgaaa ctagcgtggg aagattcgaa ggactggtgt tgcatcatct cgattccgac    540
tggcatggcg gccaaatcat ccaagcctac cgccaagtta aggacatggc gctctgtttg    600
gctgccgatt ttttcatggg gttaaagccc ggaaaagaat tggagacttt caggcggcat    660
ttcagtgatt tcagcgcggg gcttttatct caccctctcg atcttccctg gactgtgttt    720
gggaaggcga aacgagcgcg cgccgccatg gtcactcaga tttttttcaca aattcggctg    780 cataggactt ccatgcacaa aagtggagag gaggggggaa attcttgga catggtgttg    840 ggttcgcagg agaagggagg cgatttgagg ctgagtgagg aggagattgc agacaatctt    900
atgggtcttt taactggcgg acaggacacg acagcctcgg cattagccac cattctgaag    960 caccctctctc tctccccaca tctattacaa aggcttcgca aagagtgtga aaaacttaga   1020
gataacaagg aggcaggggg gcctcttaca tggagtgaaa taaaaagtgt gggctatta    1080 cacaatgtaa tctcagaagg actacggatg gtagccccca taaatggagg atttaagaaa   1140
```

-continued

| | |
|---|---|
| gcaaaagtag acgttgtata tggaggttat actattccca aaggatggaa ggttcattac | 1200 |
| tccgtgagac agacaaacaa caaagaagag tattttccta gtccagagag atttgatcca | 1260 |
| gatcgcttca atgagagaca tgagcctttt tctttcatcc ccttcggcca gggtaatcgg | 1320 |
| atgtgccccg gaaatgaatt cgcaaggttg gaaatggaat tatttctata tcatttggtt | 1380 |
| ttgagatatg attgggaatt aatggaggcg gatgaacgca ccaacatgta cttcattcct | 1440 |
| caccctgtgc acagtttgcc tttactactt aaacacgttc ctcctacatg a | 1491 |

<210> SEQ ID NO 84
<211> LENGTH: 1497
<212> TYPE: DNA
<213> ORGANISM: Taxus cuspidata

<400> SEQUENCE: 84

| | |
|---|---|
| atggacgccc tgtataagag cacagttgca aaatttaatg aggtcacaca gctggactgt | 60 |
| tccactgaat cttttttccat tgccctctca gctattgctg gtattcttct gcttctcctg | 120 |
| ctcttccgtt ctaaacgcca ctcctccctt aaacttcctc ctgggaaatt aggcatccct | 180 |
| ttcattggcg agtcgtttat cttcctgagg gctcttcgat cgaactcgct ggagcaattt | 240 |
| tttgacgaga gagtgaagaa attcggcctc gtgttcaaga cctccttgat tgggcatccc | 300 |
| acagtagtac tctgcggccc tgcgggaaac cggcttattc tgtccaacga ggagaagctg | 360 |
| gtgcagatgt cgtggcccgc tcaatttatg aagctcatgg gggagaattc cgttgccacc | 420 |
| aggaggggtg aagaccatat agttatgcgc tctgctcttg caggtttttt cggccctggt | 480 |
| gcgctgcaga gttacattgg taaaatgaat acagagatcc agtcatat caacgaaaaa | 540 |
| tggaagggaa aagatgaggt gaatgtactt cctttggtaa gagagctcgt cttcaacatt | 600 |
| tcggccatct tgttttttcaa catatatgat aagcaggaac aggatcgtct gcataagctt | 660 |
| ttggaaacta ttctggtcgg aagttttgct cttccgattg acttgcccgg atttggtttc | 720 |
| catagagcac tccagggacg ggccaagctc aacaaaatta tgctgtcttt aattaaaaag | 780 |
| agaaaagaag attgcagtct ggatcggcaa cagccacgca ggatctgctc tttgttttgc | 840 |
| tcactttcag agatgacaaa gggactccct cacccaatgg atgagatact cgacaacttt | 900 |
| tcttctctgc tccatgcctc ctatgacacc accacttcgc caatggcttt gattttcaag | 960 |
| ctcttgtctt ccaatccaga atgctatcaa aaagtagttc aagagcaatt ggagatcctt | 1020 |
| tccaacaaag aggagggcga agaaatcaca tggaaggatc tcaaagccat gaaatacaca | 1080 |
| tggcaagtag ctcaggaaac gctgcggatg tttcctccag ttttcggaac atttcgcaag | 1140 |
| gccatcactg acattcagta tgatggtacc aattccaaaa gggggaagct gttgtggaca | 1200 |
| acttacagta cacatcccaa ggacttgtat ttcaatgaac cagagaaatt catgccttca | 1260 |
| agattcgatc aggaaggaaa gcatgtagct ccttacacat ttttgccctt cggtggaggc | 1320 |
| caacggtcat gtgtgggatg ggaattttca aagatggaga tattactatt cgttcatcat | 1380 |
| tttgtcaaaa cttttagcag ctacacccca gttgatcccg acgaaaaaat atcaggggat | 1440 |
| ccactccctc ctcttccttc caagggattt tccattaaac tgtttccgag accatag | 1497 |

<210> SEQ ID NO 85
<211> LENGTH: 1461
<212> TYPE: DNA
<213> ORGANISM: Taxus cuspidata

<400> SEQUENCE: 85

| | |
|---|---|
| atggagcagc taatctatag tattgtctat tccaattggt atttatgggt tttgggactg | 60 |

```
tttatctgtg taattttact gttattaaga cggagtaatg acagacaagg gaatggatcc    120
gccaataaac ccaaacttcc acctggatca gctggattgc catttattgg agagactatc    180
cgttttctta gagacgctaa atcgcctgga cggcgaaagt tctttgatga acatgagctc    240
aggtatgggc cgattttcag atgtagtttg tttggaagaa cacgtgcagt tgtgtcggtg    300
gatcccgagt tcaataagta cgtcttgcaa aatgagggaa ggctgttcga atccaacgca    360
ctcgcgccct tcagaaatct tatcggcaaa tatggattgt cggcggtaca ggggaactt     420
caaaggaagc tccatgcaac tgctgtcaat ttgttgaagc atgagacgct cagctctgac    480
ttcatggaag atatacaaga catctttcag gctggaatga aaaatggga ggaggaggga    540
gacatcccta ttcaacacaa gtgcaatcag attgttctga acttgatggc gaagagattg    600
ctggacttac ctccatcaga gaaatgggaa catatttata aagctttcga cgatttcgtg    660
ggagctgtcc tctctttccc cctcaatatc cctggaacca cttatgcgag aggaattcgg    720
gccaggggaa ttctgttaaa aagaattcac aagtgtataa aggagaggag agaacatcca    780
gaggtgctcc gcaatgactt gttgaccaaa cttgtgaggg agggcacatt ttcggacgaa    840
attattgcag atacaataat cttttttgtg tttgctggtg tcgaaacttc agcaatggcc    900
atgacgtttg ctgtaaagta cctcgctgag aatccacgag cactggagga gttgagggct    960
gagcatgacg ctcttttgaa ggccaaaggg aaaggcaatg aaaagctgac gtggaatgac   1020
taccaatcaa tgaaattcgt tcattgtgta ataaatgaaa cacttcgtct gggtggtgca   1080
accgtggttc ttttcaggga agccaaacaa gatattaaag tgaaagattt tgttattccc   1140
aaaggatgga ccgtttctgt tttcttgagc gccacacatg ttgatggaaa ataccattat   1200
gaagctgaca aattcctccc ttggcgctgg caaaatgagg gtcaagaaac gttggaggag   1260
ccatgttata tgccatttgg aagaggtggc aggctctgtc caggactcca tttggcaaga   1320
tttgaaattg ctctctttct tcacaacttt gtcactaaat tcagatggga gcagctggaa   1380
attgatcgtg cgacttactt tcctcttcct tccacagaaa atggttttcc aatccgtctc   1440
tattctcgag tacacgaatg a                                             1461
```

<210> SEQ ID NO 86
<211> LENGTH: 1461
<212> TYPE: PRT
<213> ORGANISM: Taxus cuspidata

<400> SEQUENCE: 86

```
Ala Thr Gly Gly Ala Gly Cys Ala Gly Cys Thr Ala Ala Thr Cys Thr
 1               5                   10                  15

Ala Thr Ala Gly Thr Ala Thr Thr Gly Thr Cys Thr Ala Thr Thr Cys
            20                  25                  30

Cys Ala Ala Thr Thr Gly Gly Thr Ala Thr Thr Ala Thr Gly Gly
        35                  40                  45

Gly Thr Thr Thr Thr Gly Gly Gly Ala Cys Thr Gly Thr Thr Ala
    50                  55                  60

Thr Cys Thr Gly Thr Gly Thr Ala Ala Thr Thr Thr Ala Cys Thr
 65                  70                  75                  80

Gly Thr Thr Ala Thr Thr Ala Ala Gly Ala Cys Gly Gly Ala Gly Thr
                85                  90                  95

Ala Ala Thr Gly Ala Cys Ala Gly Ala Cys Ala Ala Gly Gly Gly Ala
            100                 105                 110

Ala Thr Gly Gly Ala Thr Cys Cys Gly Cys Cys Ala Ala Thr Ala Ala
```

-continued

```
            115                 120                 125
Ala Cys Cys Cys Ala Ala Cys Thr Thr Cys Ala Cys Cys Thr
        130                 135                 140
Gly Gly Ala Thr Cys Ala Gly Cys Thr Gly Ala Thr Gly Cys
145                 150                 155                 160
Cys Ala Thr Thr Thr Ala Thr Thr Gly Gly Ala Gly Ala Cys
                165                 170                 175
Thr Ala Thr Cys Cys Gly Thr Thr Thr Cys Thr Thr Ala Gly Ala
                180                 185                 190
Gly Ala Cys Gly Cys Thr Ala Ala Thr Cys Gly Cys Thr Gly
            195                 200                 205
Gly Ala Cys Gly Gly Cys Gly Ala Ala Ala Gly Thr Thr Cys Thr Thr
210                 215                 220
Thr Gly Ala Thr Gly Ala Ala Cys Ala Thr Gly Ala Gly Cys Thr Cys
225                 230                 235                 240
Ala Gly Gly Thr Ala Thr Gly Gly Cys Cys Gly Ala Thr Thr Thr
                245                 250                 255
Thr Cys Ala Gly Ala Thr Gly Thr Ala Gly Thr Thr Gly Thr Thr
            260                 265                 270
Thr Gly Gly Ala Ala Gly Ala Ala Cys Ala Cys Gly Thr Gly Cys Ala
            275                 280                 285
Gly Thr Thr Gly Thr Gly Thr Cys Gly Gly Thr Gly Gly Ala Thr Cys
        290                 295                 300
Cys Cys Gly Ala Gly Thr Thr Cys Ala Ala Thr Ala Ala Gly Thr Ala
305                 310                 315                 320
Cys Gly Thr Cys Thr Thr Gly Cys Ala Ala Ala Thr Gly Ala Gly
                325                 330                 335
Gly Gly Ala Ala Gly Gly Cys Thr Gly Thr Thr Cys Gly Ala Ala Thr
                340                 345                 350
Cys Cys Ala Ala Cys Gly Cys Ala Cys Thr Cys Gly Cys Gly Cys Cys
        355                 360                 365
Cys Thr Thr Cys Ala Gly Ala Ala Ala Thr Cys Thr Thr Ala Thr Cys
        370                 375                 380
Gly Gly Cys Ala Ala Ala Thr Ala Thr Gly Gly Ala Thr Thr Gly Thr
385                 390                 395                 400
Cys Gly Gly Cys Gly Gly Thr Ala Cys Ala Gly Gly Gly Gly Ala
                405                 410                 415
Ala Cys Thr Thr Cys Ala Ala Ala Gly Gly Ala Ala Gly Cys Thr Cys
        420                 425                 430
Cys Ala Thr Gly Cys Ala Ala Cys Thr Gly Cys Thr Gly Thr Cys Ala
        435                 440                 445
Ala Thr Thr Thr Gly Thr Thr Gly Ala Ala Gly Cys Ala Thr Gly Ala
    450                 455                 460
Gly Ala Cys Gly Cys Thr Cys Ala Gly Cys Thr Cys Thr Gly Ala Cys
465                 470                 475                 480
Thr Thr Cys Ala Thr Gly Gly Ala Ala Gly Ala Thr Ala Thr Ala Cys
                485                 490                 495
Ala Ala Gly Ala Cys Ala Thr Cys Thr Thr Cys Ala Gly Gly Cys
            500                 505                 510
Thr Gly Gly Ala Ala Thr Gly Ala Gly Ala Ala Ala Thr Gly Gly
        515                 520                 525
Gly Ala Gly Gly Ala Gly Gly Ala Gly Gly Gly Ala Gly Ala Cys Ala
530                 535                 540
```

-continued

```
Thr Cys Cys Cys Thr Ala Thr Cys Ala Ala Cys Ala Ala
545                 550                 555                 560

Gly Thr Gly Cys Ala Ala Thr Cys Ala Gly Ala Thr Gly Thr Thr
                565                 570                 575

Cys Thr Gly Ala Ala Cys Thr Thr Gly Ala Thr Gly Cys Gly Ala
                580                 585                 590

Ala Gly Ala Gly Ala Thr Thr Gly Cys Thr Gly Gly Ala Cys Thr Thr
        595                 600                 605

Ala Cys Cys Thr Cys Ala Thr Cys Ala Gly Ala Ala Gly Ala Ala
        610                 615                 620

Ala Thr Gly Gly Gly Ala Cys Ala Thr Ala Thr Thr Ala Thr Ala
625                 630                 635                 640

Ala Ala Gly Cys Thr Thr Thr Cys Gly Ala Cys Gly Ala Thr Thr Thr
                645                 650                 655

Cys Gly Thr Gly Gly Gly Ala Gly Cys Thr Gly Thr Cys Cys Thr Cys
                660                 665                 670

Thr Cys Thr Thr Thr Cys Cys Cys Cys Thr Cys Ala Ala Thr Ala
        675                 680                 685

Thr Cys Cys Cys Thr Gly Gly Ala Ala Cys Cys Ala Cys Thr Thr Ala
690                 695                 700

Thr Gly Cys Gly Ala Gly Ala Gly Gly Ala Ala Thr Cys Gly Gly
705                 710                 715                 720

Gly Cys Cys Ala Gly Gly Gly Ala Ala Thr Thr Cys Thr Gly Thr
                725                 730                 735

Thr Ala Ala Ala Ala Gly Ala Ala Thr Thr Cys Ala Cys Ala Ala
                740                 745                 750

Gly Thr Gly Thr Ala Thr Ala Ala Gly Gly Ala Gly Ala Gly Gly
        755                 760                 765

Ala Gly Ala Gly Ala Ala Cys Ala Thr Cys Cys Ala Gly Ala Gly Gly
770                 775                 780

Thr Gly Cys Thr Cys Cys Gly Cys Ala Ala Thr Gly Ala Cys Thr Thr
785                 790                 795                 800

Gly Thr Thr Gly Ala Cys Cys Ala Ala Ala Cys Thr Thr Gly Thr Gly
                805                 810                 815

Ala Gly Gly Gly Ala Gly Gly Gly Cys Ala Cys Ala Thr Thr Thr
        820                 825                 830

Cys Gly Gly Ala Cys Gly Ala Ala Ala Thr Thr Ala Thr Thr Gly Cys
        835                 840                 845

Ala Gly Ala Thr Ala Cys Ala Ala Thr Ala Ala Thr Cys Thr Thr Thr
850                 855                 860

Thr Thr Thr Gly Thr Gly Thr Thr Thr Gly Cys Thr Gly Gly Thr Gly
865                 870                 875                 880

Thr Cys Gly Ala Ala Ala Cys Thr Thr Cys Ala Gly Cys Ala Ala Thr
                885                 890                 895

Gly Gly Cys Cys Ala Thr Gly Ala Cys Gly Thr Thr Gly Cys Thr
                900                 905                 910

Gly Thr Ala Ala Ala Gly Thr Ala Cys Cys Thr Cys Gly Cys Thr Gly
        915                 920                 925

Ala Gly Ala Ala Thr Cys Cys Ala Cys Gly Ala Gly Cys Ala Cys Thr
        930                 935                 940

Gly Gly Ala Gly Gly Ala Gly Thr Thr Gly Ala Gly Gly Cys Thr
945                 950                 955                 960
```

Gly Ala Gly Cys Ala Thr Gly Ala Cys Gly Cys Thr Cys Thr Thr Thr
                965                 970                 975

Thr Gly Ala Ala Gly Gly Cys Ala Ala Ala Gly Gly Ala Ala
            980                 985                 990

Ala Gly Gly Cys Ala Ala Thr Gly Ala Ala Ala Gly Cys Thr Gly
            995                 1000                1005

Ala Cys Gly Thr Gly Gly Ala Ala Thr Gly Ala Cys Thr Ala Cys Cys
    1010                1015                1020

Ala Ala Thr Cys Ala Ala Thr Gly Ala Ala Ala Thr Thr Cys Gly Thr
1025                1030                1035                1040

Thr Cys Ala Thr Thr Gly Thr Gly Thr Ala Ala Thr Ala Ala Ala Thr
            1045                1050                1055

Gly Ala Ala Ala Cys Ala Cys Thr Thr Cys Gly Thr Cys Thr Gly Gly
            1060                1065                1070

Gly Thr Gly Gly Thr Gly Cys Ala Ala Cys Cys Gly Thr Gly Gly Thr
            1075                1080                1085

Thr Cys Thr Thr Thr Cys Ala Gly Gly Gly Ala Ala Gly Cys Cys
    1090                1095                1100

Ala Ala Ala Cys Ala Ala Gly Ala Thr Ala Thr Thr Ala Ala Ala Gly
1105                1110                1115                1120

Thr Gly Ala Ala Ala Gly Ala Thr Thr Thr Thr Gly Thr Thr Ala Thr
            1125                1130                1135

Thr Cys Cys Cys Ala Ala Ala Gly Gly Ala Thr Gly Gly Ala Cys Cys
    1140                1145                1150

Gly Thr Thr Thr Cys Thr Gly Thr Thr Thr Thr Cys Thr Thr Gly Ala
            1155                1160                1165

Gly Cys Gly Cys Ala Cys Ala Cys Ala Thr Gly Thr Thr Gly Ala
    1170                1175                1180

Thr Gly Gly Ala Ala Ala Ala Thr Ala Cys Cys Ala Thr Thr Ala Thr
1185                1190                1195                1200

Gly Ala Ala Gly Cys Thr Gly Ala Cys Ala Ala Ala Thr Thr Cys Cys
            1205                1210                1215

Thr Cys Cys Cys Thr Thr Gly Gly Cys Gly Cys Thr Gly Gly Cys Ala
    1220                1225                1230

Ala Ala Ala Thr Gly Ala Gly Gly Gly Thr Cys Ala Ala Gly Ala Ala
            1235                1240                1245

Ala Cys Gly Thr Thr Gly Gly Ala Gly Gly Ala Gly Cys Cys Ala Thr
    1250                1255                1260

Gly Thr Thr Ala Thr Ala Thr Gly Cys Cys Ala Thr Thr Thr Gly Gly
1265                1270                1275                1280

Ala Ala Gly Ala Gly Gly Thr Gly Gly Cys Ala Gly Gly Cys Thr Cys
            1285                1290                1295

Thr Gly Thr Cys Cys Ala Gly Gly Ala Cys Thr Cys Cys Ala Thr Thr
    1300                1305                1310

Thr Gly Gly Cys Ala Ala Gly Ala Thr Thr Thr Gly Ala Ala Ala Thr
    1315                1320                1325

Thr Gly Cys Thr Cys Thr Cys Thr Thr Cys Thr Thr Cys Ala Cys
    1330                1335                1340

Ala Ala Cys Thr Thr Thr Gly Thr Cys Ala Cys Thr Ala Ala Ala Thr
1345                1350                1355                1360

Thr Cys Ala Gly Ala Thr Gly Gly Gly Ala Gly Cys Ala Gly Cys Thr
            1365                1370                1375

Gly Gly Ala Ala Ala Thr Thr Gly Ala Thr Cys Gly Thr Gly Cys Gly

-continued

```
                1380                1385                1390
Ala Cys Thr Thr Ala Cys Thr Thr Cys Cys Thr Cys Thr Thr Cys
        1395                1400                1405
Cys Thr Thr Cys Cys Ala Cys Ala Gly Ala Ala Ala Thr Gly Gly
    1410                1415                1420
Thr Thr Thr Thr Cys Cys Ala Ala Thr Cys Cys Gly Thr Cys Thr Cys
1425                1430                1435                1440
Thr Ala Thr Thr Cys Thr Cys Gly Ala Gly Thr Ala Cys Ala Cys Gly
                1445                1450                1455
Ala Ala Thr Gly Ala
        1460

<210> SEQ ID NO 87
<211> LENGTH: 512
<212> TYPE: PRT
<213> ORGANISM: Taxus cuspidata

<400> SEQUENCE: 87

Met Asp Ala Phe Asn Val Leu Met Gly Pro Leu Ala Lys Phe Asp Asn
  1               5                  10                  15
Phe Met Gln Leu Gly Ser Tyr Ser Glu Asn Leu Ser Val Thr Ile Thr
             20                  25                  30
Val Thr Ala Ile Ala Val Ile Thr Leu Leu Val Leu Ile Arg Ser
         35                  40                  45
Lys Pro Gln Ser Cys Val Asn Leu Pro Pro Gly Lys Leu Gly Tyr Pro
     50                  55                  60
Phe Ile Gly Glu Thr Leu Gln Leu Leu Gln Ala Phe Arg Ser Asn Arg
 65                  70                  75                  80
Pro Gln Gln Phe Phe Asp Glu Arg Gln Lys Phe Gly Ser Val Phe
                 85                  90                  95
Lys Thr Ser Leu Ile Gly Asp Arg Thr Val Val Leu Cys Gly Pro Ser
            100                 105                 110
Gly Asn Arg Leu Leu Leu Ser Asn Glu Asn Lys Leu Val Glu Ala Ser
            115                 120                 125
Trp Pro Ser Ser Ser Ile Lys Leu Ile Gly Glu Asp Ser Ile Ala Gly
        130                 135                 140
Lys Asn Gly Glu Lys His Arg Ile Leu Arg Ala Ala Val Asn Arg Tyr
145                 150                 155                 160
Leu Gly Pro Gly Ala Leu Gln Asn Tyr Met Ala Lys Met Arg Ser Glu
                165                 170                 175
Ile Glu His His Met Asn Glu Lys Trp Lys Gly Lys Glu Gln Val Lys
            180                 185                 190
Val Leu Pro Leu Val Lys Glu Asn Val Phe Ser Ile Ala Thr Ser Leu
        195                 200                 205
Phe Phe Gly Val Asn Asp Asp Gly Glu Arg Glu Arg Leu His Asp Leu
    210                 215                 220
Leu Glu Thr Ala Leu Ala Gly Val Phe Ser Ile Pro Leu Asp Phe Pro
225                 230                 235                 240
Gly Thr Asn Tyr Arg Lys Ala Leu Glu Ala Arg Leu Lys Leu Asp Lys
                245                 250                 255
Val Leu Ser Ser Leu Ile Glu Arg Arg Ser Asp Leu Arg Ser Gly
            260                 265                 270
Val Ala Ser Gly Asn Glu Asp Leu Leu Ser Val Trp Leu Thr Phe Lys
        275                 280                 285
```

```
Asp Glu Glu Gly Asn Pro Leu Thr Asp Lys Glu Ile Leu Asp Asn Phe
        290                 295                 300

Ser Thr Leu Leu His Ala Ser Tyr Asp Thr Thr Ser Ala Leu Thr
305                 310                 315                 320

Leu Thr Leu Lys Leu Met Ser Ser Thr Glu Cys Tyr His Lys Val
                325                 330                 335

Val Gln Glu Gln Leu Arg Ile Val Ser Asn Lys Lys Glu Gly Glu Glu
        340                 345                 350

Ile Ser Leu Lys Asp Leu Lys Asp Met Lys Tyr Thr Trp Gln Val Val
        355                 360                 365

Gln Glu Thr Leu Arg Met Phe Pro Pro Leu Phe Gly Ser Phe Arg Lys
        370                 375                 380

Ala Ile Thr Asp Ile His Tyr Asp Gly Tyr Thr Ile Pro Lys Gly Trp
385                 390                 395                 400

Lys Val Leu Trp Thr Thr Tyr Ser Thr His Gly Arg Glu Glu Tyr Phe
                405                 410                 415

Asn Glu Pro Glu Lys Phe Met Pro Ser Arg Phe Glu Glu Gly Arg
        420                 425                 430

His Val Ala Pro Tyr Thr Phe Leu Pro Phe Gly Ala Gly Val Arg Thr
        435                 440                 445

Cys Pro Gly Trp Glu Phe Ser Lys Thr Gln Ile Leu Leu Phe Leu His
450                 455                 460

Tyr Phe Val Lys Thr Phe Ser Gly Tyr Ile Pro Leu Asp Pro Asp Glu
465                 470                 475                 480

Lys Val Leu Gly Asn Pro Val Pro Leu Pro Ala Asn Gly Phe Ala
                485                 490                 495

Ile Lys Leu Phe Pro Arg Pro Ser Phe Asp Gln Gly Ser Pro Met Glu
                500                 505                 510

<210> SEQ ID NO 88
<211> LENGTH: 485
<212> TYPE: PRT
<213> ORGANISM: Taxus cuspidata

<400> SEQUENCE: 88

Met Asp Ala Leu Lys Gln Leu Glu Val Ser Pro Ser Ile Leu Phe Val
1               5                   10                  15

Thr Leu Ala Val Met Ala Gly Ile Ile Leu Phe Phe Arg Ser Lys Arg
                20                  25                  30

His Ser Ser Val Lys Leu Pro Pro Gly Asn Leu Gly Phe Pro Leu Val
            35                  40                  45

Gly Glu Thr Leu Gln Phe Val Arg Ser Leu Gly Ser Ser Thr Pro Gln
        50                  55                  60

Gln Phe Ile Glu Glu Arg Met Ser Lys Phe Gly Asp Val Phe Lys Thr
65                  70                  75                  80

Ser Ile Ile Gly His Pro Thr Val Val Leu Cys Gly Pro Ala Gly Asn
                85                  90                  95

Arg Leu Val Leu Ser Asn Glu Asn Lys Leu Val Gln Met Ser Trp Pro
            100                 105                 110

Ser Ser Met Met Lys Leu Ile Gly Glu Asp Cys Leu Gly Gly Lys Thr
        115                 120                 125

Gly Glu Gln His Arg Ile Val Arg Ala Ala Leu Thr Arg Phe Leu Gly
    130                 135                 140

Pro Gln Ala Leu Gln Asn His Phe Ala Lys Met Ser Ser Gly Ile Gln
145                 150                 155                 160
```

```
Arg His Ile Asn Glu Lys Trp Lys Gly Lys Asp Glu Ala Thr Val Leu
                165                 170                 175
Pro Leu Val Lys Asp Leu Val Phe Ser Val Ala Ser Arg Leu Phe Phe
            180                 185                 190
Gly Ile Thr Glu Glu His Leu Gln Glu Gln Leu His Asn Leu Leu Glu
        195                 200                 205
Val Ile Leu Val Gly Ser Phe Ser Val Pro Leu Asn Ile Pro Gly Phe
    210                 215                 220
Ser Tyr His Lys Ala Ile Gln Ala Arg Ala Thr Leu Ala Asp Ile Met
225                 230                 235                 240
Thr His Leu Ile Glu Lys Arg Arg Asn Glu Leu Arg Ala Gly Thr Ala
                245                 250                 255
Ser Glu Asn Gln Asp Leu Leu Ser Val Leu Leu Thr Phe Thr Asp Glu
            260                 265                 270
Arg Gly Asn Ser Leu Ala Asp Lys Glu Ile Leu Asp Asn Phe Ser Met
        275                 280                 285
Leu Leu His Gly Ser Tyr Asp Ser Thr Asn Ser Pro Leu Thr Met Leu
    290                 295                 300
Ile Lys Val Leu Ala Ser His Pro Glu Ser Tyr Glu Lys Val Ala Gln
305                 310                 315                 320
Glu Gln Phe Gly Ile Leu Ser Thr Lys Met Glu Gly Glu Ile Ala
                325                 330                 335
Trp Lys Asp Leu Lys Glu Met Lys Tyr Ser Trp Gln Val Val Gln Glu
            340                 345                 350
Thr Leu Arg Met Tyr Pro Pro Ile Phe Gly Thr Phe Arg Lys Ala Ile
        355                 360                 365
Thr Asp Ile His Tyr Asn Gly Tyr Thr Ile Pro Lys Gly Trp Lys Leu
    370                 375                 380
Leu Trp Thr Thr Tyr Ser Thr Gln Thr Lys Glu Glu Tyr Phe Lys Asp
385                 390                 395                 400
Ala Asp Gln Phe Lys Pro Ser Arg Phe Glu Glu Gly Lys His Val
                405                 410                 415
Thr Pro Tyr Thr Tyr Leu Pro Phe Gly Gly Gly Met Arg Val Cys Pro
            420                 425                 430
Gly Trp Glu Phe Ala Lys Met Glu Thr Leu Leu Phe Leu His His Phe
        435                 440                 445
Val Lys Ala Phe Ser Gly Leu Lys Ala Ile Asp Pro Asn Glu Lys Leu
    450                 455                 460
Ser Gly Lys Pro Leu Pro Pro Leu Pro Val Asn Gly Leu Pro Ile Lys
465                 470                 475                 480
Leu Tyr Ser Arg Ser
                485

<210> SEQ ID NO 89
<211> LENGTH: 493
<212> TYPE: PRT
<213> ORGANISM: Taxus cuspidata

<400> SEQUENCE: 89

Met Asp Ser Phe Thr Phe Val Thr Ile Lys Met Gly Lys Ile Trp Gln
1               5                   10                  15
Val Ile Gln Val Glu Tyr Ile Leu Ser Leu Thr Leu Thr Ala Ile Leu
            20                  25                  30
Leu Phe Phe Phe Arg Tyr Arg Asn Lys Ser Ser His Lys Leu Pro Pro
```

-continued

```
                35                  40                  45
Gly Asn Leu Gly Phe Pro Phe Ile Gly Glu Thr Ile Gln Phe Leu Arg
 50                  55                  60

Ser Leu Arg Ser Gln Thr Pro Glu Phe Phe Asp Glu Arg Val Lys
 65                  70                  75                  80

Lys Phe Gly Pro Val Phe Lys Thr Ser Leu Ile Gly Ala Pro Thr Val
                 85                  90                  95

Ile Phe Cys Gly Ala Ala Gly Ser Arg Leu Val Leu Ser Asn Glu Asp
                100                 105                 110

Lys Leu Val Gln Met Glu Ser Pro Ser Leu Lys Lys Leu Met Gly
                115                 120                 125

Glu Asn Ser Ile Leu Tyr Lys Arg Glu Glu His Arg Ile Leu Arg
130                 135                 140

Ser Ala Leu Ser Arg Phe Leu Gly Pro Gln Ala Leu Gln Thr Tyr Ile
145                 150                 155                 160

Ala Lys Met Ser Thr Glu Ile Glu Arg His Ile Asn Glu Lys Trp Lys
                165                 170                 175

Gly Lys Glu Glu Val Lys Thr Leu Pro Leu Ile Arg Gly Leu Val Phe
                180                 185                 190

Ser Ile Ala Ser Ser Leu Phe Phe Asp Ile Asn Asp Glu Pro Gln Gln
                195                 200                 205

Glu Arg Leu His His His Leu Glu Ser Leu Val Ala Gly Ser Met Ala
210                 215                 220

Val Arg Leu Asp Phe Pro Gly Thr Arg Phe Arg Lys Ala Val Glu Ala
225                 230                 235                 240

Arg Ser Lys Leu Asp Glu Ala Leu His Ser Leu Ile Lys Ser Arg Arg
                245                 250                 255

Ser Asp Leu Leu Ser Gly Lys Ala Ser Ser Asn Gln Asp Leu Leu Ser
                260                 265                 270

Val Leu Leu Ser Phe Lys Asp Glu Arg Gly Asn Pro Leu Arg Asp Glu
                275                 280                 285

Glu Ile Leu Asp Asn Phe Ser Leu Ile Leu His Ala Ser Tyr Asp Thr
                290                 295                 300

Thr Ile Ser Pro Met Val Leu Thr Leu Lys Leu Leu Ser Ser Asn Pro
305                 310                 315                 320

Glu Cys Tyr Asp Lys Val Val Gln Glu Gln Phe Gly Ile Leu Ala Asn
                325                 330                 335

Lys Lys Glu Gly Glu Glu Ile Ser Trp Lys Asp Leu Lys Ala Met Lys
                340                 345                 350

Tyr Thr Trp Gln Val Val Gln Glu Thr Leu Arg Met Phe Pro Pro Leu
                355                 360                 365

Phe Gly Ser Phe Arg Lys Ala Met Val Asp Ile Asn Tyr Asp Gly Tyr
                370                 375                 380

Thr Ile Pro Lys Gly Trp Ile Val Leu Trp Thr Thr Tyr Ser Thr His
385                 390                 395                 400

Val Lys Glu Glu Tyr Phe Asn Glu Pro Gly Lys Phe Arg Pro Ser Arg
                405                 410                 415

Phe Glu His Asp Gly Arg His Val Ala Pro Tyr Thr Phe Leu Pro Phe
                420                 425                 430

Gly Gly Gly Leu Arg Thr Cys Pro Gly Trp Glu Phe Ser Lys Thr Glu
                435                 440                 445

Ile Leu Leu Phe Ile His His Phe Val Lys Thr Phe Gly Ser Tyr Leu
                450                 455                 460
```

```
Pro Val Asp Pro Asn Glu Lys Ile Ser Ala Asp Pro Phe Pro Pro Leu
465                 470                 475                 480

Pro Ala Asn Gly Phe Ser Ile Lys Leu Phe Pro Arg Ser
                485                 490
```

<210> SEQ ID NO 90
<211> LENGTH: 496
<212> TYPE: PRT
<213> ORGANISM: Taxus cuspidata

<400> SEQUENCE: 90

```
Met Glu Leu Trp Asn Met Phe Leu Pro Trp Ile Ser Ile Ala Thr Ala
 1               5                  10                  15

Thr Ser Leu Thr Val Gly Met Ala Ser Ala Phe Ala Ile Ile Tyr Ala
                20                  25                  30

Pro Leu Leu Leu Ser Phe Leu Arg Leu Lys Thr Ala Arg Arg Asn Met
            35                  40                  45

Pro Pro Ile Pro Pro Gly Ser Met Gly Met Pro Phe Trp Gly Glu Ser
50                  55                  60

Leu Gly Tyr Leu Gly Ser Trp Asn Asn Gln Ser Asn Pro Asp Val Trp
65                  70                  75                  80

Tyr Asp Thr Arg Lys Ala Lys His Gly Lys Ile Phe Thr Thr His Ile
                85                  90                  95

Leu Gly Ser Pro Thr Val Val Met Leu Gly Pro Asp Ala Asn Arg Phe
            100                 105                 110

Ile Leu Ile Asn Glu Asn Lys Leu Phe Leu Asn Ser Trp Pro Lys Ser
        115                 120                 125

Leu Asn Ala Leu Ile Gly Lys His Ala Leu Ile Thr Ser Gln Gly Ala
130                 135                 140

Glu His Lys Arg Met Arg Arg Ile Ile His Ser Val Leu Gly Pro Arg
145                 150                 155                 160

Asn Pro Glu Thr Ser Val Gly Arg Phe Glu Gly Leu Val Leu His His
                165                 170                 175

Leu Asp Ser Asp Trp His Gly Gly Gln Ile Ile Gln Ala Tyr Arg Gln
            180                 185                 190

Val Lys Asp Met Ala Leu Cys Leu Ala Ala Asp Phe Phe Met Gly Leu
        195                 200                 205

Lys Pro Gly Lys Glu Leu Glu Thr Phe Arg Arg His Phe Ser Asp Phe
210                 215                 220

Ser Ala Gly Leu Leu Ser His Pro Leu Asp Leu Pro Trp Thr Val Phe
225                 230                 235                 240

Gly Lys Ala Lys Arg Ala Arg Ala Ala Met Val Thr Gln Ile Phe Ser
                245                 250                 255

Gln Ile Arg Leu His Arg Thr Ser Met His Lys Ser Gly Glu Glu Gly
            260                 265                 270

Gly Asn Phe Leu Asp Met Val Leu Gly Ser Gln Glu Lys Gly Gly Asp
        275                 280                 285

Leu Arg Leu Ser Glu Glu Ile Ala Asp Asn Met Gly Leu Leu
290                 295                 300

Thr Gly Gly Gln Asp Thr Thr Ala Ser Ala Leu Ala Thr Ile Leu Lys
305                 310                 315                 320

His Leu Ser Leu Ser Pro His Leu Leu Gln Arg Leu Arg Lys Glu Cys
                325                 330                 335

Glu Lys Leu Arg Asp Asn Lys Glu Ala Gly Gly Pro Leu Thr Trp Ser
```

-continued

```
                340                 345                 350
Glu Ile Lys Ser Val Gly Tyr Leu His Asn Val Ile Ser Glu Gly Leu
            355                 360                 365

Arg Met Val Ala Pro Ile Asn Gly Gly Phe Lys Lys Ala Lys Val Asp
        370                 375                 380

Val Val Tyr Gly Gly Tyr Thr Ile Pro Lys Gly Trp Lys Val His Tyr
385                 390                 395                 400

Ser Val Arg Gln Thr Asn Asn Lys Glu Glu Tyr Phe Pro Ser Pro Glu
                405                 410                 415

Arg Phe Asp Pro Asp Arg Phe Asn Glu Arg His Glu Pro Phe Ser Phe
            420                 425                 430

Ile Pro Phe Gly Gln Gly Asn Arg Met Cys Pro Gly Asn Glu Phe Ala
        435                 440                 445

Arg Leu Glu Met Glu Leu Phe Leu Tyr His Leu Val Leu Arg Tyr Asp
    450                 455                 460

Trp Glu Leu Met Glu Ala Asp Glu Arg Thr Asn Met Tyr Phe Ile Pro
465                 470                 475                 480

His Pro Val His Ser Leu Pro Leu Leu Leu Lys His Val Pro Pro Thr
                485                 490                 495
```

<210> SEQ ID NO 91
<211> LENGTH: 498
<212> TYPE: PRT
<213> ORGANISM: Taxus cuspidata

<400> SEQUENCE: 91

```
Met Asp Ala Leu Tyr Lys Ser Thr Val Ala Lys Phe Asn Glu Val Thr
 1               5                  10                  15

Gln Leu Asp Cys Ser Thr Glu Ser Phe Ser Ile Ala Leu Ser Ala Ile
            20                  25                  30

Ala Gly Ile Leu Leu Leu Leu Leu Phe Arg Ser Lys Arg His Ser
        35                  40                  45

Ser Leu Lys Leu Pro Pro Gly Lys Leu Gly Ile Pro Phe Ile Gly Glu
    50                  55                  60

Ser Phe Ile Phe Leu Arg Ala Leu Arg Ser Asn Ser Leu Glu Gln Phe
65                  70                  75                  80

Phe Asp Glu Arg Val Lys Lys Phe Gly Leu Val Phe Lys Thr Ser Leu
                85                  90                  95

Ile Gly His Pro Thr Val Val Leu Cys Gly Pro Ala Gly Asn Arg Leu
            100                 105                 110

Ile Leu Ser Asn Glu Glu Lys Leu Val Gln Met Ser Trp Pro Ala Gln
        115                 120                 125

Phe Met Lys Leu Met Gly Glu Asn Ser Val Ala Thr Arg Arg Gly Glu
    130                 135                 140

Asp His Ile Val Met Arg Ser Ala Leu Ala Gly Phe Phe Gly Pro Gly
145                 150                 155                 160

Ala Leu Gln Ser Tyr Ile Gly Lys Met Asn Thr Glu Ile Gln Ser His
                165                 170                 175

Ile Asn Glu Lys Trp Lys Gly Lys Asp Glu Val Asn Val Leu Pro Leu
            180                 185                 190

Val Arg Glu Leu Val Phe Asn Ile Ser Ala Ile Leu Phe Phe Asn Ile
        195                 200                 205

Tyr Asp Lys Gln Glu Gln Asp Arg Leu His Lys Leu Leu Glu Thr Ile
    210                 215                 220
```

-continued

```
Leu Val Gly Ser Phe Ala Leu Pro Ile Asp Leu Pro Gly Phe Gly Phe
225                 230                 235                 240

His Arg Ala Leu Gln Gly Arg Ala Lys Leu Asn Lys Ile Met Leu Ser
                245                 250                 255

Leu Ile Lys Lys Arg Lys Glu Asp Cys Ser Leu Asp Arg Gln Gln Pro
            260                 265                 270

Arg Arg Ile Cys Ser Leu Phe Cys Ser Leu Ser Glu Met Thr Lys Gly
        275                 280                 285

Leu Pro His Pro Met Asp Glu Ile Leu Asp Asn Phe Ser Ser Leu Leu
    290                 295                 300

His Ala Ser Tyr Asp Thr Thr Ser Pro Met Ala Leu Ile Phe Lys
305                 310                 315                 320

Leu Leu Ser Ser Asn Pro Glu Cys Tyr Gln Lys Val Val Gln Glu Gln
                325                 330                 335

Leu Glu Ile Leu Ser Asn Lys Glu Glu Gly Glu Ile Thr Trp Lys
            340                 345                 350

Asp Leu Lys Ala Met Lys Tyr Thr Trp Gln Val Ala Gln Glu Thr Leu
        355                 360                 365

Arg Met Phe Pro Pro Val Phe Gly Thr Phe Arg Lys Ala Ile Thr Asp
    370                 375                 380

Ile Gln Tyr Asp Gly Thr Asn Ser Lys Arg Gly Lys Leu Leu Trp Thr
385                 390                 395                 400

Thr Tyr Ser Thr His Pro Lys Asp Leu Tyr Phe Asn Glu Pro Glu Lys
                405                 410                 415

Phe Met Pro Ser Arg Phe Asp Gln Glu Gly Lys His Val Ala Pro Tyr
            420                 425                 430

Thr Phe Leu Pro Phe Gly Gly Gly Gln Arg Ser Cys Val Gly Trp Glu
        435                 440                 445

Phe Ser Lys Met Glu Ile Leu Leu Phe Val His His Phe Val Lys Thr
    450                 455                 460

Phe Ser Ser Tyr Thr Pro Val Asp Pro Asp Glu Lys Ile Ser Gly Asp
465                 470                 475                 480

Pro Leu Pro Pro Leu Pro Ser Lys Gly Phe Ser Ile Lys Leu Phe Pro
                485                 490                 495

Arg Pro
```

<210> SEQ ID NO 92
<211> LENGTH: 486
<212> TYPE: PRT
<213> ORGANISM: Taxus cuspidata

<400> SEQUENCE: 92

```
Met Glu Gln Leu Ile Tyr Ser Ile Val Tyr Ser Asn Trp Tyr Leu Trp
1               5                   10                  15

Val Leu Gly Leu Phe Ile Cys Val Ile Leu Leu Leu Arg Arg Ser
            20                  25                  30

Asn Asp Arg Gln Gly Asn Gly Ser Ala Asn Lys Pro Lys Leu Pro Pro
        35                  40                  45

Gly Ser Ala Gly Leu Pro Phe Ile Gly Glu Thr Ile Arg Phe Leu Arg
    50                  55                  60

Asp Ala Lys Ser Pro Gly Arg Arg Lys Phe Phe Asp Glu His Glu Leu
65                  70                  75                  80

Arg Tyr Gly Pro Ile Phe Arg Cys Ser Leu Phe Gly Arg Thr Arg Ala
                85                  90                  95
```

```
Val Val Ser Val Asp Pro Glu Phe Asn Lys Tyr Val Leu Gln Asn Glu
            100                 105                 110

Gly Arg Leu Phe Glu Ser Asn Ala Leu Ala Pro Phe Arg Asn Leu Ile
            115                 120                 125

Gly Lys Tyr Gly Leu Ser Ala Val Gln Gly Glu Leu Gln Arg Lys Leu
        130                 135                 140

His Ala Thr Ala Val Asn Leu Leu Lys His Glu Thr Leu Ser Ser Asp
145                 150                 155                 160

Phe Met Glu Asp Ile Gln Asp Ile Phe Gln Ala Gly Met Arg Lys Trp
                165                 170                 175

Glu Glu Glu Gly Asp Ile Pro Ile Gln His Lys Cys Asn Gln Ile Val
            180                 185                 190

Leu Asn Leu Met Ala Lys Arg Leu Leu Asp Leu Pro Pro Ser Glu Glu
            195                 200                 205

Met Gly His Ile Tyr Lys Ala Phe Asp Asp Phe Val Gly Ala Val Leu
    210                 215                 220

Ser Phe Pro Leu Asn Ile Pro Gly Thr Thr Tyr Ala Arg Gly Ile Arg
225                 230                 235                 240

Ala Arg Gly Ile Leu Leu Lys Arg Ile His Lys Cys Ile Lys Glu Arg
                245                 250                 255

Arg Glu His Pro Glu Val Leu Arg Asn Asp Leu Leu Thr Lys Leu Val
            260                 265                 270

Arg Glu Gly Thr Phe Ser Asp Glu Ile Ile Ala Asp Thr Ile Ile Phe
        275                 280                 285

Phe Val Phe Ala Gly Val Glu Thr Ser Ala Met Ala Met Thr Phe Ala
290                 295                 300

Val Lys Tyr Leu Ala Glu Asn Pro Arg Ala Leu Glu Glu Leu Arg Ala
305                 310                 315                 320

Glu His Asp Ala Leu Leu Lys Ala Lys Gly Lys Gly Asn Glu Lys Leu
                325                 330                 335

Thr Trp Asn Asp Tyr Gln Ser Met Lys Phe Val His Cys Val Ile Asn
            340                 345                 350

Glu Thr Leu Arg Leu Gly Gly Ala Thr Val Val Leu Phe Arg Glu Ala
        355                 360                 365

Lys Gln Asp Ile Lys Val Lys Asp Phe Val Ile Pro Lys Gly Trp Thr
370                 375                 380

Val Ser Val Phe Leu Ser Ala Thr His Val Asp Gly Lys Tyr His Tyr
385                 390                 395                 400

Glu Ala Asp Lys Phe Leu Pro Trp Arg Trp Gln Asn Glu Gly Gln Glu
                405                 410                 415

Thr Leu Glu Glu Pro Cys Tyr Met Pro Phe Gly Arg Gly Arg Leu
            420                 425                 430

Cys Pro Gly Leu His Leu Ala Arg Phe Glu Ile Ala Leu Phe Leu His
        435                 440                 445

Asn Phe Val Thr Lys Phe Arg Trp Glu Gln Leu Glu Ile Asp Arg Ala
450                 455                 460

Thr Tyr Phe Pro Leu Pro Ser Thr Glu Asn Gly Phe Pro Ile Arg Leu
465                 470                 475                 480

Tyr Ser Arg Val His Glu
                485

<210> SEQ ID NO 93
<211> LENGTH: 26
<212> TYPE: DNA
```

```
<213> ORGANISM: Artificial Sequence
<220> FEATURE:
<223> OTHER INFORMATION: Description of Artificial Sequence:  PCR primer

<400> SEQUENCE: 93
atggccctta agcaattgga agtttc                                          26

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence: PCR Primer

<400> SEQUENCE: 94
ttaagatctg gaatagagtt taatgg                                          26

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 95
attaaccctc actaaaccct tcgg                                            24
```